(12) United States Patent
Pan et al.

(10) Patent No.: US 10,723,705 B2
(45) Date of Patent: Jul. 28, 2020

(54) HETEROCYCLIC COMPOUNDS AND USES THEREOF

(71) Applicant: Incyte Corporation, Wilmington, DE (US)

(72) Inventors: Jun Pan, Wilmington, DE (US); Xiaozhao Wang, Wilmington, DE (US); Joseph Barbosa, Wilmington, DE (US); Wenqing Yao, Wilmington, DE (US); Yingda Ye, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 15/752,807

(22) PCT Filed: Aug. 12, 2016

(86) PCT No.: PCT/US2016/046725
§ 371 (c)(1),
(2) Date: Feb. 14, 2018

(87) PCT Pub. No.: WO2017/030938
PCT Pub. Date: Feb. 23, 2017

(65) Prior Publication Data
US 2018/0244627 A1   Aug. 30, 2018

Related U.S. Application Data

(60) Provisional application No. 62/205,513, filed on Aug. 14, 2015.

(51) Int. Cl.
| | |
|---|---|
| *A61K 31/437* | (2006.01) |
| *C07D 401/14* | (2006.01) |
| *C07D 231/56* | (2006.01) |
| *C07D 401/04* | (2006.01) |
| *C07D 403/04* | (2006.01) |
| *C07D 471/04* | (2006.01) |
| *C07D 487/04* | (2006.01) |
| *A61K 31/416* | (2006.01) |
| *A61K 31/4184* | (2006.01) |
| *A61K 31/435* | (2006.01) |
| *A61K 31/4439* | (2006.01) |
| *A61K 31/444* | (2006.01) |
| *A61K 31/454* | (2006.01) |
| *A61K 31/496* | (2006.01) |
| *A61K 31/506* | (2006.01) |
| *A61K 31/5377* | (2006.01) |
| *A61K 45/06* | (2006.01) |
| *C07D 235/06* | (2006.01) |
| *C07D 401/06* | (2006.01) |
| *C07D 403/06* | (2006.01) |
| *C07D 405/12* | (2006.01) |
| *C07D 491/044* | (2006.01) |

(52) U.S. Cl.
CPC .......... *C07D 231/56* (2013.01); *A61K 31/416* (2013.01); *A61K 31/4184* (2013.01); *A61K 31/435* (2013.01); *A61K 31/437* (2013.01); *A61K 31/444* (2013.01); *A61K 31/4439* (2013.01); *A61K 31/454* (2013.01); *A61K 31/496* (2013.01); *A61K 31/506* (2013.01); *A61K 31/5377* (2013.01); *A61K 45/06* (2013.01); *C07D 235/06* (2013.01); *C07D 401/04* (2013.01); *C07D 401/06* (2013.01); *C07D 403/04* (2013.01); *C07D 403/06* (2013.01); *C07D 405/12* (2013.01); *C07D 471/04* (2013.01); *C07D 487/04* (2013.01); *C07D 491/044* (2013.01)

(58) Field of Classification Search
CPC .......................... C07D 401/14; A61K 31/437
USPC .......................................... 546/119; 514/303
See application file for complete search history.

(56) References Cited

U.S. PATENT DOCUMENTS

| | | | | |
|---|---|---|---|---|
| 8,431,593 | B2* | 4/2013 | Hutchison | ............ C07D 471/04 514/299 |
| 8,580,812 | B2* | 11/2013 | Ihle | ...................... C07D 471/04 514/299 |
| 2009/0181943 | A1 | 7/2009 | Tessier et al. | |
| 2015/0352079 | A1 | 12/2015 | Beeler et al. | |
| 2018/0244627 | A1 | 8/2018 | Pan et al. | |

FOREIGN PATENT DOCUMENTS

| | | |
|---|---|---|
| WO | WO 2006/077425 | 7/2006 |
| WO | WO 2006/101455 | 9/2006 |
| WO | WO 2007/030080 | 3/2007 |
| WO | WO 2008/100867 | 8/2008 |
| WO | WO 2014/116962 | 7/2014 |
| WO | WO 2017/030938 | 2/2017 |

OTHER PUBLICATIONS

Morgenthaler et al., Journal of Fluorine Chemistry (2008), 129(9), 852-865.*
Sahli et al., Helvetica Chimica Acta (2005), 88(4), 731-750.*
Sahli et al., ChemBioChem (2004), 5(7), 996-1000.*
Ayalp et al.,Pakistan Journal of pharmaceutical Science (1989), 2(1), 7-12.*
Kuzmierkiewicz et al., Pharmazie (1985), 40(7), 462-4.*
Angell et al., "Base Dependence in Copper-Catalyzed Huisgen Reactions: Efficient Formation of Bistriazoles," *Angew. Chem. Int. Ed.*, 2007, 46:3649-3651.
Balasubramanian et al., "A novel histone deacetylase 8 (HDAC8)-specific inhibitor PCI-34051 induces apoptosis in T-cell lymphomas," *Leukemia*, Feb. 7, 2008, 22(5):1026-1034.

(Continued)

*Primary Examiner* — Niloofar Rahmani
(74) *Attorney, Agent, or Firm* — Fish & Richardson P.C.

(57) ABSTRACT

The present disclosure relates to heterocyclic compounds, and pharmaceutical compositions of the same, that are modulators/inhibitors of HDACs, such as HDAC8 and are useful in the treatment of HDAC-associated diseases.

24 Claims, No Drawings

(56) References Cited

OTHER PUBLICATIONS

Blass et al., "Solution Phase Synthesis of Imidazo [1, 2-b] pyrazol-2-one, an interesting 5, 5-fused heterocyclic ring system," Tetrahedron Letters, Jan. 12, 2004, 45(3):619-621.
Blom, "Two-Pump at Column Dilution Configuration for Preparative LC-MS," *J. Combi. Chem.*, Apr. 12, 2002, 4(4):295-301.
Blom et al., "Optimizing Preparative LC-MS Configurations and Methods for Parallel Synthesis Purification," *J. Comb. Chem.*, Jul. 29, 2003, 5(5):670-683.
Blom et al., "Preparative LC-MS Purification: Improved Compound Specific Method Optimization," *J. Comb. Chem.*, Sep. 11, 2004, 6(6):874-883.
Deardorff et al., "HDAC8 mutations in Cornelia de Lange syndrome affect the cohesin acetylation cycle," *Nature*, Sep. 13, 2012, 489(7415):313-317.
Gerard et al, "Synthesis of 1.4,5-trisubstituted-1 ,2,3-triazoles by copper-catalyzed cycloaddition-coupling of azides and terminal aklynes," Tetrahedron, 2006, 62:6405-6411.
Li et al., "Targeting Histone Deacetylases for Cancer Therapy: From Molecular Mechanisms to Clinical Implications," *Int. J. Biol. Sci*, Jul. 2, 2014, 10(7):757-770.
Olson et al., "An unbiased approach to identify endogenous substrates of "histone" deacetylase 8," *Chem Biol.*, 2014, 9(10):2210-2216.
Falkenberg et al., "Histone deacetylases and their inhibitors in cancer, neurological diseases and immune disorders," *Nat. Rev. Drug. Discov.*, Aug. 18, 2014, 13(9):673-691.
Gao, et al. "Histone deacetylases inhibitor sodium butyrate inhibits JAK2/STAT signaling through upregulation of SOCS1 and SOCS3 mediated by HDAC8 inhibition in myeloproliferative neoplasms," *Exp. Hematol.*, Mar. 2013, 41(3):261-270.
International Preliminary Report on Patentability in International Application No. PCT/US2016/046725, dated Feb. 20, 2018, 8 pages.
International Search Report and Written Opinion in International Application No. PCT/US2016/046725, dated Feb. 2, 2016, 11 pages.
Jing et al., "Low-Dose secondary prophylaxis May Decrease Haemorrhage and Improve Health-Related Quality of Life in Adults with Severe Hemophilia," Blood, 124(21):2819-.
Berge, "Pharmaceutical Salts," *Journal of Pharmaceutical Science*, Jan. 1977, 66(1):1-19.
Kang et al., "HDAC8 and STAT3 repress BMF gene activity in colon cancer cells," *Cell Death Dis.*,Oct. 16, 2014, 5:e1476.
Kocienski, *Protecting Groups*, 3rd Edition, Georg Thieme Verlag, 2007 :50-61.
Kroesen et al., "HDAC inhibitors and immunotherapy; a double edged sword?" *Oncotarget*, Jul. 31, 2014, 5(16):6558-6572.
Li et al., "HPV16E7 mediates HADC chromatin repression and downregulation of MHC class I genes in HPV16 tumorigenic cells through interaction with an MHC class I promoter," *Biochem Biophys Res Commun.*, Nov. 2006, 349(4): 1315-1321.
Oehme et al., "Histone deacetylase 8 in neuroblastoma tumorigenesis," Clin. Cancer Res., Jan. 1, 2009; 15(1):91-99.
Park et al., "Histone deacetylases 1, 6 and 8 are critical for invasion in breast cancer," *Oncol Rep.*, Jun. 2011, 25(6):1677-1681.
Petursson et al., "Protecting Groups in Carbohydrate Chemistry," *J. Chem. Educ.*, Nov. 1997, 7(11):1297-1303.
"Physicians' Desk Reference" (PDR, e.g., 1996 edition, Medical Economics Company, Montvale, NJ), *Too Voluminous to provide*.
*Remington's Pharmaceutical Sciences*, 17th ed., Mack Publishing Company, Easton, Pa., 1985, p. 1418.
Robertson, *Protecting Group Chemistry*, (Oxford University Press, 2000); *Too Voluminous to Provide*.
Smith et al., *March's Advanced Organic Chemistry: Reactions, Mechanisms, and Structure*, 6th Ed (Wiley, 2007); *Too Voluminous to Provide*.
Vannini et al., "Crystal structure of a eukaryotic zinc-dependent histone deacetylase human HDACB. complexed with a hydroxamic acid inhibitor," PNAS, Oct. 19, 2004, 101(42):15064-15069.
Wagner et al. "Histone deacetylase (HDAC) inhibitors in recent clinical trials for cancer therapy," *Clin Epigenetics*. Dec. 2010, 1(3-4):117-136.
Witt et al., "HDAC family: What are the cancer relevant targets?" *Cancer Lett.*, May 8, 2009; 277(1):8-21.
Wu et al., "The up-regulation of histone deacetylase 8 promotes proliferation and inhibits apoptosis in hepatocellular carcinoma," *Dig Dis. Sci.* Dec. 2013, 58(12):3545-3553.
T.W. Greene and P.G.M. Wuts, *Protective Groups in Organic Synthesis*, 3rd. Ed., Wiley & Sons, Inc., New York (1999) *Too Voluminous to Provide*.
Wuts et al., *Protective Groups in Organic Synthesis*, 4th Ed., (Wiley, 2006). *Too Voluminous to Provide*.

* cited by examiner

HETEROCYCLIC COMPOUNDS AND USES THEREOF

FIELD OF THE INVENTION

This disclosure relates to compounds or ligands that modulate or inhibit histone deacetylases, and to methods of use thereof. The information provided is intended solely to assist the understanding of the reader. None of the information provided nor references cited is admitted to be prior art to the present invention. Each of the references cited is incorporated herein in its entirety and for any purpose.

BACKGROUND OF INVENTION

Histone deacetylases (HDACs) are a class of enzymes that catalyze the removal of acetyl groups from a lysine residue on both histones and non-histone proteins. The HDAC family of enzymes consists of at least 18 members, which can be subdivided into two categories: the classical HDAC family of zinc-dependent amidohydrolases, including classes I (HDACs 1, 2, 3, and 8), II (HDACs 4, 5, 6, 7, 9, and 10) and IV (HDAC 11); and the NAD$^+$-dependent class III (Sirt 1-7) sirtuin family of HDACs, which are unrelated in sequence and mechanism to classical zinc-dependent HDACs (Li et al., *Int. J. Biol. Sci.* 2014; 10(7): 757-70). HDAC8 is a unique class I HDAC family member because of its reported cytoplasmic and nuclear subcellular localization (as opposed to nuclear localization for other class I HDACs), and its ability to deacetylate non-histone proteins, such as estrogen-related receptor α (ERR-α), and cohesion SMC3 (structural maintenance of chromosome 3) (Olson et al., *Chem Biol.* 2014; 9(10):2210-6; Balasubramanian et al., *Leukemia* 2008; 22(5): 1026-34; and Deardorff et al., *Nature.* 2012; 489 (7415)).

HDACs regulate diverse cellular functions, including gene transcription, cell cycle, apoptosis, growth, differentiation and immunity (Falkenberg et al., *Nat. Rev Drug Discov.* 2014; 13(9): 673-911; and Li et al., *Int. J. Biol. Sci.* 2014; 10(7):757-70). HDACs have been found to be associated with multiple human diseases including cancer, inflammatory, immunologic, cardiovascular, and neurodegenerative disorders (Wagner et al. *Epigenetics.* 2010; 1(3-4):117-136). Deregulation of SMC3 acetylation/acetylation by HDAC8 is associated with Cornelia de Lange syndrome, an inherited congenial malformation disease in which loss of function HDAC8 mutations have recently been identified in a subset of patients (Deardorff et al., *Nature.* 2012, 13; 489 (7415)). HDAC8 is implicated in multiple human cancers including but not limited to childhood neuroblastoma (Oehme et al., Clin. Cancer Res. 2009; 15(1):91-9), breast cancer (Park at al., *Onco.l Rep.* 2011; 25(6): 1677-81), hepatocellular carcinoma (Wu et al., *Dig Dis. Sci.* 2013; 58(12): 3545-53), colon cancer (Kang et al., *Cell Death Dis.* 2014; 5: e1476), myeloproliferative neoplasms (MPNs) (Gao, et al. *Exp Hematol.* 2013; 41(3): 261-70.e4), T-cell lymphoma (Balasubramanian et al., *Leukemia* 2008; 22(5): 1026-34), and AML with inv(16)/t(16;16) (carrying CBFβ-SMMHC fusion protein) (Jing et al., *Blood* 2014: 124 (21)). HDACs have also been shown to involve in dynamic regulation of inflammatory and anti-inflammatory gene expression, and to influence the functions of various immune cells such as immunosuppressive regulatory T cells (Tregs) and antigen presenting cells (APCs) (Falkenberg et al., *Nat Rev Drug Discov.* 2014; 13(9): 673-911; and Kroesen et al., *Oncotarget.* 2014; 5(16): 6558-72). In this regard, HDAC8 has been identified to affect the expression and production of proinflammatory cytokines (e.g. IL-1β; TNFα, IL-6) (16, 17), and to regulate the expression of the MHC class I protein (Li et al., *Biochem Biophys Res Commun.* 2006; 349(4): 1315-21). Commercially available pan-HDAC inhibitors exhibit significant side effects such as bone marrow depression, diarrhea, weight loss, taste disturbances, electrolyte changes, disordered clotting, fatigue, and cardiac arrhythmias and have narrow therapeutic windows (Witt et al., *Cancer Lett.* 2009; 277(1):8-21). Accordingly, there is a need in the art for compounds that can selectively modulate the activity of HDAC for the treatment of inflammation and autoimmune diseases as well as applications in cancer immunotherapy.

SUMMARY OF INVENTION

In one aspect, the present disclosure relates to compounds having Formula (I):

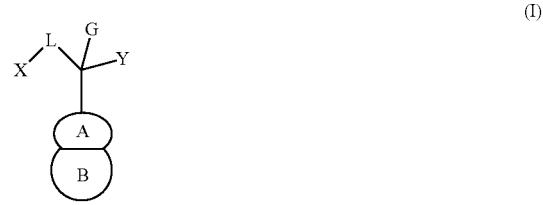

or a pharmaceutically acceptable salt a tautomer or isomer thereof, wherein constituent variables are defined herein.

In another aspact, the present disclosure provides pharmaceutical compositions comprising a compound of Formula (I), or a pharmaceutically acceptable salt, a tautomer or an isomer thereof, and at least one pharmaceutically acceptable carrier or excipient.

In another aspect, the present disclosure provides methods for modulating a histone deacetylase (HDAC). The method includes contacting the HDAC with a compound of Formula (I), or a pharmaceutically acceptable salt, a tautomer or an isomer thereof or a composition comprising compounds of Formula (I).

In another aspect, the present disclosure provides a method for treating a disease associated with abnormal activity or expression of HDACs. The method includes administering an effective amount of a compound of Formula (I), or a pharmaceutically acceptable salt, a tautomer or an isomer thereof, or a composition comprising a compound of Formula (I), to a patient in need thereof.

In yet another aspect, the present disclosure provides compounds of Formula (I) for use in treating a disease associated with abnormal activity or expression of HDACs.

In another aspect, the present disclosure provides a method for treating a disorder mediated by an HDAC, or a mutant thereof, in a patient in need thereof. The method includes administering to the patient a compound as described herein or pharmaceutically acceptable salts thereof or a composition comprising a compound as described herein.

In another aspect, the present disclosure provides the use of compounds of Formula (I) in the preparation of a medicament for use in therapy.

DETAILED DESCRIPTION

Compounds

In one aspect, the present disclosure provides a compound having Formula (I):

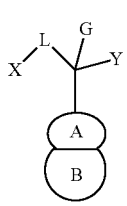

or a pharmaceutically acceptable salt, a tautomer or an isomer thereof, wherein:

(i) Y is —C(O)NHOH and ring A is fused 5- or 6-membered heteroaryl having carbon and 1-4 heteroatoms selected from O, N and S as ring members, and ring A is optionally substituted with an $R^1$ substituent;

(ii) Y is —($C_{1-4}$ alkyl)-SH and ring A is fused pyrazolyl optionally substituted with an substituent; or (iii) Y is —$(CH_2)_n$—COOH, wherein the subscript n is 0, 1, 2 or 3 and ring A is fused pyrazolyl with an $R^1$ substituent other than hydrogen;

ring B is fused phenyl, fused 5- or 6-membered heteroaryl, fused $C_{3-6}$ cycloalkyl or fused 4- to 7-membered heterocycloalkyl, wherein the fused heteroaryl or fused heterocycloalkyl each has at least one ring-forming carbon and 1-4 heteroatoms as ring members selected from O, N and S, wherein the nitrogen and sulfur atoms as ring members are each optionally oxidized, wherein ring B is optionally substituted with 1 to 4 independently selected $R^2$ substituents and wherein a carbon ring atom in ring B is optionally replaced by a carbonyl group;

wherein one of the two bridgehead atoms between ring A and ring B is optionally nitrogen;

X is $C_{6-10}$ aryl or 5- to 6-membered heteroaryl, each of which is optionally substituted with from 1-3 independently selected $R^3$ substituents;

L is $C_{1-4}$ alkylene, optionally substituted with from 1-3 $R^q$ substituents independently selected from halo. CN, OH, $C_{1-4}$ alkyl, —$OC_{1-2}$ alkyl. $C_{1-2}$ haloalkyl, and $C_{1-2}$ haloalkoxy; or two $R^q$ substituents attached to the same carbon taken together form $C_{3-6}$ cycloalkyl or 4- to 6-membered heterocycloalkyl, wherein the $C_{3-6}$ cycloalkyl and 4- to 6-membered heterocycloalkyl are each optionally substituted with 1-2 independently selected $R^r$ substituents;

G is H, CN, OH, $C_{1-4}$ alkyl, —$OC_{1-4}$ alkyl, $C_{1-4}$ haloalkyl, or $C_{1-4}$ haloalkoxy, wherein the $C_{1-4}$ alkyl, —$OC_{1-4}$ alkyl, $C_{1-4}$ haloalkyl, or $C_{1-4}$ haloalkoxy of G is optionally substituted with 1-2 substituents independently selected from halo, CN, OH, $NH_2$, $NHR^5$, $NR^5R^5$, —$C(O)NR^5R^5$, $C_{1-4}$ alkyl, —$OC_{1-2}$ alkyl, $C_{1-2}$ haloalkyl and $C_{1-2}$ haloalkoxy, wherein each $R^5$ is independently $C_{1-4}$ alkyl;

$R^1$, $R^2$ and $R^3$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^1$, $R^2$ or $R^3$ are each optionally substituted with 1, 2, 3, or 4 $R^b$ substituents independently selected from halo, $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$; wherein $C_{1-4}$ alkyl, $C_{1-4}$ haloalkyl, $C_{1-4}$ haloalkoxy $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-and (4-10 membered heterocycloalkyl)-$C_{1-4}$ alkyl- of $R^b$ are each further optionally substituted with from 1-3 $R^d$ substituents, or two adjacent $R^2$ substituents on ring B, taken together with the atoms to which they are attached, form a fused 5- or 6-membered heterocycloalkyl ring having 1-2 heteroatoms as ring members selected from N, O and S or a fused $C_{3-6}$ cycloalkyl ring, wherein the fused 5- or 6-membered heterocycloalkyl ring and fused $C_{3-6}$ cycloalkyl ring are each optionally substituted with 1 or 2 $R^b$ substituents;

or two $R^2$ substituents attached to the same carbon atom on ring B, taken together with the atom to which they are attached, form a 5- or 6-membered heterocycloalkyl ring having 1-2 heteroatoms as ring members selected from N, O and S or a $C_{3-6}$ cycloalkyl ring, wherein the 5- or 6-membered heterocycloalkyl ring and $C_{3-6}$ cycloalkyl ring are each optionally substituted with 1 or 2 $R^b$ substituents:

or two adjacent $R^3$ substituents on the $C_{6-10}$ aryl of X, taken together with the atoms to which they are attached, form fused $C_{3-6}$cycloalkyl, or fused 5- or 6-membered heterocycloalkyl;

or two adjacent $R^3$ substituents on the 5- to 6-membered heteroaryl of X, taken together with the atoms to which they are attached, form fused phenyl, fused $C_{3-6}$ cycloalkyl, fused 5- or 6-membered heteroaryl or fused 5- or 6-membered heterocycloalkyl, wherein the fused 5- or 6-membered heteroaryl or fused 5- or 6-membered heterocycloalkyl has 1-2 heteroatoms as ring members selected from N, O and S; and wherein fused phenyl, fused. $C_{3-6}$ cycloalkyl, fused 5- or 6-membered heteroaryl and fused 5- or 6-membered heterocycloalkyl are each optionally substituted with 1 or 2 $R^b$ substituents;

each $R^a$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^a$ are each optionally substituted with 1, 2, 3, 4, or 5 substituents independently selected from $C_{1-4}$ alkyl, $C_{1-4}$ haloalkyl, halo, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, wherein the aliphatic or aromatic portion of $R^d$ is further optionally substituted with 1-3 independently selected $R^r$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 $R^f$ substituents independently selected from $C_{1-4}$ alkyl, haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, and $S(O)NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 $R^n$ substituents independently selected from $C_{1-4}$ alkyl, $C_{1-4}$ haloalkyl, halo, CN, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR^o)NR^oR^o$, $NR^oC(=NR^o)NR^oR^o$, $S(O)R^o$, $S(O)NR^oR^o$, $S(O)_2R^o$, $NR^oS(O)_2R^o$, $NR^oS(O)_2NR^oR^o$, and $S(O)_2NR^oR^o$;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with from 1-3 $R^p$ substituents;

or any two $R^a$ substituents together with the nitrogen atom to which they are attached form a 4-, 5-, 6-, 7-, 8-, 9- or 10-membered heterocycloalkyl group optionally substituted with 1, 2 or 3 $R^h$ substituents independently selected from $C_{1-6}$ alkyl, $C_{3-10}$ cycloalkyl, 4-7 membered heterocycloalkyl, $C_{6-10}$ aryl, 5-6 membered heteroaryl, $C_{1-6}$ haloalkyl, $C_{2-6}$ alkenyl, $C_{2-6}$ alkynyl, halo, CN, $OR^i$, $SR^i$, $NHOR^i$, $C(O)R^i$, $C(O)NR^iR^i$, $C(O)OR^i$, $OC(O)R^i$, $OC(O)NR^iR^i$, $NHR^i$, $NR^iR^i$, $NR^iC(O)R^i$, $NR^iC(O)NR^iR^i$, $NR^iC(O)OR^i$, $C(=NR^i)NR^iR^i$, $NR^iC(=NR^i)NR^iR^i$, $S(O)R^i$, $S(O)NR^iR^i$, $S(O)_2R^i$, $NR^iS(O)_2R^i$, $NR^iS(O)_2R^iR^i$, and $S(O)_2NR^iR^i$, wherein the $C_{1-6}$ alkyl, $C_{3-10}$ cycloalkyl, 4-7 membered heterocycloalkyl, $C_{6-10}$ aryl, and 5-6 membered heteroaryl of $R^h$ are each further optionally substituted by 1, 2, or 3 $R^i$ substituents independently selected from $C_{3-6}$ cycloalkyl, $C_{6-10}$ aryl, 5 or 6-membered heteroaryl, $C_{2-4}$ alkenyl, $C_{2-4}$ alkynyl, halo, $C_{1-4}$ alkyl, $C_{1-4}$ haloalkyl, CN, $NHOR^k$, $OR^k$, $SR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $NR^kC(O)NR^kR^k$, $NR^kC(O)OR^k$, $C(=NR^k)NR^kR^k$, $NR^kC(=NR^k)NR^kR^k$, $S(O)R^k$, $S(O)NR^kR^k$, $S(O)_2R^k$, $NR^kS(O)_2R^k$, $NR^kS(O)_2NR^kR^k$, and $S(O)_2NR^kR^k$; or two $R^h$ groups attached to the same carbon atom of the 4- to 10-membered heterocycloalkyl taken together with the carbon atom to which they attach form a $C_{3-6}$cycloalkyl or 4- to 6-membered heterocycloalkyl having 1-2 heteroatoms as ring members selected from O, N or S;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

or any two $R^e$ substituents together with the nitrogen atom to which they are attached form a 4-, 5-, 6-, or 7-membered heterocycloalkyl group optionally substituted with 1, 2, or 3 independently selected $R^h$ substituents;

or any two $R^g$ substituents together with the nitrogen atom to which they are attached form a 4-, 5-, 6-, or 7-membered heterocycloalkyl group optionally substituted with 1, 2, or 3 independently selected $R^h$ substituents;

or any two $R^i$ substituents together with the nitrogen atom to which they are attached form a 4-, 5-, 6-, or 7-membered heterocycloalkyl group optionally substituted with 1, 2, or 3 independently selected $R^h$ substituents;

or any two $R^k$ substituents together with the nitrogen atom to which they are attached form a 4-, 5-, 6-, or 7-membered heterocycloalkyl group optionally substituted with 1, 2, or 3 independently selected $R^h$ substituents;

or any two $R^o$ substituents together with the nitrogen atom to which they are attached form a 4-, 5-, 6-, or 7-membered heterocycloalkyl group optionally substituted with 1, 2, or 3 independently selected $R^h$ substituents; and each $R^e$, $R^i$, $R^k$, $R^o$ or $R^p$ is independently selected from H, $C_{1-4}$ alkyl, $C_{3-6}$ cycloalkyl, $C_{6-10}$ aryl, 5 or 6-membered heteroaryl, $C_{1-4}$ haloalkyl, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, $C_{2-4}$ alkenyl, and $C_{2-4}$ alkynyl of $R^e$, $R^i$, $R^k$, $R^o$ or $R^p$ are each optionally substituted with 1, 2 or 3 $R^r$ substituents independently selected from OH, CN, amino, halo, $C_{1-4}$ alkyl, $C_{1-4}$ alkoxy, $C_{1-4}$ alkylthio, $NHR^6$, $NR^6R^6$, $C_{1-4}$ haloalkyl, and $C_{1-4}$ haloalkoxy, wherein each $R^6$ is independently H or $C_{1-6}$ alkyl.

In some embodiments, Y is —C(O)NHOH and ring A is fused 5- or 6-membered heteroaryl having carbon and 1-4 heteroatoms selected from O, N and S as ring members, and ring A is optionally substituted with an $R^1$ substituent.

In some embodiments: Y is —($C_{1-4}$ alkyl)-SH and ring A is fused pyrazolyl optionally substituted with an $R^1$ substituent.

In some embodiments, Y is —$(CH_2)_n$—COOH, wherein the subscript n is 0, 1, 2 or 3 and ring A is fused pyrazolyl with an $R^1$ substituent other than hydrogen.

In some embodiments:

Y is —C(O)NHOH and ring A is fused pyrrolyl, fused pyrazolyl, fused imidazolyl or fused triazolyl, each optionally substituted with an $R^1$ substituent;

ring B is fused phenyl, fused pyridyl, fused pyrimidinyl, fused pyrazinyl, fused pyridazinyl, fused triazinyl or fused cyclohexyl, each of which is optionally substituted with 1 to 4 independently selected $R^2$ substituents; and one of the two bridgehead atoms between ring A and ring B is optionally nitrogen.

In some embodiments:

Y is —C(O)NHOH and ring A is fused fused pyrazolyl optionally substituted with an $R^1$ substituent;

ring B is fused phenyl, fused pyridyl, fused pyrimidinyl, fused pyrazinyl, fused pyridazinyl, fused triazinyl or fused cyclohexyl, each of which is optionally substituted with 1 to 4 independently selected $R^2$ substituents; and one of the two bridgehead atoms between ring A and ring B is optionally nitrogen.

In some embodiments, the moiety:

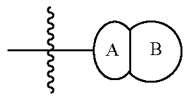

in formula (I) is selected from:

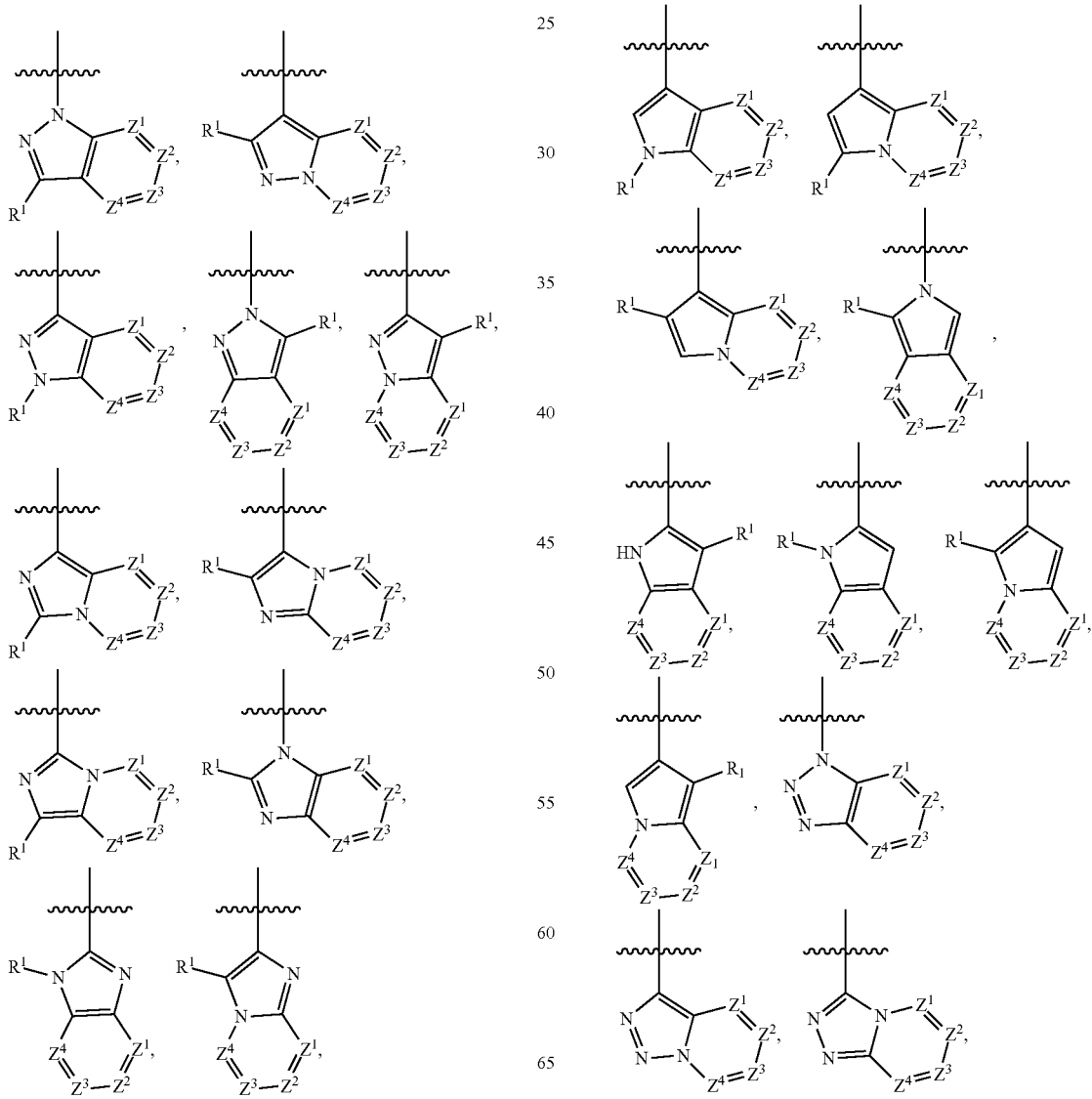

-continued

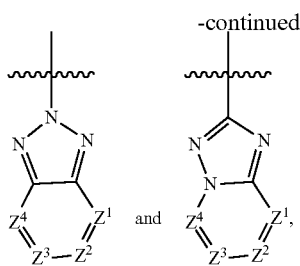

wherein $Z^1$, $Z^2$, $Z^3$ and $Z^4$ are each independently N or $CR^2$ with the proviso that at least two of $Z^1$, $Z^2$, $Z^3$ and $Z^4$ are $CR^2$ and the wavy line indicates the point of attachment to the rest of the molecule.

In some embodiments, $Z^1$, $Z^2$, $Z^3$ and $Z^4$ are each independently $CR^2$.

In some embodiments, one or two of $Z^1$, $Z^2$, $Z^3$ and $Z^4$ are N and the others are each independently $CR^2$.

In some embodiments, ring B is fused cyclohexyl optionally substituted with 1-4 independently selected $R^2$ substituents.

In some embodiments, X is $C_{6-10}$ aryl, optionally substituted with 1-3 independently selected $R^3$ substituents.

In some embodiments, X is phenyl, optionally substituted with 1-3 independently selected $R^3$ substituents.

In some embodiments, X is phenyl.

In some embodiments, L is $CH_2$, optionally substituted with 1-3 independently selected $R^q$ substituents.

In some embodiments, L is $CH_2$.

In some embodiments, G is H.

In some embodiments, Y is —C(O)NHOH.

In some embodiments, $R^1$ is H, halo or $C_{2-6}$ alkynyl, wherein the $C_{2-6}$ alkynyl is optionally substituted with $C_{3-6}$ cycloalkyl, 4 to 6-membered heterocycloalkyl, phenyl or 5- or 6-membered heteroaryl, each of which is optionally substituted with 1-3 independently selected $R^b$ substituents.

In some embodiments, $R^1$ is H, halo, or 2-cyclopropyl-ethynyl optionally substituted with 1-3 independently selected $R^b$ substituents.

In some embodiments, $R^2$ is H, halo, $C^{1-6}$ alkyl, phenyl, 5- or 6-membered heteroaryl, $C_{3-6}$ cycloalkyl, 4 to 6-membered heterocycloalkyl, 4 to 6-membered heterocycloalkyl-$C_{1-4}$alkyl, 5- or 6-membered heteroaryl-$C_{1-4}$alkyl, $C_{3-6}$cycloalkyl-$C_{1-4}$alkyl, —C(O)$R^a$, —C(O)NHR$^a$ or —OR$^a$, wherein each $R^a$ is independently selected from $C_{1-6}$ alkyl, 4 to 6-membered heterocycloalkyl, 4 to 6-membered heterocycloalkyl-$C_{1-4}$alkyl, $C_{3-6}$ cycloalkyl, $C_{3-6}$ cycloalkyl-$C_{1-4}$ alkyl. 5- to 10-membered heteroaryl and 5- to 10-membered heteroaryl-$C_{1-4}$alkyl, each of which is optionally substituted with 1-3 independently selected $R^d$ substituents; and wherein $C_{1-6}$ alkyl, phenyl, 5- or 6-membered heteroaryl, $C_{3-6}$ cycloalkyl, 4 to 6-membered heterocycloalkyl, 4 to 6-membered heterocycloalkyl-$C_{1-4}$ alkyl, 5- or 6-membered heteroaryl-$C_{1-4}$ alkyl, and $C_{3-6}$ cycloalkyl-$C_{1-4}$ alkyl of $R^2$ are each optionally substituted with 1-3 independently selected $R^b$ groups.

In some embodiments, $R^b$ is halo, CN, $C_{1-6}$ alkyl, —OR$^c$, —C(O)NR$^c$R$^c$, R$^e$O—C$_{1-6}$alkyl-, NHR$^c$ or 4- to 10-membered heterocycloalkyl optionally substituted with 1-2 independently selected $R^d$ substituents.

In some embodiments, $R^2$ is H, F, Cl, Br, I, $C_{1-4}$ alkyl, phenyl, 2-pyridyl, 3-pyridyl, 4-pyridyl, 5-pyrimidinyl, 2-pyrimidinyl, 4-pyrimidinyl, 1-pyrazolyl, 3-pyrazolyl, 4-pyrazolyl, 1-piperidinyl, 4-piperidinyl, 4-morpholinyl, 1-piperazinyl, 2-tetrahydrofuranyl, 3-tetrahydrofuranyl, 2-tetrahydro-2H-pyranyl, 3-tetrahydropyranyl, 4-tetrahydropyranyl, 7-azaspiro[3.5]nonan-7-yl, 2-oxa-7-azaspiro[3.5]nonan-7-yl, 8-azaspiro[4.5]decan-8-yl, 3-azaspiro[5.5]undecan-3-yl, 3-oxa-9-azaspiro[5.5]undecan-9-yl, cyclopropyl, cyclobutyl, cyclopentyl, cyclohexyl, —C(O)R$^a$, —C(O)NHR$^a$, or —CH$_2$R$^b$, wherein R$^a$ and R$^b$ are each independently selected from 1-piperidinyl, 4-piperidinyl, 4-morpholinyl, 1-piperazinyl, 2-tetrahydrofuranyl, 3-tetrahydrofuranyl, 2-tetrahydropyranyl, 3-tetrahydropyranyl, 4-tetrahydropyranyl, 7-azaspiro[3.5]nonan-7-yl, 2-oxa-7-azaspiro[3.5]nonan-7-yl, 8-azaspiro[4.5]decan-8-yl, 3-azaspiro[5.5]undecan-3-yl, 3-oxa-9-azaspiro[5.5]undecan-9-yl, cyclopropyl, cyclobutyl, cyclopentyl, cyclohexyl, cyclopropyl-$C_{1-2}$ alkyl, cyclobutyl-$C_{1-2}$ alkyl, cyclopentyl-$C_{1-2}$ alkyl, cyclohexyl-$C_{1-2}$ alkyl, 4-morpholinyl-$C_{1-2}$ alkyl, and 4-tetrahydropyranyl-$C_{1-2}$ alkyl.

In some embodiments, $R^3$ is selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, and S(O)$_2$NR$^a$R$^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^3$ are each optionally substituted with 1, 2, 3, or 4 $R^b$ substituents independently selected from halo, $C_{1-4}$ alkyl, $C_{1-4}$ haloalkyl, haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$alkyl-, CN, NH$_2$, NO$_2$, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$; wherein $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$alkyl-, (5-10 membered heteroaryl)-$C_{1-4}$alkyl-and (4-10 membered heterocycloalkyl)-$C_{1-4}$alkyl- of $R^b$ are each further optionally substituted with from 1-3 $R^d$ substituents.

In some embodiments. $R^3$ is H.

In some embodiments, the compounds of the invention have Formula (II):

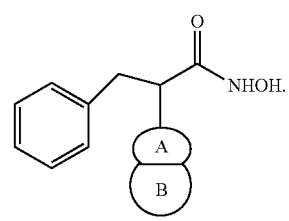

(II)

In some embodiments, wherein the compound has Formula (II) the moiety:

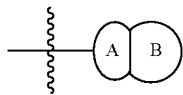

is:

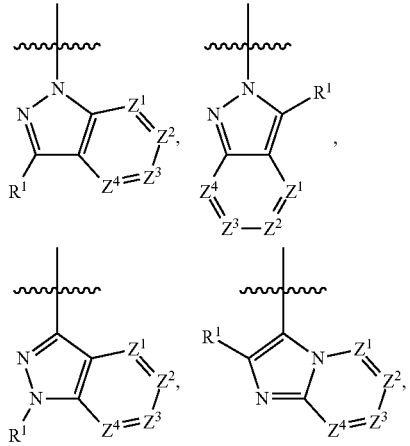

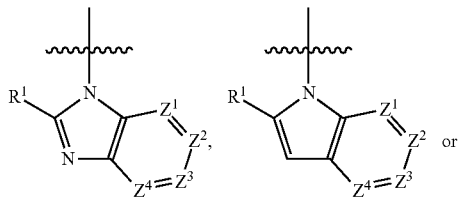

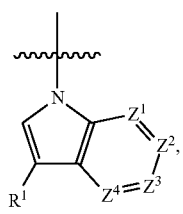

wherein $Z^1$, $Z^2$, $Z^3$ and $Z^4$ are each independently N or $CR^2$ with the proviso that at least two of $Z^1$, $Z^2$, $Z^3$ and $Z^4$ are $CR^2$ and the wavy line indicates the point of attachment to the rest of the molecule. In some embodiments, $Z^1$, $Z^2$, $Z^3$ and $Z^4$ are each independently $CR^2$. In other embodiments, $Z^1$ is N and $Z^1$, $Z^3$ and $Z^4$ are each independently $CR^2$. In other embodiments, $Z^2$ is N and $Z^1$, $Z^3$ and $Z^4$ are each independently $CR^2$. In other embodiments, $Z^3$ is N and $Z^2$, $Z^1$ and $Z^4$ are each independently $CR^2$. In other embodiments, $Z^4$ is N and $Z^2$, $Z^3$ and $Z^1$ are each independently $CR^2$. In some embodiments, $R^1$ is H or cyclopropylethynyl.

In some embodiments, the disclosure provides compounds of Formula (IIa) or (IIb):

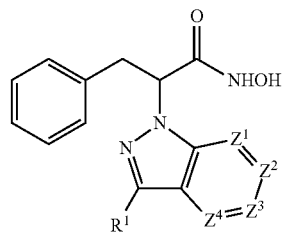

(IIa)

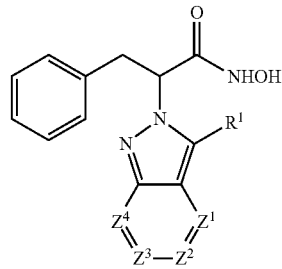

(IIb)

where $R^1$, $Z^1$, $Z^2$, $Z^3$ and $Z^4$ are as defined in any of the embodiments of compounds of Formula (I) or (II) as described herein.

In some embodiments, where the compounds of the invention have Formula (II), the moiety:

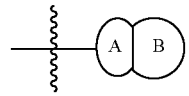

is:

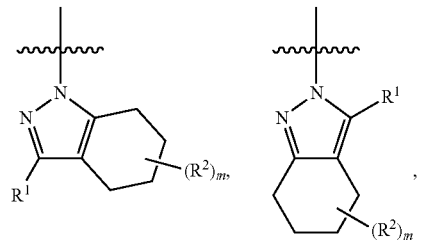

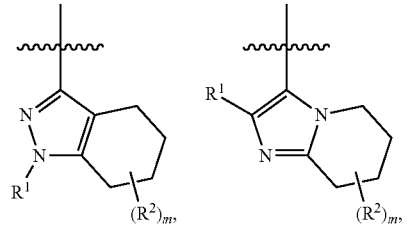

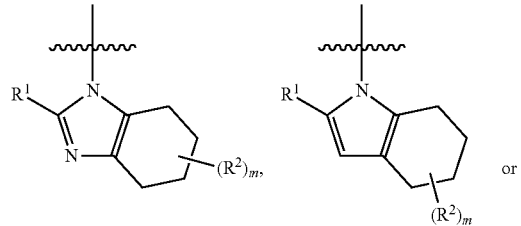

-continued

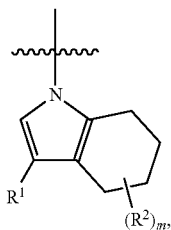

wherein the subscript m is 1, 2, 3 or 4 and the wavy line indicates the point of attachment to the rest of the molecule.

In some embodiments of compounds of Formula (I) or (II), the moiety:

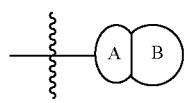

is

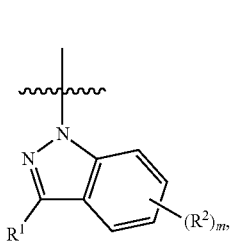 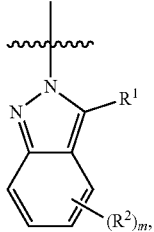

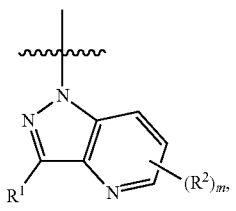 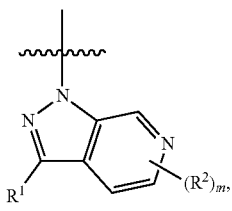

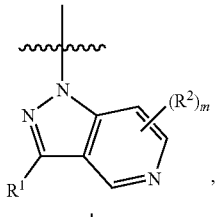 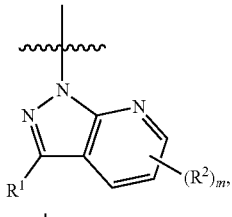

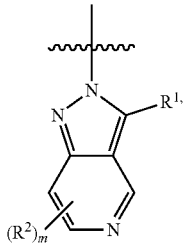 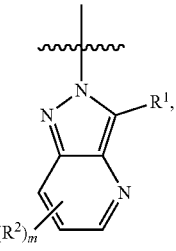

-continued

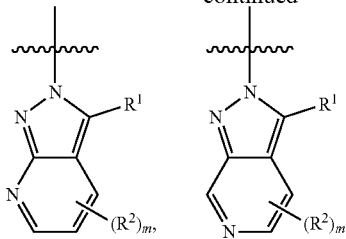

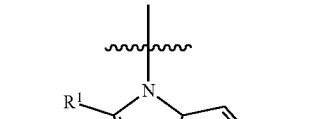

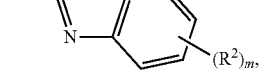

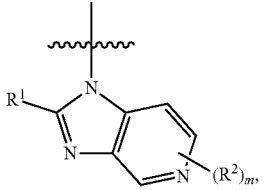 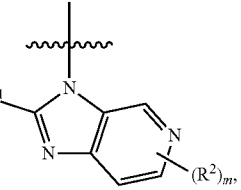

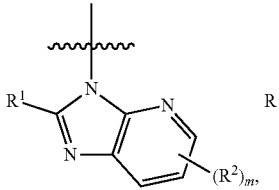

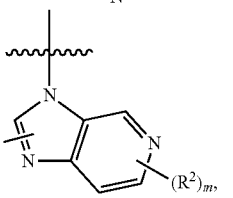

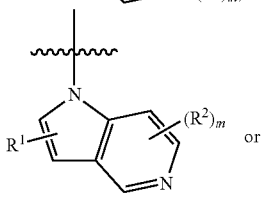

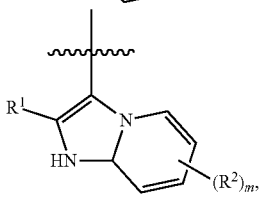

where the substituents $R^1$, $R^2$ and m are as defined herein. In some embodiments, $R^1$ is H, halo or $C_{2-6}$ alkynyl, wherein the $C_{2-6}$ alkynyl is optionally substituted with $C_{3-6}$ cycloalkyl, 4 to 6-membered heterocycloalkyl, phenyl or 5- or 6-membered heteroaryl, each of which is optionally substituted with 1-3 independently selected $R^b$ substituents. In other embodiments, $R^1$ is H, halo, or 2-cyclopropylethynyl optionally substituted with 1-3 independently selected $R^b$ substituents. In some embodiments, $R^2$ is H, halo, $C_{1-6}$ alkyl, phenyl, 5- or 6-membered heteroaryl, $C_{3-6}$ cycloalkyl, 4 to 6-membered heterocycloalkyl, 4 to 6-membered heterocycloalkyl-$C_{1-4}$alkyl, 5- or 6-membered heteroaryl-$C_{1-}$ ₄alkyl, C₃₋₆cycloalkyl-C₁₋₄alkyl, —C(O)R$^a$, —C(O)NHR$^a$ or —OR$^a$, wherein each R$^a$ is independently selected from C₁₋₆ alkyl, 4 to 6-membered heterocycloalkyl, 4 to 6-membered heterocycloalkyl-C₁₋₄alkyl, C₃₋₆ cycloalkyl, C₃₋₆ cycloalkyl-C₁₋₄ alkyl, 5- to 10-membered heteroaryl and 5- to 10-membered heteroaryl-C₁₋₄alkyl, each of which is optionally substituted with 1-3 independently selected R$^d$ substituents; and wherein C₁₋₆ alkyl, phenyl, 5- or 6-membered heteroaryl, C₃₋₆ cycloalkyl, 4 to 6-membered heterocycloalkyl, 4 to 6-membered heterocycloalkyl-C₁₋₄ alkyl, 5- or 6-membered heteroaryl-C₁₋₄ alkyl, and C₃₋₆ cycloalkyl-C₁₋₄ alkyl of R² are each optionally substituted with 1-3 independently selected R$^b$ groups. In certain instances, R$^b$ is halo, CN, C₁₋₆ alkyl, —OR, —C(O)NR$^c$R$^c$, R$^e$O—C₁₋₆alkyl-, NHR$^c$ or 4- to 10-membered heterocycloalkyl optionally substituted with 1-2 independently selected R$^d$ substituents. In other embodiments, R² is H, F, Cl, Br, I, C₁₋₄ alkyl, phenyl, 2-pyridyl, 3-pyridyl, 4-pyridyl, 5-pyrimidinyl, 2-pyrimidinyl, 4-pyrimidinyl, 1-pyrazolyl, 3-pyrazolyl, 4-pyrazolyl, 1-piperidinyl, 4-piperidinyl, 4-morpholinyl, 1-piperazinyl, 2-tetrahydrofuranyl, 3-tetrahydrofuranyl, 2-tetrahydro-2H-pyranyl, 3-tetrahydropyranyl, 4-tetrahydropyranyl, 7-azaspiro[3.5]nonan-7-yl, 2-oxa-7-azaspiro[3.5]nonan-7-yl, 8-azaspiro[4.5]decan-8-yl, 3-azaspiro[5.5]undecan-3-yl, 3-oxa-9-azaspiro[5.5]undecan-9-yl, cyclopropyl, cyclobutyl, cyclopentyl, cyclohexyl, —C(O)R$^a$, —C(O)NHR$^a$, or —CH₂R$^b$, wherein R$^a$ and R$^b$ are each independently selected from 1-piperidinyl, 4-piperidinyl, 4-morpholinyl, 1-piperazinyl, 2-tetrahydrofuranyl, 3-tetrahydrofuranyl, 2-tetrahydropyranyl, 3-tetrahydropyranyl, 4-tetrahydropyranyl, 7-azaspiro[3.5]nonan-7-yl, 2-oxa-7-azaspiro[3.5]nonan-7-yl, 8-azaspiro[4,5]decan-8-yl, 3-azaspiro[5,5]undecan-3-yl, 3-oxa-9-azaspiro[5,5]undecan-9-yl, cyclopropyl, cyclobutyl, cyclopentyl, cyclohexyl, cyclopropyl-C₁₋₂alkyl, cyclobutyl-C₁₋₂alkyl, cyclopentyl-C₁₋₂alkyl, cyclohexyl-C₁₋₂alkyl, 4-morpholinyl-C₁₋₂alkyl, and 4-tetrahydropyranyl-C₁₋₂alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Definitions

At various places in the present specification, substituents of compounds of the invention are disclosed in groups or in ranges. It is specifically intended that the invention include each and every individual subcombination of the members of such groups and ranges. For example, the term "C₁₋₆ alkyl" is specifically intended to individually disclose methyl, ethyl, C₃ alkyl, C₄ alkyl, C₅ alkyl, and C₆ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

As used herein, the term "substituted" means that a hydrogen atom is replaced by a non-hydrogen group. It is to be understood that substitution at a given atom is limited by valency.

As used herein, the term "C$_{i\text{-}j}$" where i and j are integers, employed in combination with a chemical group, designates a range of the number of carbon atoms in the chemical group with i-j defining the range. For example, C₁₋₆ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched. In some embodiments, the alkyl group contains 1 to 6, 1 to 4, or 1 to 3 carbon atoms. Examples of alkyl moieties include, but are not limited to, chemical groups such as methyl, ethyl, n-propyl, n-butyl, isobutyl, sec-butyl, ten-butyl, n-pentyl, 2-methyl-1-butyl, 3-pentyl, n-hexyl, 1,2,2-trimethylpropyl, and the like. In some embodiments, the alkyl group is methyl, ethyl, or propyl.

As used herein, "alkenyl," employed alone or in combination with other terms, refers to an alkyl group having one or more carbon-carbon double bonds. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkynyl," employed alone or in combination with other terms, refers to an alkyl group having one or more carbon-carbon triple bonds. In some embodiments, the alkynyl moiety contains 2 to 6 or 2 to 4 carbon atoms. Example alkynyl groups include, but are not limited to, ethynyl, propyn-2-yl, and the like.

As used herein, "halo" or "halogen", employed alone or in combination with other terms, includes fluoro, chloro, bromo, and iodo. In some embodiments, halo is F or Cl. In some embodiments, halo is F.

As used herein, the term "haloalkyl," employed alone or in combination with other terms, refers to an alkyl group having up to the full valency of halogen atom substituents, which may either be the same or different. In some embodiments, the halogen atoms are fluoro atoms. In some embodiments, the alkyl group has 1 to 6, 1 to 4, or 1 to 3 carbon atoms. Example haloalkyl groups include CF₃, C₂F₅, CHF₂, CCl₃, CHCl₂, C₂Cl₅, and the like.

As used herein, the term "alkoxy," employed alone or in combination with other terms, refers to a group of formula —O-alkyl. In some embodiments, the alkyl group has 1 to 6, 1 to 4, or 1 to 3 carbon atoms. Example alkoxy groups include methoxy, ethoxy, propoxy (e.g., n-propoxy and isopropoxy), t-butoxy, and the like. In some embodiments, alkoxy is methoxy.

As used herein, "haloalkoxy," employed alone or in combination with other terms, refers to a group of formula —O-(haloalkyl). In some embodiments, the alkyl group has 1 to 6, 1 to 4, or 1 to 3 carbon atoms. An example haloalkoxy group is —OCF₃.

As used herein, "amino," employed alone or in combination with other terms, refers to NH₂.

As used herein, the term "alkylamino," employed alone or in combination with other terms, refers to a group of formula —NH(alkyl). In some embodiments, the alkylamino group has 1 to 6 or 1 to 4 carbon atoms. Example alkylamino groups include methylamino, ethylamino, propylamino (e.g., n-propylamino and isopropylamino), and the like.

As used herein, the term "dialkylamino," employed alone or in combination with other terms, refers to a group of formula —N(alkyl)$_2$. Example dialkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "alkylthio," employed alone or in combination with other terms, refers to a group of formula —S-alkyl. In some embodiments, the alkyl group has 1 to 6 or 1 to 4 carbon atoms.

As used herein, the term "cycloalkyl," employed alone or in combination with other terms, refers to a non-aromatic cyclic hydrocarbon including cyclized alkyl and alkenyl groups. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5]octane and the like). In some embodiments, the cycloalkyl group has 3 to 10 ring members, or 3 to 7 ring members, or 3 to 6 ring members. In some embodiments, the cycloalkyl group is monocyclic or bicyclic. In some embodiments, the cycloalkyl group is monocyclic. In some embodiments, the cycloalkyl group is a $C_{3-7}$ or a $C_{3-6}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "$C_{i-j}$ cycloalkyl-$C_{i-j}$ alkyl," employed alone or in combination with other terms, refers to an alkyl group substituted by a cycloalkyl group. An example of a $C_{i-j}$ cycloalkyl-$C_{i-j}$ alkyl group is cyclopropylmethyl.

As used herein, the term "heterocycloalkyl," employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-diexa-8-aza-spiro[4.5]decan-N-yl] and the like). In some embodiments, the heterocycloalkyl group has 3 to 10 ring-forming atoms, 4 to 10 ring-forming atoms, 4 to 7 ring-forming atoms, or 3 to 8 ring forming atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group. In some embodiments, the heterocycloalkyl group is a morpholine ring, pyrrolidine ring, piperazine ring, piperidine ring, dihydropyran ring, tetrahydropyran ring, tetrahyropyridine, azetidine ring, or tetrahydrofuran ring. In certain embodiments, the heterocycloalkyl group is a monocyclic or bicyclic non-aromatic ring or ring system having 4 to 10 ring-forming atoms, wherein 1 to 4 ring-forming atoms are heteroatoms independently selected from N, O, and S, wherein the N and S as ring members are each optionally oxidized, the carbon ring members may be optionally replaced by carbonyl, and the heterocycloalkyl group can be optionally fused to a 5-6 membered heteroaryl or phenyl ring. In another preferred embodiment, the heterocyloalkyl group is a monocyclic non-aromatic ring or ring system having 4 to 7 ring-forming atoms, wherein 1 to 3 ring-forming atoms are heteroatoms independently selected from N, O, and S, wherein the N and S as ring members are each optionally oxidized, the carbon ring members may be optionally replaced by carbonyl, and the heterocycloalkyl group can be optionally fused to a 5-6 membered heteroaryl or phenyl ring.

As used herein, the term "heterocycloalkyl-$C_{i-j}$ alkyl," employed alone or in combination with other terms, refers to an alkyl group substituted by a heterocycloalkyl group. An example of a heterocycloalkyl-$C_{i-j}$ alkyl group is pyrrolidinylmethyl.

As used herein, the term "aryl" employed alone or in combination with other terms, refers to a monocyclic or polycyclic (e.g., having 2 fused rings) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl.

As used herein, the term "aryl-$C_{i-j}$ alkyl," employed alone or in combination with other terms, refers to an alkyl group substituted by an aryl group. An example of an aryl-$C_{i-j}$ alkyl group is benzyl.

As used herein, the term "heteroaryl," employed alone or in combination with other terms, refers to a monocyclic or polycyclic (e.g., having 2 or 3 fused rings) aromatic hydrocarbon moiety, having one or more heteroatom ring members independently selected from nitrogen, sulfur and oxygen. In some embodiments, the heteroaryl group is a monocyclic or bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b]thiazolyl or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In one embodiment the heteroaryl group is a 5 to 10 membered heteroaryl group. In another embodiment the heteroaryl group is a 5 to 6 membered heteroaryl group. In certain embodiments, the heteroaryl group is a monocyclic or bicyclic aromatic ring system having 5 to 10 ring-forming atoms, wherein 1 to 4 ring-forming atoms are heteroatoms independently selected from N, O, and S, wherein the N and S as ring members are each optionally oxidized, the carbon ring members may be optionally replaced by carbonyl. In another preferred embodiment, the heteroaryl group is a monocyclic aromatic ring system having 5 to 6 ring-forming atoms, wherein 1 to 4 ring-forming atoms are heteroatoms independently selected from N, O, and S, wherein the N and S as ring members are each optionally oxidized, the carbon ring members may be optionally replaced by carbonyl.

As used herein, the term "heteroaryl-$C_{i-j}$ alkyl," employed alone or in combination with other terms, refers to an alkyl group substituted by a heteroaryl group. An example of a heteroaryl-$C_{i-j}$ alkyl group is pyridylmethyl.

When two alkyl groups are shown attached to a nitrogen atom on a substituent group (e.g., $N(C_{1-4}$ alkyl)$_2$), it is intended that each alkyl group be selected independently from the other. For example, each group can be different (e.g., one alkyl group can be methyl and the other ethyl); alternatively, both groups can be the same (e.g., ethyl).

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers, and isotopes of the structures depicted. The term "isomer", as used herein, refers to a stereoisomer of the compound, such as an enantiomer, racemate, rotamer, conformer, diastereomer, or optical isomer of the compound.

All compounds, and pharmaceutically acceptable salts thereof, can be found together with other substances such as water and solvents (e.g., in the form of hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The following abbreviations may be used herein: AcOH (acetic acid); Ac$_2$O (acetic anhydride); aq, (aqueous); atm. (atmosphere(s)); Boc (t-butoxycarbonyl); hr (broad); Cbz (carboxybenzyl); calc. (calculated); d (doublet); dd (doublet of doublets); DCM (dichloromethane); DEAD (diethyl azodicarboxylate); DIAD (N,N'-diisopropyl azodicarboxylate); DIPEA (N,N'-diisopropylethylamine); DMF (N,N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography-mass spectrometry); m (multiplet); M (molar); mCPBA (3-chloroperoxybenzoic acid); MgSO$_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaHCO$_3$ (sodium bicarbonate); NaOH (sodium hydroxide); Na$_2$SO$_4$ (sodium sulfate); NH$_4$Cl (ammonium chloride); NH$_4$OH (ammonium hydroxide); nM (nanomolar); NMR (nuclear magnetic resonance spectroscopy); OTf (trifluoromethanesulfonate); Pd (palladium); Ph (phenyl); pM (picomolar); PMB (para-methoxybenzyl); POCl$_3$ (phosphoryl chloride); RP-HPLC (reverse phase high performance liquid chromatography); s (singlet); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); µg (microgram(s)); µL (microliter(s)); µM (micromolar); wt % (weight percent).

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the HDACs such as HDAC8 with a compound of the invention includes the administration of a compound of the present invention to an individual or patient, such as a human, having HDACs such as HDAC8, as well as, for example, introducing a compound of the invention into a sample containing a cellular or purified preparation containing the HDAC enzymes such as HDAC8.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) preventing the disease; for example, preventing a disease, condition or disorder in an individual who may be predisposed to the disease, condition or disorder but does not yet experience or display the pathology or symptomatology of the disease; 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "modulating" or "modulate" refers to an effect of altering a biological activity, especially a biological activity associated with a biomolecule such as an HDAC enzyme by interacting with the biomolecule, for example, an increase or decrease in the amount, quality, response or effect of a particular biological activity or function of a biomolecule, such as an HDAC enzyme.

As used herein, the term "inhibit(s)" or "inhibiting" refers to any quantitative or qualitative reduction in biological activity or binding of a biomolecule such as an HDAC enzyme. As used herein, the term "inhibitor" refers to a compound that binds to and/or inhibits an HDAC enzyme with measurable affinity. In certain embodiments, an inhibitor has an IC$_{50}$ and/or binding constant of less about 50 µM, less than about 1 µM, less than about 500 nM, less than about 100 nM, less than about 10 nM, or less than about 1 nM.

Synthesis

Compounds of the invention, including salts thereof, can be prepared using known organic synthesis techniques and according to various possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvents freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography.

The expressions, "ambient temperature", "room temperature", and "r.t.", as used herein, are understood in the art, and refer generally to a temperature, e.g. a reaction temperature, that is about the temperature of the room in which the reaction is carried out, for example, a temperature from about 20° C. to about 30° C.

Compounds as disclosed herein can be prepared by one skilled in the art according to preparatory routes known in the literature. Example synthetic methods for preparing compounds of the invention are provided in the Schemes below.

A series of hydroxamic acid derivatives of formula 4 can be prepared using the process illustrated in Scheme 1. Treating compound 1 with sodium hydride followed by compound 2 provides compound 3 which can be converted to the corresponding hydroxamic acid derivatives of formula 4 by treating with hydroxylamine.

Scheme 1

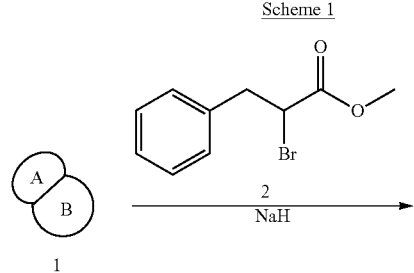

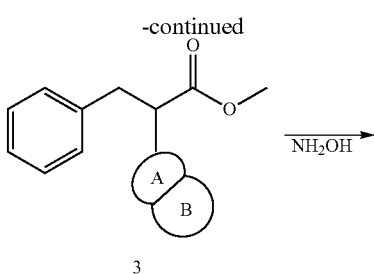

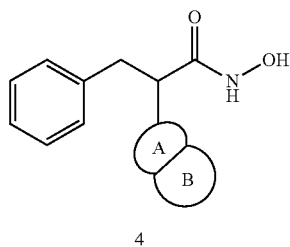

A series of hydroxamic acid derivatives of formula 10 and formula 11 can be prepared by the methods illustrated in Scheme 2. Treating compound 5 ($X^1$ is Cl or Br) with sodium hydride followed by compound 2 yields a mixture of compound 6 and compound 7 which can be separated via chromatography. The isolated compound 6 and compound 7 can then be converted to the corresponding compound 8 and compound 9 using Suzuki-coupling or Buchwald-coupling. Subsequently, compound 8 and compound 9 can be converted to the corresponding hydroxamic acid derivatives of formula 10 and formula 11 by treating with hydroxylamine.

Scheme 2

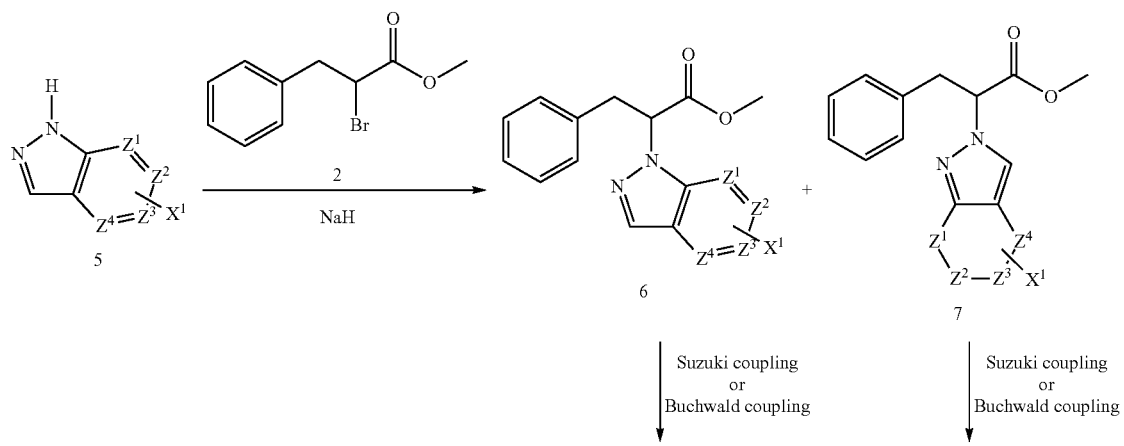

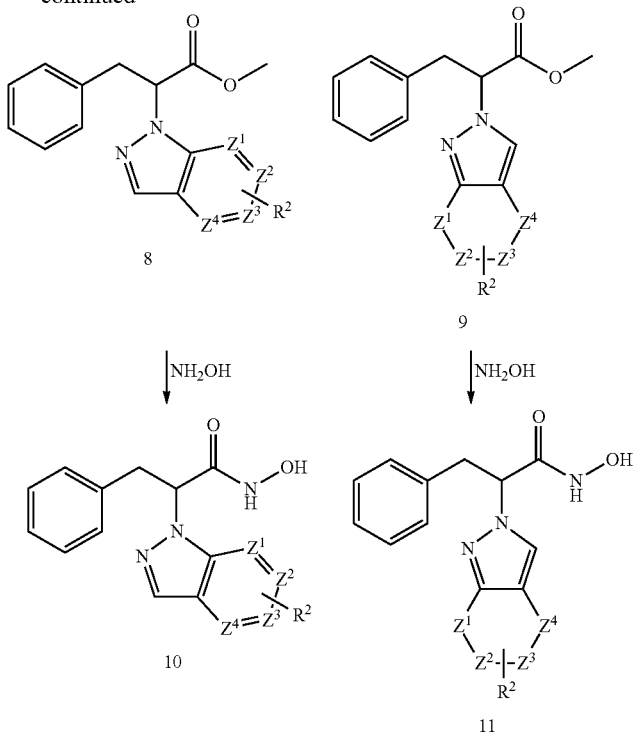

A series of hydroxamic acid derivatives of formula 18 can be prepared via the route illustrated in Scheme 3. Treating compound 12 with cesium carbonate and benzyl bromide yields compound 13 (Bn is benzyl). Treating compound 13 with KHMDS followed by compound 2 gives compound 14. The benzyl group of compound 14 can be cleaved via hydrogenolysis over Pd/C to provide compound 15 which can be subsequently converted to compound 17 by treating with HATU and an appropriate amine (R'R"NH, where R' and R" are each alkyl, aryl, heteroary, cycloalkyl or hetero-cycloalkyl, each of which is optionally substituted). Finally compound 17 can be converted to the corresponding hydroxamic acid derivatives of formula 18 by treating with hydroxylamine.

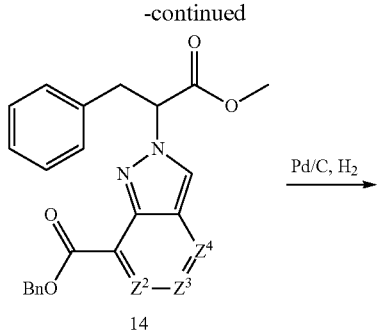

Scheme 3

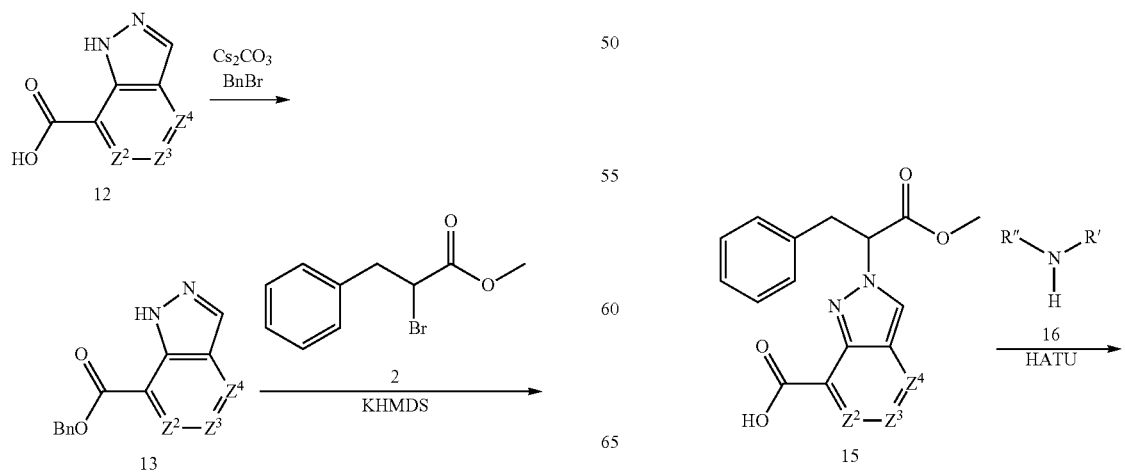

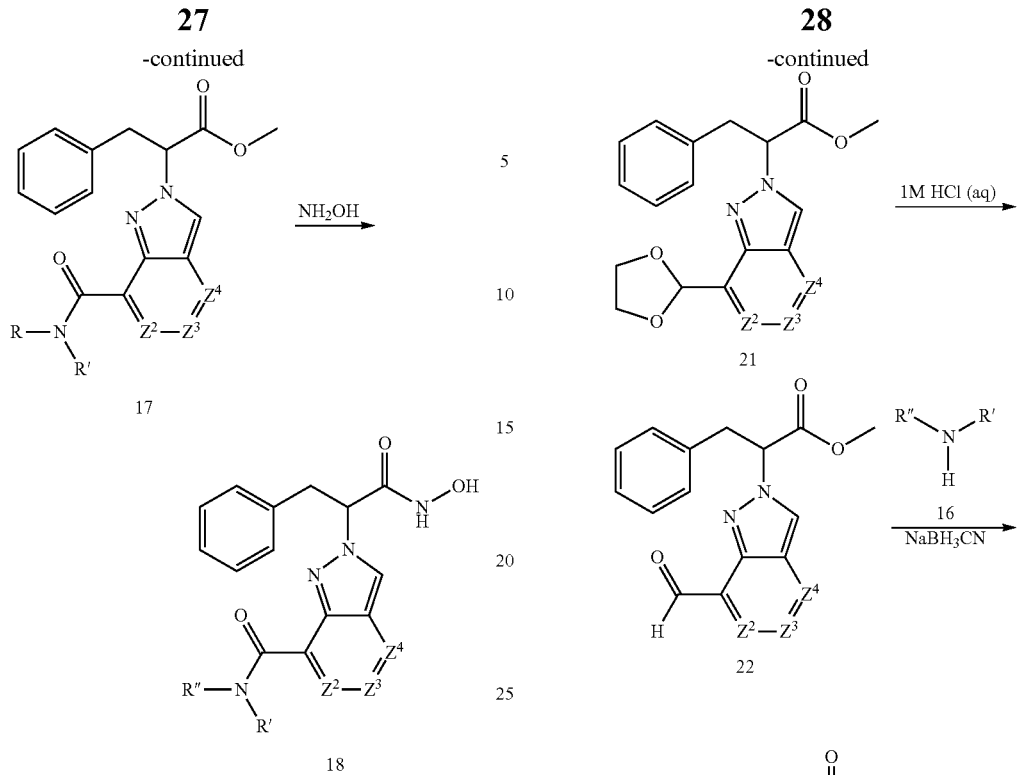

A series of hydroxamic acid derivatives of formula 24 can be prepared via the route illustrated in Scheme 4. The carbonyl group of compound 19 can be protected by 1,2-ethanediol to give the acetal 20 which can be converted to compound 21 by treating with KHMDS followed by compound 2. The acetal group of compound 21 can then be cleaved via acid-catalyzed hydrolysis to provide compound 22 which can be subsequently converted to compound 23 through reductive amination. The hydroxamic acid derivatives of formula 24 can be obtained by treating compound 23 with hydroxylamine.

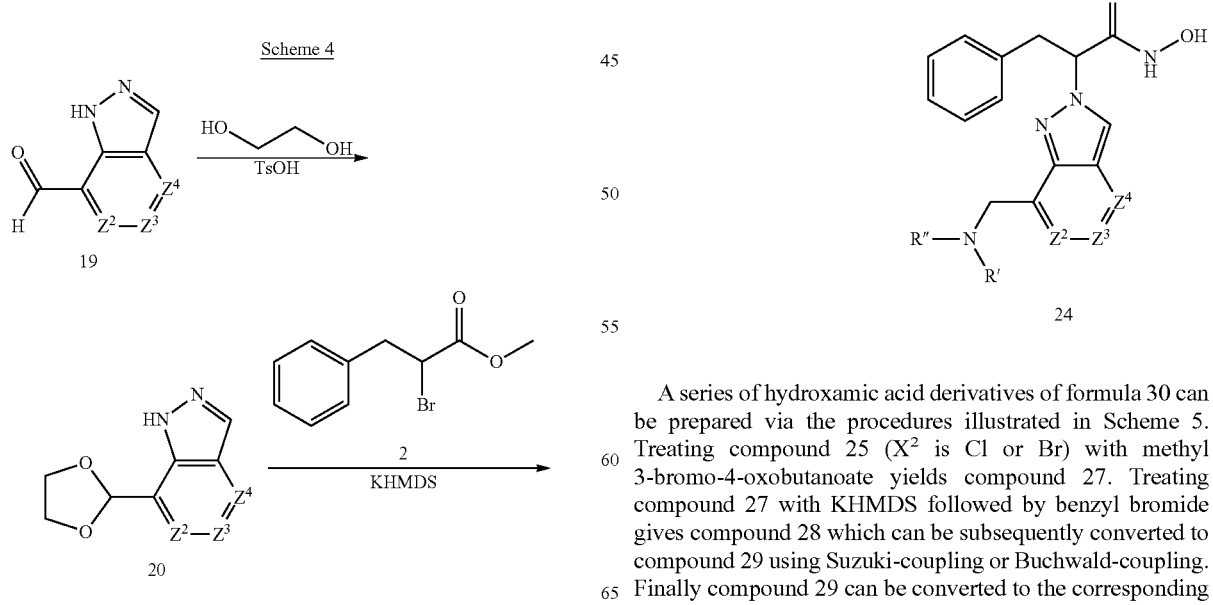

A series of hydroxamic acid derivatives of formula 30 can be prepared via the procedures illustrated in Scheme 5. Treating compound 25 ($X^2$ is Cl or Br) with methyl 3-bromo-4-oxobutanoate yields compound 27. Treating compound 27 with KHMDS followed by benzyl bromide gives compound 28 which can be subsequently converted to compound 29 using Suzuki-coupling or Buchwald-coupling. Finally compound 29 can be converted to the corresponding hydroxamic acid derivatives of formula 30 by treating with hydroxylamine.

Scheme 5

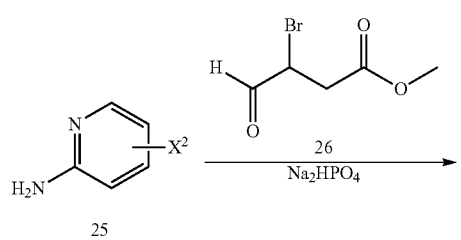

$X^2$ = Cl or Br

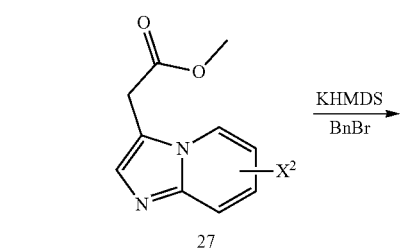

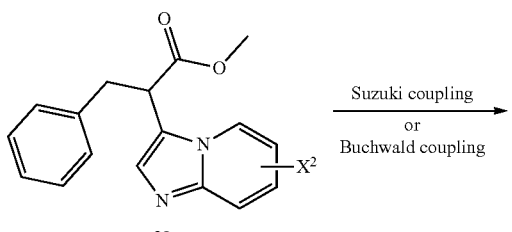

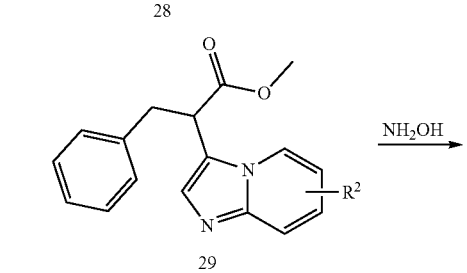

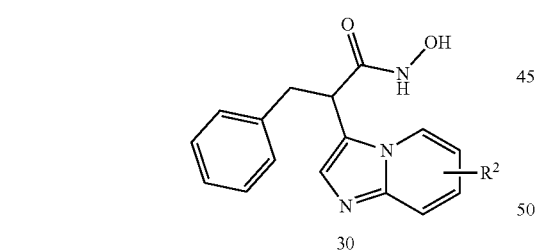

Scheme 6

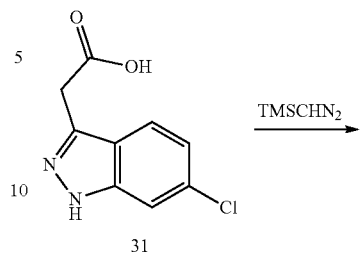

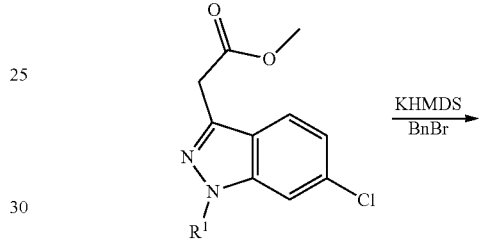

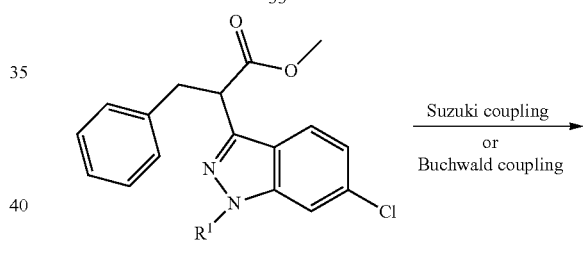

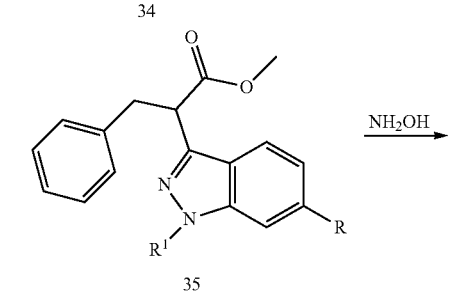

A series of hydroxamic acid derivatives of formula 36 can be prepared via the route illustrated in Scheme 6. Treating compound 31 with trimethylsilyldiazomethane yields the methyl ester 32. Treating compound 32 with KHMDS followed by an appropriate alkyl iodide (R'I) provides compound 33 which can be subsequently converted to compound 34 by treating with KHMDS followed by benzyl bromide. The compound 34 can then be converted to compound 35 using Suzuki-coupling or Buchwald-coupling. Finally compound 35 can be converted to the corresponding hydroxamic acid derivatives of formula 36 by treating with hydroxylamine.

A series of hydroxamic acid derivatives of formula 43 can be prepared via the route illustrated in Scheme 7. Treating compound 37 ($X^3$ is Cl or Br) with sodium hydride followed by compound 2 yields a mixture of compound 38 and compound 39 which can be separated via chromatography. The isolated compound 39 can be converted to compound 40 by treating with N-iodosuccinimide in the presence of trifluoroacetic acid. Through Sonogashira-coupling, compound 40 can be converted to compound 41 which can be subsequently converted to compound 42 via Suzuki-coupling or Buchwald-coupling. Finally compound 42 can be converted to the corresponding hydroxamic acid derivatives of formula 43 by treating with hydroxylamine.

Scheme 7

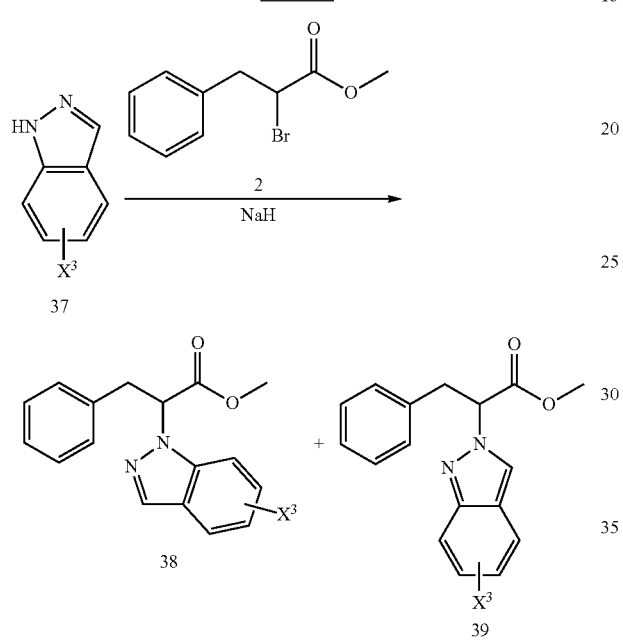

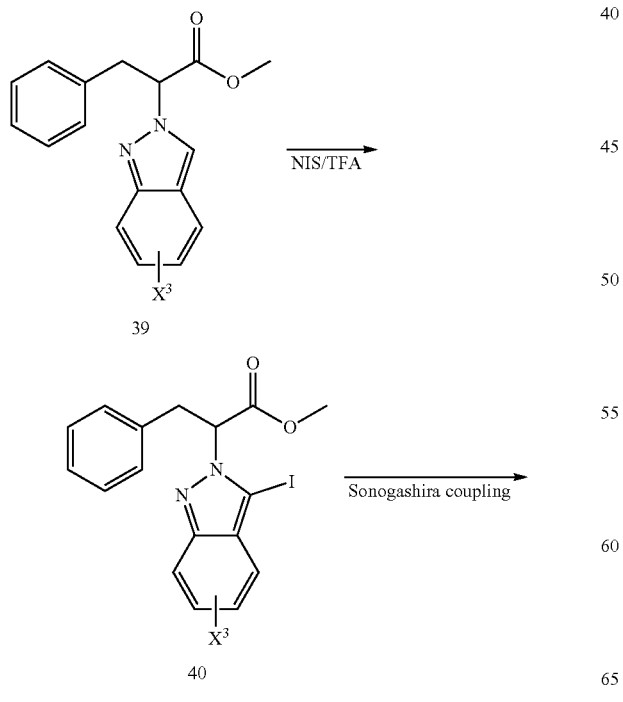

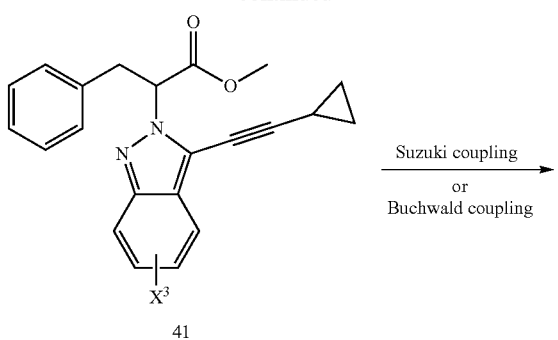

A series of hydroxamic acid derivatives of formula 50 can be prepared via the route illustrated in Scheme 8. Treating compound 44 with N-iodosuccinimide gives compound 45. Treating compound 45 with KHMDS followed by compound 2 yields a mixture of compound 46 and compound 47 which can be separated via chromatography. The isolated compound 47 can be converted to compound 48 through Sonogashira-coupling. Compound 48 can be subsequently converted to compound 49 via Suzuki-coupling or Buchwald-coupling. Finally compound 49 can be converted to the corresponding hydroxamic acid derivatives of formula 50 by treating with hydroxylamine.

Scheme 8

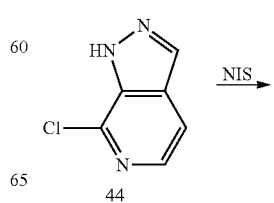

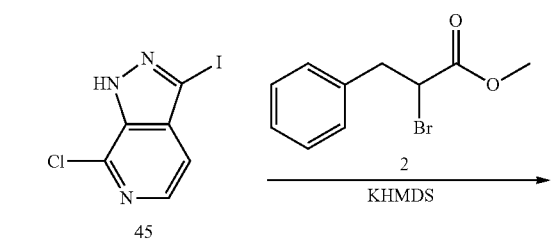

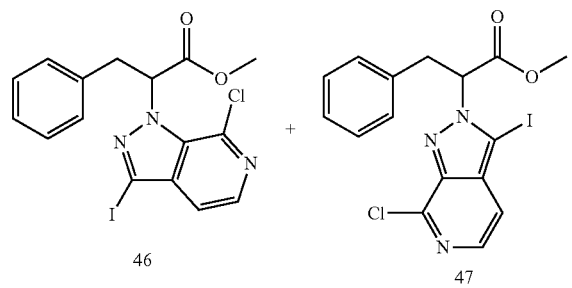

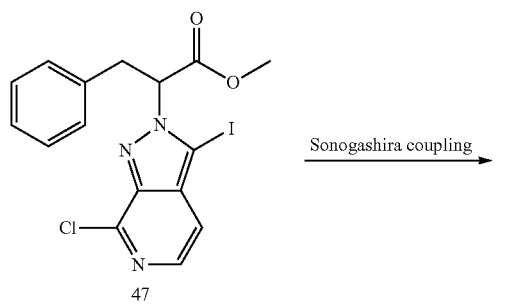

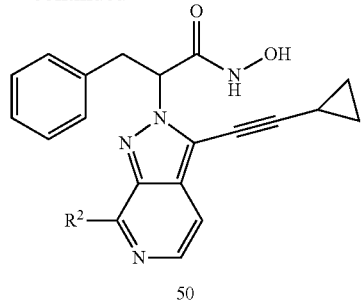

Methods of Use

Compounds of the present disclosure can modulate or inhibit the activity of HDACs. For example, the compounds of the disclosure can be used to inhibit activity of an HDAC enzyme such as HDAC8 in a cell or in an individual or patient in need of inhibition of the enzyme by administering an inhibiting amount of a compound of the disclosure to the cell, individual, or patient.

In some embodiments, the compounds of the disclosure are selective for the HDAC8 enzyme over one or more of other HADACs. In some embodiments, the compounds of the disclosure are selective for the HDACs over other enzymes. In some embodiments, the selectivity is 2-fold or more, 3-fold or more, 5-fold or more, 10-fold or more, 25-fold or more, 50-fold or more, or 100-fold or more.

As HDAC inhibitors, the compounds of the disclosure are useful in the treatment of various diseases associated with abnormal expression or activity of the HDACs or HDAC8. Compounds which inhibit HDACs will be useful in providing a means of preventing the growth or inducing apoptosis in tumors, particularly by inhibiting angiogenesis. It is therefore anticipated that the compounds will prove useful in treating or preventing proliferative disorders such as cancers.

In certain embodiments, the disclosure provides a method for treating a disease or disorder mediated by HDACs or HDAC8 in a patient in need thereof, comprising the step of administering to said patient a compound according to the invention, or a pharmaceutically acceptable composition thereof.

For example, the compounds of the disclosure are useful in the treatment of cancer. Example cancers include, but are not limited to, adenocarcinoma; adult T-cell leukemia/lymphoma; AIDS-associated leukemia; basal; cell carcinoma; biliary tract cancer; bladder cancer; blastoma; brain cancer including glioblastomas and medulloblastomas; breast cancer; cervical cancer; choriocarcinoma; chronic myelogenous leukemia; colon cancer; colorectal cancer; endometrial carcinoma; esophageal cancer; esticular cancer; gastric cancer; gastrointestinal cancer; Glioblastoma; hairy cell leukemia; hematological neoplasms including acute lymphocytic and myelogenous leukemia; Hodgkin's and non-Hodgkin's lymphoma; intraepithelial neoplasms including Bowen's disease and Paget's disease; leukemia; acute myeloid leukemia (AML); liver cancer such as hepatic carcinoma, hepatocellular carcinoma and hepatoma; lung cancer; lymphomas including Hodgkin's disease and lymphocytic lymphomas; melanoma; multiple myeloma; neuroblastomas; non-small cell lung cancer; oral cancer including squamous cell carcinoma; ovarian cancer including those arising from epithelial cells, stromal cells, germ cells and mesenchymal cells; pancreatic cancer; prostate cancer; rectal cancer; renal cancer including adenocarcinoma, kidney cancer, and Wilms' tumor; salivary gland carcinoma; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; small-cell lung cancer; squamous cell cancer; T-cell acute lymphoblastic leukemia/lymphoma; T-cell lymphoma; testicular cancer including germinal tumors such as seminoma, non-seminoma (teratomas, choriocarcinomas), stromal tumors, and germ cell tumors; thyroid cancer including thyroid adenocarcinoma and medullar carcinoma; vulval cancer, myeloproliferative neoplasms and any combinations thereof.

In other embodiments, exemplary cancers that are treatable with the compounds of the disclosure include, but are not limited to, bladder cancer, breast cancer, cervical cancer, colorectal cancer, cancer of the small intestine, colon cancer, rectal cancer, cacncer of the anus, endometrial cancer, gastric cancer, head and neck cancer (e.g., cancers of the larynx, hypopharynx, nasopharynx, oropharynx, lips, and mouth), kidney cancer, liver cancer (e.g., hepatocellular carcinoma, cholangiocellular carcinoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, esophageal cancer, gall bladder cancer, pancreatic cancer (e.g. exocrine pancreatic carcinoma), stomach cancer, thyroid cancer, parathyroid cancer, skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Further example cancers include hematopoietic malignancies such as leukemia or lymphoma, multiple myeloma, chronic lymphocytic lymphoma, adult T cell leukemia, B-cell lymphoma, cutaneous T-cell lymphoma, acute myelogenous leukemia, Hodgkin's or non-Hodgkin's lymphoma, myeloproliferative neoplasms (e.g., polycythemia vera, essential thrombocythemia, and primary myelofibrosis), Waldenstrom's Macroglubulinemia, hairy cell lymphoma, chronic myelogenic lymphoma, acute lymphoblastic lymphoma, AIDS-related lymphomas, and Burkitt's lymphoma.

Other cancers treatable with the compounds of the disclosure include tumors of the eye, glioblastoma, melanoma, rhabdosarcoma, lymphosarcoma, and osteosarcoma.

Compounds of the disclosure can also be useful in the inhibition of tumor metastisis.

In some embodiments, the present disclosure provides a method for treating hepatocellular carcinoma in a patient in need thereof, comprising the step of administering to said patient a compound of Formula (I) or a compound as disclosed herein, or a pharmaceutically acceptable salt thereof, or a composition comprising a compound of Formula (I) or a compound as disclosed herein.

In some embodiments, the present disclosure provides a method for treating rhabdomyosarcoma, esophageal cancer, breast cancer, or cancer of a head or neck, in a patient in need thereof, comprising the step of administering to said patient a compound Formula (I) or a compound as disclosed herein, or a pharmaceutically acceptable salt thereof, or a composition comprising a compound of Formula (I) or a compound as disclosed herein.

In some embodiments, the present disclosure provides a method of treating cancer, wherein the cancer is selected from hepatocellular cancer, breast cancer, bladder cancer, colorectal cancer, melanoma, mesothelioma, lung cancer, prostate cancer, pancreatic cancer, testicular cancer, thyroid cancer, squamous cell carcinoma, glioblastoma, neuroblastoma, uterine cancer, and rhabdosarcoma.

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds of Formula (I) or a compound as described herein for treatment of HDAC-associated diseases, disorders or conditions. The agents can be combined with the present compounds in a single dosage form, or the agents can be administered simultaneously or sequentially as separate dosage forms.

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis (POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with the compounds of the present disclosure for the treatment of cancer include chemotherapeutic agents, targeted cancer therapies, immunotherapies or radiation therapy. Compounds of this invention may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present invention. These include anti-androgens including but not limited to flutamide, bicalutamide, and nilutamide, luteinizing hormone-releasing hormone (LHRH) analogs including leuprolide, goserelin, triptorelin, and histrelin LHRH antagonists (e.g. degarelix), androgen receptor blockers (e.g. enzalutamide) and agents that inhibit androgen production (e.g. abiraterone).

Suitable agents for use in combination with the compounds of the present disclosure for the treatment of cancer include, but are not limited to, abarelix; actinomycin D; Aldesleukin; alemtuzutnab; alitretinoin; allopurinol; altretamine; amifostine; anastrozole; arsenic trioxide; Asparaginase; azacitidine; BCG Live; bevacizumab; bexarotene;

bexarotene capsules; bexarotene gel; bleomycin; bortezomib; busulfan; busulfan intravenous; busulfanoral; calusterone; capecitabine; carboplatin; carmustine; carmustine with polifeprosan Implant; celecoxib; cetuximab; chlorambucil; cisplatin; cladribine; clofarabine; cyclophosphamide; cytarabine; cytarabine liposomal; dacarbazine; dactinomycin; darbepoetin alfa; dasatinib; daunomycin; daunorubicin; daunorubicin liposomal; decitabine; denileukin; Denileukin diftitox; dexrazoxane; docetaxel; doxorubicin; doxorubicin liposomal; Dromostanolone propionate; Elliott's B Solution; Epirubicin; Epoetin alfa; Epoetin alfa estramustine; erlotinib; estramustine; etoposide (VP-16); etoposide phosphate; exemestane; Filgrastim; floxuridine; floxuridine (intraarterial); fludarabine; fluorouracil (5-EU); fulvestrant; gefitinib; gemcitabine; gemtuzumab ozogamicin; germicitibine; goserelin acetate; histrelin acetate; hydroxyurea; Ibritumomab Tiuxetan; idarubicin; ifosfamide; imatinib mesylate; interferon alfa 2a; Interferon alfa-2b; irinotecan; lenalidomide; letrozole; leucovorin; leuprolide acetate; levamisole; LOddC; lomustine (CCNU); mechlorethamine (nitrogenmustard); megestrol acetate; melphalan (L-PAM); mercaptopurine (6-MP); mesna; methotrexate; methoxsalen; mithramycin; mithramycin; mitomycin C; mitotane; mitoxantrone; nandrolone phenpropionate; nelarabine; Nofeturnomab; Oprelvekin; oxaliplatin; paclitaxel (taxol); paclitaxel protein-bound particles; paclitaxeicarbohydrate conjugates; palifermin; pamidronate; panitumumab; pegademase; Pegaspargase; Pegfilgrastitn; pemetrexed disodium; pentostatin; pipobroman; plicamycin; porfirner sodium; procarbazine; quinacrine; Rasburicase; Rituximab; Sargramostim; streptozocin; sunitinib maleate; talbuvidine (LDT); talc; tamoxifen; temozolomide; teniposide (VM-26); testolactone; thalidomide; thioguanine (6-TG); thiotepa; topotecan; toremifene; Tositumotnab or 1131-Tositumotnab; trastuzumab; tretinoin (ATRA); uracil mustard; valrubicin; valtorcitabine (monoval LDC); vinblastine; vincristine; vinorelbine; vorinostat; zoledronate; zoledronic acid; and any combinations thereof.

Compounds of the present invention may be combined with or in sequence with other agents against HDACs enzymes especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuxitnab, panitumumab and necitumumab. Inhibitors of c-Met may be used in combination with HDACs such as HDAC8 inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with HDACs inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds of the present invention include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with HDACs inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib, INCB39110), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds of the present invention. In some embodiments, the JAK inhibitor is selective for JAK1 over JAK2 and JAK3. EGFR inhibitors (FGFR1, FGFR2, FGFR3 or FGFR4, e.g., INCB54828, INCB62079 and INCB63904), IDO inhibitors (e.g., epacadostat and NLG919), LSD1 inhibitors (e.g., INCB59872 and INCB60003), a TDO inhibitor, a PI3K-delta inhibitor (e.g., INCB50797 and INCB50465), a PI3K-gamma inhibitor such as a PI3K-gamma selective inhibitor, a Pim inhibitor, a CSF1R inhibitor, a TAM receptor tyrosine kinases (Tyro-3, Axl, and Mer), an angiogenesis inhibitor, an interleukin receptor inhibitor, bromo and extra terminal family members inhibitors (for example, bromodomain inhibitors or BET inhibitors such as INCB54329 and INCB57643) and an adenosine receptor antagonist or combinations thereof, can also be combined with compounds of the present invention.

Compounds of the present invention can be used in combination with one or more immune checkpoint inhibitors. Exemplary immune checkpoint inhibitors include inhibitors against immune checkpoint molecules such as CD27, CD28, CD40, CDI22, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors. 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab or pembrolizumab. In some embodiments, the anti-PD1 antibody is pembrolizumab. In some embodiments, the anti PD-1 antibody is SHR-1210.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518 or MK-4166.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562. In some embodiments, the OX40L fusion protein is MEDI6383.

Compounds of the present invention can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Other suitable agents for use in combination with the compounds of the present invention include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with the compounds of the present invention include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds according to the invention may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and hamatopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition. Medical Economics Company, Montvale, N.J.), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions which refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents preserving agents such as methyl- and propylhydroxy-benzoates sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, vaccines, antibodies, immune enhancers, immune suppressants, anti-inflammatory agents and the like.

Labeled Compounds and Assay Methods

Another aspect of the present invention relates to fluorescent dye, spin label, heavy metal or radio-labeled compounds of the invention that would be useful not only in imaging but also in assays, both in vitro and in vivo, for localizing and quantitating the HDACs in tissue samples, including human, and for identifying HDACs ligands by inhibition binding of a labeled compound. Accordingly, the present invention includes HDACs assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro HDACs enzymes labeling and competition assays, compounds that incorporate $^3$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br. Synthetic methods for incorporating radio-isotopes into organic compounds are applicable to compounds of the invention and are well known in the art.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compounds as described herein or recited in the claims include two or more deuterium atoms. In some embodiments, the compounds as described herein or recited in the claims include 1, 2, 3, 4, 5, 6, 7, 8, 9, 10, 11 or 12 deuterium atoms. Synthetic methods for including isotopes into organic compounds are known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the HDACs enzymes. Accordingly, the ability of a test compound to compete with the radio-labeled compound for binding to the HDACs enzymes directly correlates to its binding affinity.

Kits

The present invention also includes pharmaceutical kits useful, for example, in the treatment or prevention of HDACs-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of HDACs such as HDAC8 as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Hague, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 µm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ C$_{18}$ 5 µm, 2.1×5.0 mm, Buffers: mobile phase A: 0.025% TEA in water and mobile phase B: 0.025% TEA in acetonitrile; gradient 2% to 80% of B in 3 minutes with flow rate 1.5 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions set out below in Methods A and B.

Unless otherwise indicated, the example compounds were purified by preparative HPLC using acidic conditions (method A) and were obtained as a TFA salt, or using basic conditions (method B) and were obtained as a free base.

Method A:

Column: Waters SunFire™ C18, 5 µm particle size, 30×100 mm;

Mobile phase: water (0.1% TFA)/MeCN

Flow rate: 60 mL/min.

Gradient: 5 min. or 12 min. from 5% MeCN/95% water to 100% MeCN

Method B:

Column: Waters XBridge™ C18, 5 µm particle size, 30×100 mm;

Mobile phase: water (0.15% NH$_4$OH)/MeCN

Flow rate: 60 mL/min.

Gradient: 5 min or 12 min from 5% MeCN/95% water to 100% MeCN

The example compounds and intermediates below containing one or more chiral centers were obtained as scalemic or racemic mixtures, unless otherwise specified.

Scheme 9

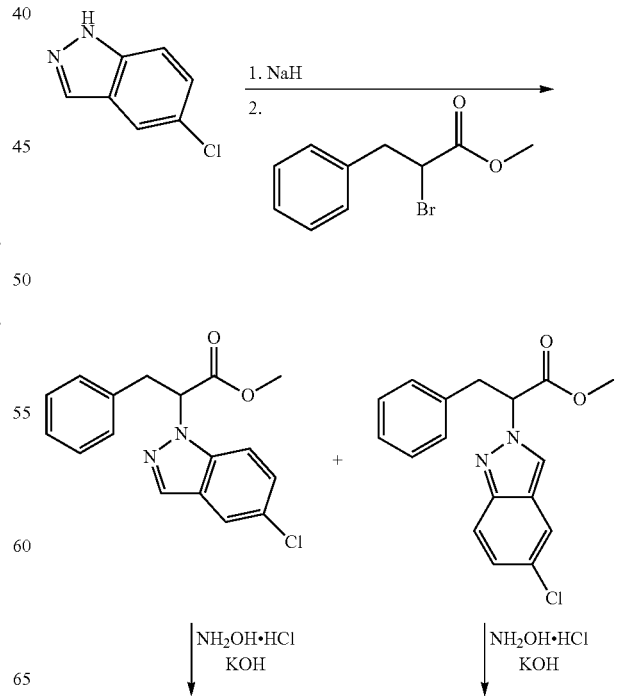

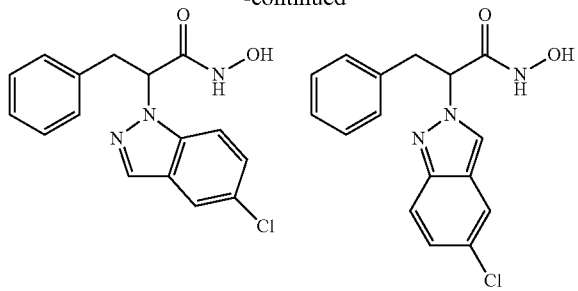

Example 1

2-(5-Chloro-1H-indazol-1-yl)-N-hydroxy-3-phenyl-propanamide (I-0001)

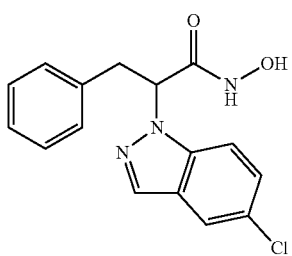 [SMILES: O=C(NO)C(Cc1ccccc1)n1ncc2nc(Cl)ccc21]

Step 1. Methyl 2-(5-chloro-1H-indazol-1-yl)-3-phenylpropanoate and methyl 2-(5-chloro-2H-indazol-2-yl)-3-phenylpropanoate

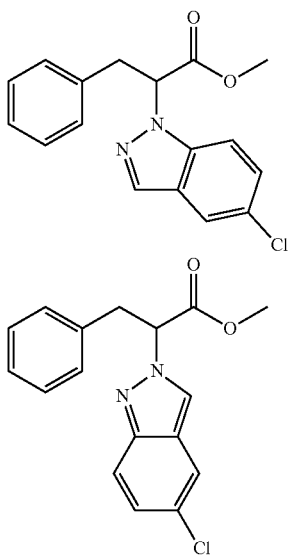

To a suspension of 60% NaH in mineral oil (203.5 mg, 5.087 mmol) in DMF (3.0 mL) at 0° C. was added a solution of 5-chloro-1H-indazole (827.8 mg, 5.425 mmol) in DMF (6.0 mL) dropwise. The mixture stirred at 0° C. for 40 min. Then a solution of methyl 2-bromo-3-phenylpropanoate (1114 mg, 4.582 mmol) in DMF (8.0 mL) was added. The reaction mixture was allowed to warm to room temperature. After stirring at room temperature overnight, the reaction mixture was diluted with EtOAc, washed with water and brine. The organic layer was dried over anhydrous $Na_2SO_4$, filtered and concentrated. The residue was purified on silica gel (120 g, 0-100% EtOAc in hexanes) to give methyl 2-(5-chloro-1H-indazol-1-yl)-3-phenylpropanoate (767.1 mg, 53%, LCMS calculated for $C_{17}H_{16}ClN_2O_2$ $(M+H)^-$: m/z=315.1; found 315.1) and methyl 2-(5-chloro-2H-indazol-2-yl)-3-phenylpropanoate (260.5 mg, 18%, LCMS calculated for $C_{17}H_{16}ClN_2O_2$ $(M+H)^+$: m/z=315.1; found 315.1). $^1$H NMR (500 MHz, CD3CN) δ 8.02 (s, 1H), 7.71 (d, J=1.8 Hz, 1H), 7.41 (d, J=9.0 Hz, 1H), 7.27 (dd, J=9.0, 1.8 Hz, 1H), 7.14-6.98 (m, 5H), 5.37 (dd, J=10.1, 5.4 Hz, 1H), 3.66-3.48 (m, 2H).

Step 2. 2-(5-Chloro-1H-indazol-1-yl)-N-hydroxy-3-phenylpropanamide

To a suspension of hydroxylamine hydrochloride (97.1 mg, 1.40 mmol) in MeOH (0.50 mL) was added a solution of KOH (156.8 mg, 2.795 mmol) in MeOH (0.50 mL). The resulting white suspension was stirred at room temperature for 30 min, and then cooled to 0° C. A solution of methyl 2-(5-chloro-1H-indazol-1-yl)-3-phenylpropanoate (43.6 mg, 0.138 mmol) in MeOH (0.5 mL) was added. The reaction was stirred at 0° C. for 30 min, and then neutralized with 0.5 mL 4.0 M HCl (aq). The mixture was diluted with MeOH and filtered. The filtrate was purified using RP-HPLC (Waters XBridge™ C18 column, 30 mm×100 mm, 5 μm particle size, eluting with a gradient of MeCN/water containing 0.15% $NH_4OH$, at flow rate of 60 mL/min) to afford compound (I-0001) as a white solid (19.1 mg, 44%). LCMS calculated for $C_{16}H_{15}ClN_3O_2$ $(M+H)^+$: m/z=316.1; found 316.1. IC50: 141 nM.

Example 2

2-(5-Chloro-2H-indazol-2-yl)-N-hydroxy-3-phenyl-propanamide (I-0003)

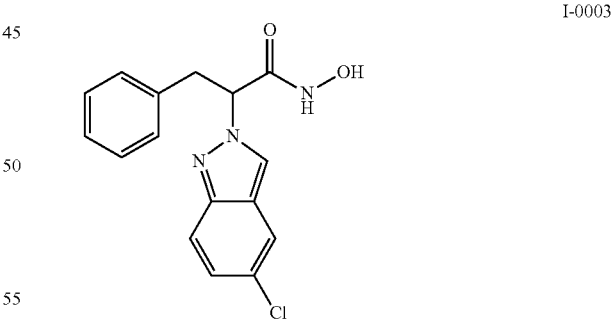

To a suspension of hydroxylamine hydrochloride (94.6 mg, 1.36 mmol) in MeOH (0.50 mL) was added a solution of KOH (156.8 mg, 2.795 mmol) in MeOH (0.50 mL). The resulting white suspension was stirred at room temperature for 30 min, and then cooled to 0° C. A solution of methyl 2-(5-chloro-2H-indazol-2-yl)-3-phenylpropanoate (40.1 mg, 0.127 mmol, see step 1 in example 1) in MeOH (0.5 mL) was added. The reaction was stirred at 0° C. for 30 min, and then neutralized with 0.5 mL 4.0 M HCl (aq). The mixture was diluted with MeOH and filtered. The filtrate was purified using RP-HPLC (Waters XBridge™ C18 column, 30 mm×100 mm, 5 μm particle size, eluting with a gradient of MeCN/water containing 0.15% NH₄OH, at flow rate of 60 mL/min) to afford compound (I-0003) as a white solid (26.8 mg, 67%). LCMS calculated for $C_{16}H_{15}ClN_3O_2$ (M+H)⁺: m/z=316.1; found 316.1. IC50: 338 nM.

TABLE 1

The compounds listed in Table 1 were prepared in accordance with the synthetic protocols set forth in Scheme 9 and Examples 1 and 2, using the suitable starting materials.

| No. | Name | Compound ¹H-NMR | LCMS (M + H)⁺ |
|---|---|---|---|
| I-0102 | N-hydroxy-2-(1H-indazol-1-yl)-3-phenylpropanamide | | 282.1 |
| I-0002 | N-hydroxy-2-(2H-indazol-2-yl)-3-phenylpropanamide | ¹H NMR (500 MHz, DMSO) δ 9.84 (s, 1H), 8.51 (d, J = 0.7 Hz, 1H), 7.71-7.65 (m, 1H), 7.54 (dd, J = 8.7, 0.9 Hz, 1H), 7.24-7.12 (m, 6H), 7.00 (ddd, J = 8.3, 6.6, 0.7 Hz, 1H), 5.33 (dd, J = 8.4, 7.3 Hz, 1H), 3.57-3.42 (m, 2H). | 282.1 |
| I-0037 | 2-(6-fluoro-2H-indazol-2-yl)-N-hydroxy-3-phenylpropanamide | ¹H NMR (400 MHz, DMSO) δ 11.05 (s, 1H), 8.57 (s, 1H), 7.75 (dd, J = 9.0, 5.6 Hz, 1H), 7.37-7.03 (m, 6H), 7.03-6.78 (m, 1H), 5.31 (t, J = 7.8 Hz, 1H), 3.72-3.33 (m, 2H). | 300.1 |

TABLE 1-continued

The compounds listed in Table 1 were prepared in accordance with the synthetic protocols set forth in Scheme 9 and Examples 1 and 2, using the suitable starting materials.

| No. | Name | Compound | ¹H-NMR | LCMS (M + H)⁺ |
|---|---|---|---|---|
| I-0038 | N-hydroxy-3-phenyl-2-(6-(trifluoromethyl)-2H-indazol-2-yl)propanamide | | | 350.1 |
| I-0017 | 2-(5-bromo-1H-indazol-1-yl)-N-hydroxy-3-phenylpropanamide | | | 360.0 |
| I-0021 | 2-(6-bromo-1H-indazol-1-yl)-N-hydroxy-3-phenylpropanamide | | | 360.0 |
| I-0024 | 2-(5-bromo-2H-indazol-2-yl)-N-hydroxy-3-phenylpropanamide | | | 360.0 |
| I-0004 | 2-(6-bromo-2H-indazol-2-yl)-N-hydroxy-3-phenylpropanamide | | ¹H NMR (500 MHz, DMSO) δ 9.82 (s, 1H), 8.58 (s, 1H), 7.88-7.77 (m, 1H), 7.68 (d, J = 8.9 Hz, 1H), 7.28-7.07 (m, 6H), 5.33 (t, J = 7.9 Hz, 1H), 3.57-3.42 (m, 2H). | 360.0 |

TABLE 1-continued

The compounds listed in Table 1 were prepared in accordance with the synthetic protocols set forth in Scheme 9 and Examples 1 and 2, using the suitable starting materials.

| No. | Name | Compound ¹H-NMR | LCMS (M + H)⁺ |
|---|---|---|---|
| I-0039 | 2-(6-bromo-5-methyl-2H-indazol-2-yl)-N-hydroxy-3-phenylpropanamide | ¹H NMR (400 MHz, DMSO) δ 11.05 (s, 1H), 8.47 (s, 1H), 7.86 (s, 1H), 7.66 (s, 1H), 7.33-6.94 (m, 5H), 5.29 (t, J = 7.8 Hz, 1H), 3.67-3.31 (m, 2H), 2.37 (s, 3H). | 374.1 |
| I-0068 | 2-(7-bromo-2H-indazol-2-yl)-N-hydroxy-3-phenylpropanamide | | 360.0 |
| I-0076 | 2-(5-chloro-1H-pyrazolo[4,3-b]pyridin-1-yl)-N-hydroxy-3-phenylpropanamide | | 317.1 |
| I-0077 | 2-(5-chloro-2H-pyrazolo[4,3-b]pyridin-2-yl)-N-hydroxy-3-phenylpropanamide | | 317.1 |
| I-0042 | N-hydroxy-3-phenyl-2-(1H-pyrazolo[4,3-c]pyridin-1-yl)propanamide | | 283.1 |

TABLE 1-continued

The compounds listed in Table 1 were prepared in accordance with the synthetic protocols set forth in Scheme 9 and Examples 1 and 2, using the suitable starting materials.

| No. | Name | Compound ¹H-NMR | LCMS (M + H)⁺ |
|---|---|---|---|
| I-0043 | N-hydroxy-3-phenyl-2-(2H-pyrazolo[4,3-c]pyridin-2-yl)propanamide | ¹H NMR (500 MHz, DMSO) δ 9.72 (s, 1H), 9.47 (s, 1H), 8.31 (d, J = 7.0 Hz, 1H), 8.07 (d, J = 7.0 Hz, 1H), 7.32-7.03 (m, 5H), 5.64 (dd, J = 8.9, 6.9 Hz, 1H), 3.68-3.53 (m, 2H). | 283.1 |
| I-0054 | N-hydroxy-2-(7-iodo-2H-pyrazolo[4,3-c]pyridin-2-yl)-3-phenylpropanamide |  | 409.0 |
| I-0055 | 2-(4-chloro-1H-pyrazolo[4,3-c]pyridin-1-yl)-N-hydroxy-3-phenylpropanamide |  | 317.1 |
| I-0056 | 2-(4-chloro-2H-pyrazolo[4,3-c]pyridin-2-yl)-N-hydroxy-3-phenylpropanamide |  | 317.1 |
| I-0099 | 2-(5-bromo-1H-pyrazolo[3,4-c]pyridin-1-yl)-N-hydroxy-3-phenylpropanamide |  | 361.0 |

TABLE 1-continued

The compounds listed in Table 1 were prepared in accordance with the synthetic protocols set forth in Scheme 9 and Examples 1 and 2, using the suitable starting materials.

| No. | Name | Compound $^1$H-NMR | LCMS (M + H)$^+$ |
|---|---|---|---|
| I-0100 | 2-(5-bromo-2H-pyrazolo[3,4-c]pyridine-2-yl)-N-hydroxy-3-phenylpropanamide | | 361.0 |
| I-0129 | 2-(7-chloro-2H-pyrazolo[3,4-c]pyridin-2-yl)-N-hydroxy-3-phenylpropanamide | | 317.1 |
| I-0122 | 2-(5-bromo-1H-pyrazolo[3,4-b]pyridin-1-yl)-N-hydroxy-3-phenylpropanamide | | 361.0 |
| I-0123 | 2-(5-bromo-2H-pyrazolo[3,4-b]pyridin-2-yl)-N-hydroxy-3-phenylpropanamide | | 361.0 |
| I-0124 | 2-(7-chloro-3-iodo-1H-pyrazolo[3,4-c]pyridin-1-yl)-N-hydroxy-3-phenylpropanamide | | 443.0 |

TABLE 1-continued

The compounds listed in Table 1 were prepared in accordance with the synthetic protocols set forth in Scheme 9 and Examples 1 and 2, using the suitable starting materials.

| No. | Name | Compound | ¹H-NMR | LCMS (M + H)⁺ |
|---|---|---|---|---|
| I-0125 | 2-(7-chloro-3-iodo-2H-pyrazolo[3,4-c]pyridin-2-yl)-N-hydroxy-3-phenylpropanamide | | | 443.0 |
| I-0135 | 2-(7-chloro-3-iodo-2H-indazol-2-yl)-N-hydroxy-3-phenylpropanamide | | | 442.0 |
| I-0201 | N-hydroxy-3-phenyl-2-(4,5,6,7-tetrahydro-1H-indazol-1-yl)propanamide | | ¹H NMR (500 MHz, DMSO) δ 7.22-7.11 (m, 4H), 7.02-6.98 (m, 2H), 4.70 (dd, J = 8.6, 6.6 Hz, 1H), 3.32-3.24 (m, 2H), 2.48-2.40 (m, 1H), 2.34 (m, 2H), 2.02 (m, 1H), 1.67-1.41 (m, 4H). | 286.2 |
| I-0200 | N-hydroxy-3-phenyl-2-(4,5,6,7-tetrahydro-2H-indazol-2-yl)propanamide | 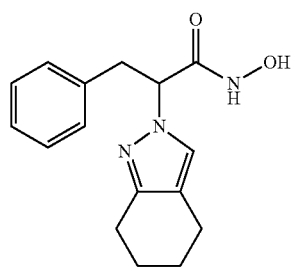 [SMILES: O=C(NO)C(Cc1ccccc1)n1cc2c(n1)CCCC2] | ¹H NMR (500 MHz, DMSO) δ 7.50 (s, 1H), 7.28-7.14 (m, 5H), 4.84 (t, J = 7.8 Hz, 1H), 3.26 (m, 2H), 2.49-2.40 (m, 4H), 1.64 (m, 4H). | 286.2 |
| I-0041 | 2-(1H-benzo[d]imidazol-1-yl)-N-hydroxy-3-phenylpropanamide | 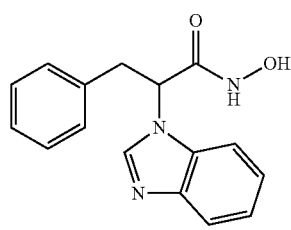 [SMILES: O=C(NO)C(Cc1ccccc1)n1cnc2ccccc21] | | 282.1 |

TABLE 1-continued

The compounds listed in Table 1 were prepared in accordance with the synthetic protocols set forth in Scheme 9 and Examples 1 and 2, using the suitable starting materials.

| No. | Name | Compound ¹H-NMR | LCMS (M + H)⁺ |
|---|---|---|---|
| I-0193 | 2-(5-chloro-1H-pyrrolo[3,2-b]pyridin-1-yl)-N-hydroxy-3-phenylpropanamide | ¹H NMR (500 MHz, DMSO) δ 10.98 (s, 1H), 7.96 (d, J = 3.4 Hz, 1H), 7.93 (d, J = 8.6 Hz, 1H), 7.23-7.08 (m, 6H), 6.53 (d, J = 3.4 Hz, 1H), 5.17-5.10 (m, 1H), 3.51-3.31 (m, 2H). | 316.1 |
| I-0196 | 2-(4-chloro-1H-pyrrolo[3,2-c]pyridin-1-yl)-N-hydroxy-3-phenylpropanamide | ¹H NMR (500 MHz, DMSO) δ 7.96 (d, J = 5.8 Hz, 1H), 7.85 (d, J = 3.4 Hz, 1H), 7.53-7.49 (m, 1H), 7.24-7.08 (m, 5H), 6.57 (d, J = 3.4 Hz, 1H), 5.20 (dd, J = 8.8, 6.9 Hz, 1H), 3.50-3.34 (m, 2H). | 316.1 |
| I-0194 | 2-(5-chloro-1H-pyrrolo[2,3-c]pyridin-1-yl)-N-hydroxy-3-phenylpropanamide | ¹H NMR (500 MHz, DMSO) δ 11.02 (s, 1H), 8.65 (s, 1H), 7.95 (d, J = 3.2 Hz, 1H), 7.55 (s, 1H), 7.16 (m, 5H), 6.50 (d, J = 3.2 Hz, 1H), 5.27-5.22 (m, 1H), 3.52-3.34 (m, 2H). | 316.1 |

US 10,723,705 B2

TABLE 1-continued

The compounds listed in Table 1 were prepared in accordance with the synthetic protocols set forth in Scheme 9 and Examples 1 and 2, using the suitable starting materials.

| No. | Name | Compound | $^1$H-NMR | LCMS (M + H)$^+$ |
|---|---|---|---|---|
| I-0195 | 2-(5-chloro-1H-pyrrolo[2,3-b]pyridin-1-yl)-N-hydroxy-3-phenylpropanamide | | $^1$H NMR (500 MHz, DMSO) δ 11.12 (s, 1H), 8.14 (d, J = 2.3 Hz, 1H), 8.01 (d, J = 2.3 Hz, 1H), 7.97 (d, J = 3.6 Hz, 1H), 7.18-7.05 (m, 5H), 6.45 (d, J = 3.6 Hz, 1H), 5.65 (dd, J = 9.8, 6.0 Hz, 1H), 3.44-3.29 (m, 2H). | 316.1 |

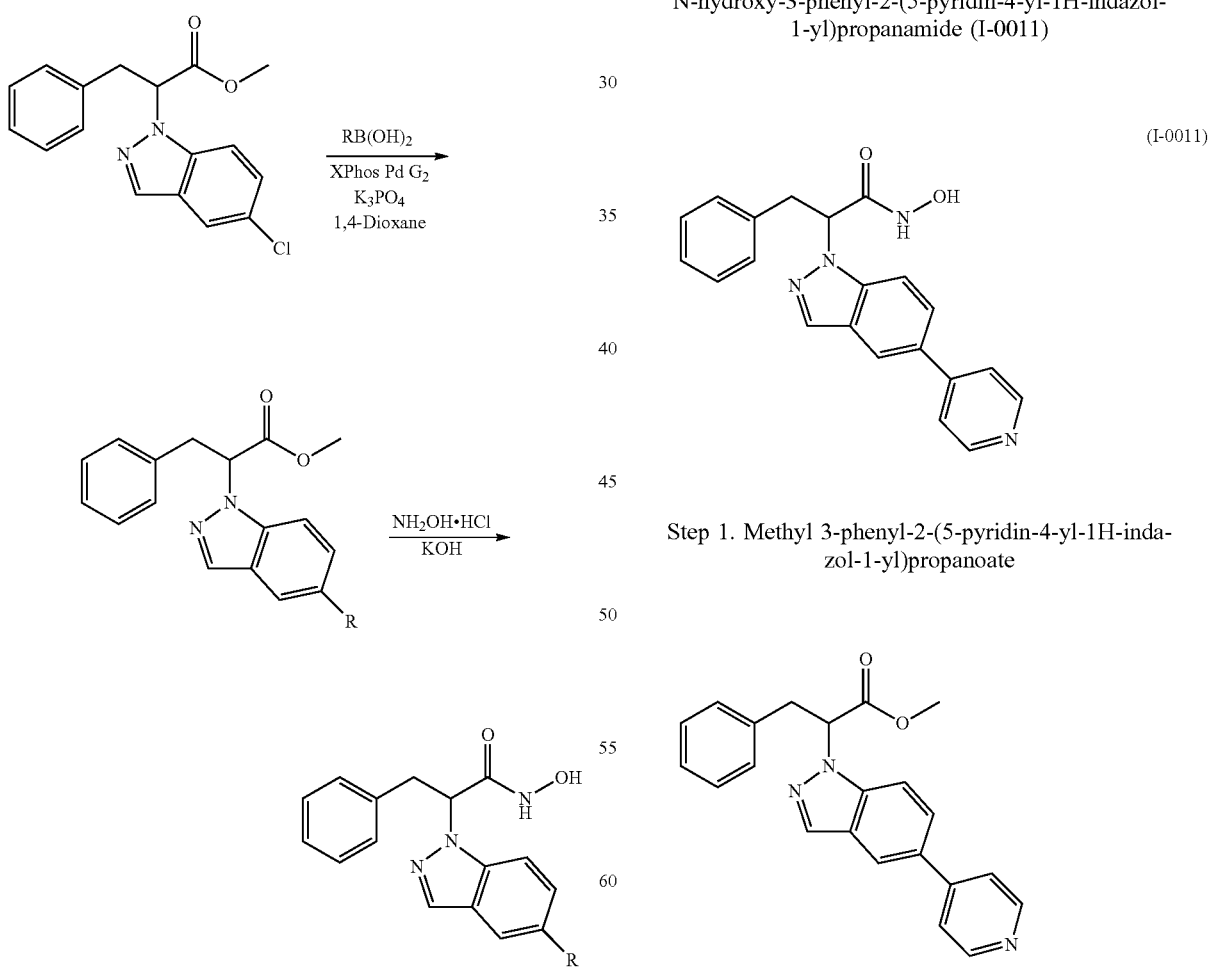

Scheme 10

Example 3

N-hydroxy-3-phenyl-2-(5-pyridin-4-yl-1H-indazol-1-yl)propanamide (I-0011)

Step 1. Methyl 3-phenyl-2-(5-pyridin-4-yl-1H-indazol-1-yl)propanoate

To a screw-cap vial equipped with a magnetic stir bar was added 4-(4,4,5,5-tetramethyl-1,3,2-dioxaborolan-2-yl)pyridine (89.5 mg, 0.436 mmol), dicyclohexyl(2',4',6'-triisopropylbiphenyl-2-yl)phosphine-(2'-aminobiphenyl-2-yl)(chloro)palladium (1:1) (XPhos Pd G2, Aldrich, 18.0 mg, 0.0228 mmol), and potassium phosphate (194.9 mg, 0.9182 mmol). The vial was sealed with a Teflon-lined septum, evacuated and backfilled with nitrogen (this process was repeated a total of three times). A solution of methyl 2-(5-chloro-1H-indazol-1-yl)-3-phenylpropanoate (66.0 mg, 0.210 mmol) in 1,4-dioxane (2.0 mL) was added followed by degassed water (0.10 mL). The reaction was stirred at 80° C. for 1 h. After cooling to room temperature, the reaction was filtered through a silica gel plug (eluted with EtOAc). The filtrate was concentrated. The resulting residue was purified on silica gel (40 g, 0-100% EtOAc in hexanes) to give the desired product as a pale yellow semi-oil (55.3 mg, 74%). LCMS calculated for $C_{22}H_{20}N_3O_2$ (M+H)$^+$: m/z=358.2; found 358.1.

Step 2. N-hydroxy-3-phenyl-2-(5-pyridin-4-yl-1H-indazol-1-yl)propanamide

To a suspension of hydroxylamine hydrochloride (126.2 mg, 1.816 mmol) in MeOH (0.50 mL) was added a solution of KOH (156.8 mg, 2.795 mmol) in MeOH (0.50 mL). The resulting white suspension was stirred at room temperature for 30 min, and then cooled to 0° C. A solution of methyl 3-phenyl-2-(5-pyridin-4-yl-1H-indazol-1-yl)propanoate (55.3 mg, 0.155 mmol) in MeOH (1.0 mL) was added. The reaction was stirred at 0° C. for 30 min, and then neutralized with 0.5 mL 4.0 M HCl (aq). The mixture was diluted with MeOH and filtered. The filtrate was purified using RP-HPLC (Waters XBridge™ C18 column, 30 mm×100 mm, 5 μm particle size, eluting with a gradient of MeCN/water containing 0.15% NH$_4$OH, at flow rate of 60 mL/min) to afford compound (I-0011) as a white solid (19.4 mg, 35%). LCMS calculated for $C_{21}H_{19}N_4O_2$ (M+H)$^+$: m/z=359.2; found 359.1. IC50: 87 nM.

TABLE 2

The following compounds were prepared as depicted in example 3, using the appropriate starting materials.

| No. | Name | Structure/$^1$H-NMR | LCMS (M + H)$^+$ |
|---|---|---|---|
| I-0079 | N-hydroxy-3-phenyl-2-(4-phenyl-1H-indazol-1-yl)propanamide | $^1$H NMR (400 MHz, DMSO) δ 10.91 (s, 1H), 8.14 (s, 1H), 7.72 (d, J = 8.5 Hz, 1H), 7.68 (d, J = 7.4 Hz, 2H), 7.52 (t, J = 7.6 Hz, 2H), 7.43 (t, J = 7.7 Hz, 2H), 7.22 (d, J = 7.1 Hz, 1H), 7.18-7.08 (m, 5H), 5.41 (t, J = 7.6 Hz, 1H), 3.79-3.35 (m, 2H). | 358.2 |
| I-0080 | 4-(1-(1-(hydroxyamino)-1-oxo-3-phenylpropan-2-yl)-1H-indazol-4-yl)benzamide | | 401.2 |

TABLE 2-continued

The following compounds were prepared as depicted in example 3, using the appropriate starting materials.

| No. | Name | Structure/¹H-NMR | LCMS (M + H)⁺ |
|---|---|---|---|
| I-0081 | N-hydroxy-3-phenyl-2-(4-(pyrimidin-5-yl)-1H-indazol-1-yl)propanamide | | 360.1 |
| I-0083 | N-hydroxy-2-(4-(1-methyl-1H-pyrazol-5-yl)-1H-indazol-1-yl)-3-phenylpropanamide | | 362.2 |
| I-0084 | N-hydroxy-2-(4-methyl-1H-indazol-1-yl)-3-phenylpropanamide | | 296.1 |
| I-0085 | N-hydroxy-2-(4-(1-methyl-1,2,3,6-tetrahydropyridin-4-yl)-1H-indazol-1-yl)-3-phenylpropanamide | | 377.2 |

TABLE 2-continued

The following compounds were prepared as depicted in example 3, using the appropriate starting materials.

| No. | Name | Structure/¹H-NMR | LCMS (M + H)⁺ |
|-----|------|------------------|---------------|
| I-0010 | N-hydroxy-2-(5-(1-methyl-1H-pyrazol-5-yl)-1H-indazol-1-yl)-3-phenylpropanamide | | 362.2 |
| I-0012 | N-hydroxy-3-phenyl-2-(5-(pyrimidin-5-yl)-1H-indazol-1-yl)propanamide | | 360.1 |
| I-0013 | N-hydroxy-3-phenyl-2-(5-phenyl-1H-indazol-1-yl)propanamide | | 358.2 |
| I-0014 | 2-(5-(2,6-difluorophenyl)-1H-indazol-1-yl)-N-hydroxy-3-phenylpropanamide | | 394.1 |

TABLE 2-continued

The following compounds were prepared as depicted in example 3, using the appropriate starting materials.

| No. | Name | Structure/¹H-NMR | LCMS (M + H)⁺ |
|---|---|---|---|
| I-0015 | 2-(5-(4-cyanophenyl)-1H-indazol-1-yl)-N-hydroxy-3-phenylpropanamide | | 383.2 |
| I-0016 | N-hydroxy-2-(5-methyl-1H-indazol-1-yl)-3-phenylpropanamide | | 296.1 |
| I-0019 | 2-(5-cyclopropyl-1H-indazol-1-yl)-N-hydroxy-3-phenylpropanamide | | 322.2 |
| I-0103 | N-hydroxy-3-phenyl-2-(5-(1,3,5-trimethyl-1H-pyrazol-4-yl)-1H-indazol-1-yl)propanamide | | 390.2 |
| I-0105 | N-hydroxy-2-(5-(1-methyl-1H-pyrazol-4-yl)-1H-indazol-1-yl)-3-phenylpropanamide | | 362.2 |

TABLE 2-continued

The following compounds were prepared as depicted in example 3, using the appropriate starting materials.

| No. | Name | Structure/¹H-NMR | LCMS (M + H)⁺ |
|---|---|---|---|
| | | ¹H NMR (400 MHz, DMSO) δ 10.89 (s, 1H), 8.10 (s, 1H), 8.01 (s, 1H), 7.84 (s, 2H), 7.70 (d, J = 8.8 Hz, 1H), 7.56 (d, J = 8.8 Hz, 1H), 7.25-6.98 (m, 5H), 5.34 (t, J = 7.6 Hz, 1H), 3.85 (s, 3H), 3.71-3.25 (m, 2H). | |
| I-0104 | N-hydroxy-3-phenyl-2-(5-(pyridin-3-yl)-1H-indazol-1-yl)propanamide | 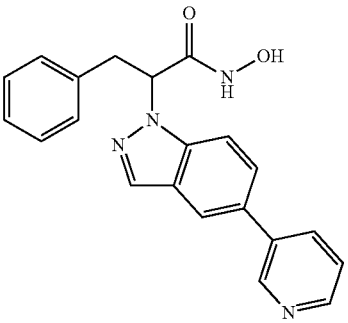 [SMILES: O=C(NO)C(Cc1ccccc1)n1ncc2cc(-c3cccnc3)ccc21] | 359.2 |
| I-0106 | 4-(1-(1-(hydroxyamino)-1-oxo-3-phenylpropan-2-yl)-1H-indazol-5-yl)-N,N-dimethylbenzamide | 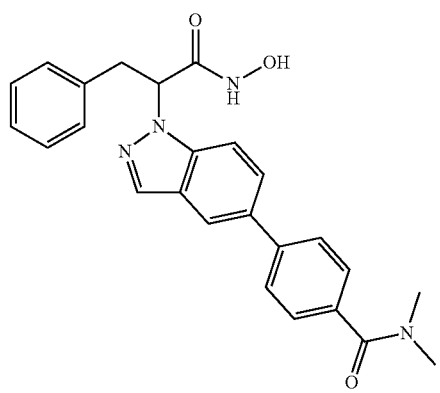 [SMILES: CN(C)C(=O)c1ccc(-c2ccc3c(cnn3C(Cc3ccccc3)C(=O)NO)c2)cc1] | 429.2 |
| I-0107 | (Z)-N-hydroxy-2-(5-(3-(N'-hydroxycarbamimidoyl)phenyl)-1H-indazol-1-yl)-3-phenylpropanamide | 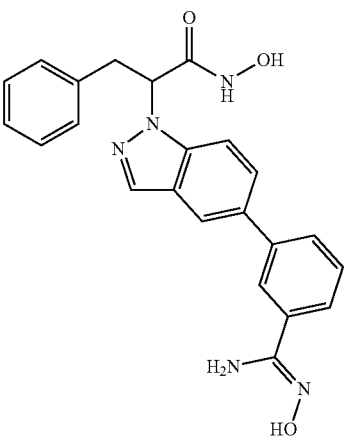 [SMILES: N/C(=N\O)c1cccc(-c2ccc3c(cnn3C(Cc3ccccc3)C(=O)NO)c2)c1] | 416.2 |
| I-0022 | N-hydroxy-3-phenyl-2-(6-phenyl-1H-indazol-1-yl)propanamide | 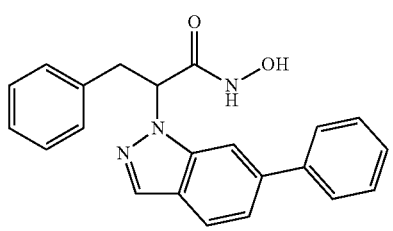 [SMILES: O=C(NO)C(Cc1ccccc1)n1ncc2ccc(-c3ccccc3)cc21] | 358.2 |

TABLE 2-continued

The following compounds were prepared as depicted in example 3, using the appropriate starting materials.

| No. | Name | Structure/¹H-NMR | LCMS (M + H)⁺ |
|-----|------|------------------|---------------|
| I-0023 | N-hydroxy-3-phenyl-2-(6-(pyrimidin-5-yl)-1H-indazol-1-yl)propanamide | | 360.1 |
| I-0143 | N-hydroxy-2-(6-(1-(2-morpholinoethyl)-1H-pyrazol-4-yl)-1H-indazol-1-yl)-3-phenylpropanamide | | 461.2 |
| I-0144 | 2-(6-(5-(4-acetylpiperazin-1-yl)pyridin-3-yl)-1H-indazol-1-yl)-N-hydroxy-3-phenylpropanamide | | 485.2 |
| I-0072 | N-hydroxy-2-(5-(1-methyl-1H-pyrazol-5-yl)-1H-pyrazolo[4,3-b]pyridin-1-yl)-3-phenylpropanamide | | 363.2 |
| I-0073 | N-hydroxy-3-phenyl-2-(5-(pyridin-4-yl)-1H-pyrazolo[4,3-b]pyridin-1-yl)propanamide | | 360.1 |

TABLE 2-continued

The following compounds were prepared as depicted in example 3, using the appropriate starting materials.

| No. | Name | Structure/¹H-NMR | LCMS (M + H)⁺ |
|---|---|---|---|
| I-0074 | N-hydroxy-3-phenyl-2-(5-(pyrimidin-5-yl)-1H-pyrazolo[4,3-b]pyridin-1-yl)propanamide | ¹H NMR (500 MHz, DMSO) δ 9.47 (s, 2H), 9.24 (s, 1H), 8.41-8.36 (m, 2H), 8.13 (d, J = 8.8 Hz, 1H), 7.20-7.03 (m, 5H), 5.51 (m, 1H), 3.57 (m, 2H). | 361.1 |
| I-0075 | N-hydroxy-2-(5-methyl-1H-pyrazolo[4,3-b]pyridin-1-yl)-3-phenylpropanamide | ¹H NMR (500 MHz, DMSO) δ 8.20 (d, J = 8.7 Hz, 1H), 8.15 (s, 1H), 7.31 (d, J = 8.7 Hz, 1H), 7.20-6.99 (m, 5H), 5.42 (t, J = 7.9 Hz, 1H), 3.52 (d, J = 7.9 Hz, 2H), 2.57 (s, 3H). | 297.1 |
| I-0069 | N-hydroxy-2-(4-(1-methyl-1H-pyrazol-5-yl)-1H-pyrazolo[4,3-c]pyridin-1-yl)-3-phenylpropanamide | | 363.2 |
| I-0070 | N-hydroxy-3-phenyl-2-(4-(pyridin-4-yl)-1H-pyrazolo[4,3-c]pyridin-1-yl)propanamide | | 360.1 |

TABLE 2-continued

The following compounds were prepared as depicted in example 3, using the appropriate starting materials.

| No. | Name | Structure/¹H-NMR | LCMS (M + H)⁺ |
|-----|------|------------------|---------------|
| I-0071 | N-hydroxy-3-phenyl-2-(4-(pyrimidin-5-yl)-1H-pyrazolo[4,3-c]pyridin-1-yl)propanamide | ¹H NMR (500 MHz, DMSO) δ 9.44 (s, 2H), 9.35 (s, 1H), 8.73 (s, 1H), 8.51 (d, J = 6.0 Hz, 1H), 7.84 (d, J = 6.0 Hz, 1H), 7.22-7.03 (m, 5H), 5.56 (dd, J = 8.9, 6.7 Hz, 1H), 3.66-3.53 (m, 2H). | 361.1 |
| I-0086 | N-hydroxy-3-phenyl-2-(5-phenyl-1H-pyrazolo[3,4-c]pyridin-1-yl)propanamide | | 359.2 |
| I-0087 | 2-(5-(2,6-difluorophenyl)-1H-pyrazolo[3,4-c]pyridin-1-yl)-N-hydroxy-3-phenylpropanamide | | 395.1 |
| I-0088 | 2-(5-(4-cyanophenyl)-1H-pyrazolo[3,4-c]pyridin-1-yl)-N-hydroxy-3-phenylpropanamide | | 384.1 |

TABLE 2-continued

The following compounds were prepared as depicted in example 3, using the appropriate starting materials.

| No. | Name | Structure/$^1$H-NMR | LCMS (M + H)$^+$ |
|---|---|---|---|
| I-0089 | 4-(1-(1-(hydroxyamino)-1-oxo-3-phenylpropan-2-yl)-1H-pyrazolo[3,4-c]pyridin-5-yl)benzamide | | 402.2 |
| I-0090 | N-hydroxy-2-(5-(1-methyl-1H-pyrazol-5-yl)-1H-pyrazolo[3,4-c]pyridin-1-yl)-3-phenylpropanamide | | 363.2 |
| I-0091 | N-hydroxy-2-(5-(1-methyl-1H-pyrazol-4-yl)-1H-pyrazolo[3,4-c]pyridin-1-yl)-3-phenylpropanamide | | 363.2 |
| I-0092 | N-hydroxy-3-phenyl-2-(5-(pyrimidin-5-yl)-1H-pyrazolo[3,4-c]pyridin-1-yl)propanamide | | 361.1 |

TABLE 2-continued

The following compounds were prepared as depicted in example 3, using the appropriate starting materials.

| No. | Name | Structure/¹H-NMR | LCMS (M + H)⁺ |
|---|---|---|---|
| I-0094 | N-hydroxy-2-(5-(2-methoxypyrimidin-5-yl)-1H-pyrazolo[3,4-c]pyridin-1-yl)-3-phenylpropanamide | | 391.2 |
| I-0095 | N-hydroxy-3-phenyl-2-(5-(pyridin-3-yl)-1H-pyrazolo[3,4-c]pyridin-1-yl)propanamide | | 360.1 |
| I-0096 | N-hydroxy-2-(5-(6-methoxypyridin-3-yl)-1H-pyrazolo[3,4-c]pyridin-1-yl)-3-phenylpropanamide | | 390.2 |
| I-0097 | N-hydroxy-3-phenyl-2-(5-(pyridin-4-yl)-1H-pyrazolo[3,4-c]pyridin-1-yl)propanamide | | 360.1 |

TABLE 2-continued

The following compounds were prepared as depicted in example 3, using the appropriate starting materials.

| No. | Name | Structure/$^1$H-NMR | LCMS (M + H)$^+$ |
|---|---|---|---|
| I-0098 | 2-(5-cyclopropyl-1H-pyrazolo[3,4-c]pyridin-1-yl)-N-hydroxy-3-phenylpropanamide | | 323.2 |
| I-0116 | N-hydroxy-3-phenyl-2-(5-phenyl-1H-pyrazolo[3,4-b]pyridin-1-yl)propanamide | | 359.2 |
| I-0117 | 2-(5-(4-cyanophenyl)-1H-pyrazolo[3,4-b]pyridin-1-yl)-N-hydroxy-3-phenylpropanamide | | 384.1 |
| I-0118 | 4-(1-(1-(hydroxyamino)-1-oxo-3-phenylpropan-2-yl)-1H-pyrazolo[3,4-b]pyridin-5-yl)benzamide | | 402.2 |

TABLE 2-continued

The following compounds were prepared as depicted in example 3, using the appropriate starting materials.

| No. | Name | Structure/$^1$H-NMR | LCMS (M + H)$^+$ |
|---|---|---|---|
| I-0119 | N-hydroxy-2-(5-(1-methyl-1H-pyrazol-5-yl)-1H-pyrazolo[3,4-b]pyridin-1-yl)-3-phenylpropanamide | | 363.2 |
| I-0120 | N-hydroxy-2-(5-(1-methyl-1H-pyrazol-4-yl)-1H-pyrazolo[3,4-b]pyridin-1-yl)-3-phenylpropanamide | | 363.2 |
| I-0121 | N-hydroxy-3-phenyl-2-(5-(pyrimidin-5-yl)-1H-pyrazolo[3,4-b]pyridin-1-yl)propanamide | | 361.1 |
| I-0130 | 2-(5-(3-cyanophenyl)-1H-pyrazolo[3,4-b]pyridin-1-yl)-N-hydroxy-3-phenylpropanamide | | 384.1 |

TABLE 2-continued

The following compounds were prepared as depicted in example 3, using the appropriate starting materials.

| No. | Name | Structure/¹H-NMR | LCMS (M + H)⁺ |
|---|---|---|---|
| I-0131 | 3-(1-(1-(hydroxyamino)-1-oxo-3-phenylpropan-2-yl)-1H-pyrazolo[3,4-b]pyridin-5-yl)benzamide | | 402.2 |
| I-0132 | N-hydroxy-3-phenyl-2-(5-(pyridin-3-yl)-1H-pyrazolo[3,4-b]pyridin-1-yl)propanamide | | 360.1 |
| I-0133 | N-hydroxy-3-phenyl-2-(5-(pyridin-4-yl)-1H-pyrazolo[3,4-b]pyridin-1-yl)propanamide | | 360.1 |
| I-0147 | N-hydroxy-2-(4-(4-(methoxymethyl)phenyl)-2H-indazol-2-yl)-3-phenylpropanamide | | 402.2 |

TABLE 2-continued

The following compounds were prepared as depicted in example 3, using the appropriate starting materials.

| No. | Name | Structure/¹H-NMR | LCMS (M + H)⁺ |
|---|---|---|---|
| I-0146 | N-hydroxy-2-(4-(6-isopropoxypyridin-3-yl)-2H-indazol-2-yl)-3-phenylpropanamide | | 417.2 |
| I-0148 | N-hydroxy-2-(4-(4-(4-methylpiperazin-1-yl)phenyl)-2H-indazol-2-yl)-3-phenylpropanamide | ¹H NMR (400 MHz, DMSO) δ 11.05 (s, 1H), 9.63 (s, 1H), 9.10 (s, 1H), 8.53 (s, 1H), 7.60 (d, J = 8.7 Hz, 2H), 7.50 (d, J = 8.6 Hz, 1H), 7.28 (dd, J = 8.6, 7.0 Hz, 1H), 7.25-7.09 (m, 6H), 5.36 (t, J = 7.8 Hz, 1H), 3.97 (d, J = 12.9 Hz, 2H), 3.69-3.39 (m, 4H), 3.20 (d, J = 11.2 Hz, 2H), 3.04 (t, J = 12.0 Hz, 2H), 2.88 (s, 3H). | 456.2 |
| I-0149 | N-hydroxy-2-(4-(6-(4-methylpiperazin-1-yl)pyridin-3-yl)-2H-indazol-2-yl)-3-phenylpropanamide | 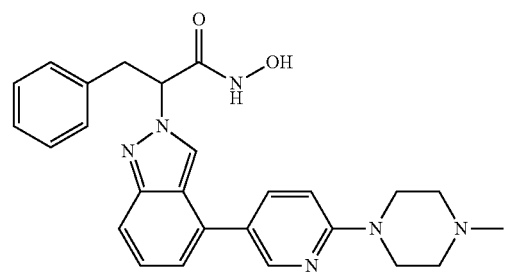 [SMILES: CN1CCN(c2ccc(-c3cccc4nn(C(Cc5ccccc5)C(=O)NO)cc34)cn2)CC1] ¹H NMR (400 MHz, DMSO) δ 11.05 (s, 1H), 9.70 (s, 1H), 9.12 (s, 1H), 8.68-8.44 (m, 2H), 7.96 (dd, J = 8.8, 2.4 Hz, 1H), 7.54 (d, J = 8.7 Hz, 1H), 7.36-7.25 (m, 1H), 7.25-7.01 (m, 5H), 5.36 (t, J = 7.9 Hz, 1H), 4.52 (d, J = 14.2 Hz, 2H), 3.73-3.36 (m, 4H), 3.36-3.01 (m, 4H), 2.87 (d, J = 4.0 Hz, 3H). | 457.2 |
| I-0057 | N-hydroxy-2-(4-(1-methyl-1,2,3,6-tetrahydropyridin-4-yl)-2H-indazol-2-yl)-3-phenylpropanamide | 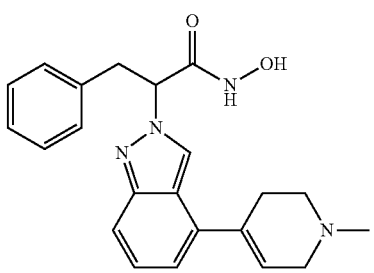 [SMILES: CN1CC=C(c2cccc3nn(C(Cc4ccccc4)C(=O)NO)cc23)CC1] | 377.2 |

TABLE 2-continued

The following compounds were prepared as depicted in example 3, using the appropriate starting materials.

| No. | Name | Structure/$^1$H-NMR | LCMS (M + H)$^+$ |
|---|---|---|---|
| I-0058 | N-hydroxy-3-phenyl-2-(4-(pyridin-4-yl)-2H-indazol-2-yl)propanamide | | 359.2 |
| I-0063 | N-hydroxy-3-phenyl-2-(4-(pyrimidin-5-yl)-2H-indazol-2-yl)propanamide | $^1$H NMR (400 MHz, DMSO) δ 11.02 (s, 1H), 9.26 (s, 1H), 9.15 (s, 2H), 8.82 (s, 1H), 7.68 (d, J = 8.4 Hz, 1H), 7.42-7.36 (m, 1H), 7.36-7.28 (m, 1H), 7.27-7.04 (m, 5H), 5.37 (t, J = 7.6 Hz, 1H), 3.62 (dd, J = 14.0, 7.0 Hz, 1H), 3.53 (dd, J = 14.0, 7.0 Hz, 1H). | 360.1 |
| I-0060 | N-hydroxy-3-phenyl-2-(4-phenyl-2H-indazol-2-yl)propanamide | | 358.2 |
| I-0061 | N-hydroxy-2-(4-(1-methyl-1H-pyrazol-5-yl)-2H-indazol-2-yl)-3-phenylpropanamide | | 362.2 |

TABLE 2-continued

The following compounds were prepared as depicted in example 3, using the appropriate starting materials.

| No. | Name | Structure/¹H-NMR | LCMS (M + H)⁺ |
|---|---|---|---|
| I-0062 | 2-(4-cyclopropyl-2H-indazol-2-yl)-N-hydroxy-3-phenylpropanamide | | 322.2 |
| I-0064 | N-hydroxy-2-(4-methyl-2H-indazol-2-yl)-3-phenylpropanamide | | 296.1 |
| I-0049 | N-hydroxy-2-(5-methyl-2H-indazol-2-yl)-3-phenylpropanamide | | 296.1 |
| I-0050 | N-hydroxy-3-phenyl-2-(5-(pyridin-4-yl)-2H-indazol-2-yl)propanamide | ¹H NMR (400 MHz, DMSO) δ 11.10 (s, 1H), 8.80 (d, J = 5.9 Hz, 2H), 8.74 (s, 1H), 8.40 (s, 1H), 8.14 (d, J = 5.3 Hz, 2H), 7.88-7.62 (m, 2H), 7.19 (M, 5H), 5.50-5.28 (m, 1H), 3.73-3.35 (m, 2H). | 359.2 |

TABLE 2-continued

The following compounds were prepared as depicted in example 3, using the appropriate starting materials.

| No. | Name | Structure/$^1$H-NMR | LCMS (M + H)$^+$ |
|---|---|---|---|
| I-0033 | (Z)-N-hydroxy-2-(5-(4-(N'-hydroxy-carbamimidoyl)phenyl)-2H-indazol-2-yl)-3-phenylpropanamide | | 416.2 |
| I-0051 | N-hydroxy-3-phenyl-2-(5-(pyrimidin-5-yl)-2H-indazol-2-yl)propanamide | | 360.1 |
| I-0034 | N-hydroxy-2-(5-(1-methyl-1H-pyrazol-5-yl)-2H-indazol-2-yl)-3-phenylpropanamide | $^1$H NMR (400 MHz, DMSO) δ 11.07 (s, 1H), 8.60 (s, 1H), 7.84 (s, 1H), 7.65 (d, J = 9.0 Hz, 1H), 7.45 (d, J = 1.7 Hz, 1H), 7.34 (dd, J = 9.0, 1.4 Hz, 1H), 7.23 (d, J = 4.3 Hz, 3H), 7.16 (dd, J = 9.3, 4.7 Hz, 2H), 6.37 (d, J = 1.7 Hz, 1H), 5.38 (t, J = 7.8 Hz, 1H), 3.84 (s, 3H), 3.53 (m, 2H). | 362.2 |

TABLE 2-continued

The following compounds were prepared as depicted in example 3, using the appropriate starting materials.

| No. | Name | Structure/$^1$H-NMR | LCMS (M + H)$^+$ |
|---|---|---|---|
| I-0035 | N-hydroxy-2-(5-(2-methoxypyrimidin-5-yl)-2H-indazol-2-yl)-3-phenylpropanamide | | 390.2 |
| I-0036 | N-hydroxy-3-phenyl-2-(5-phenyl-2H-indazol-2-yl)propanamide | | 358.2 |
| I-0006 | N-hydroxy-3-phenyl-2-(6-phenyl-2H-indazol-2-yl)propanamide | $^1$H NMR (400 MHz, CD3OD) δ 8.39 (s, 1H), 7.77 (d, J = 9.0 Hz, 2H), 7.72-7.63 (m, 2H), 7.47 (t, J = 7.6 Hz, 2H), 7.42-7.32 (m, 2H), 7.30-7.11 (m, 5H), 5.30 (t, J = 7.8 Hz, 1H), 3.62 (m, 2H). | 358.2 |

TABLE 2-continued

The following compounds were prepared as depicted in example 3, using the appropriate starting materials.

| No. | Name | Structure/¹H-NMR | LCMS (M + H)⁺ |
|---|---|---|---|
| I-0007 | N-hydroxy-3-phenyl-2-(6-(pyrimidin-5-yl)-2H-indazol-2-yl)propanamide | ¹H NMR (400 MHz, DMSO) δ 11.09 (s, 11), 9.18 (d, J = 4.2 Hz, 3H), 8.59 (s, 1H), 8.03 (s, 1H), 7.86 (d, J = 8.7 Hz, 1H), 7.44 (dd, J = 8.7, 1.4 Hz, 1H), 7.25-7.08 (m, 5H), 5.43-5.34 (m, 1H), 3.54 (m, 2H). | 360.1 |
| I-0008 | N-hydroxy-3-phenyl-2-(6-(pyridin-3-yl)-2H-indazol-2-yl)propanamide | | 359.2 |
| I-0040 | N-hydroxy-2-(6-methyl-2H-indazol-2-yl)-3-phenylpropanamide | | 296.1 |

TABLE 2-continued

The following compounds were prepared as depicted in example 3, using the appropriate starting materials.

| No. | Name | Structure/$^1$H-NMR | LCMS (M + H)$^+$ |
|---|---|---|---|
| I-0047 | N-hydroxy-2-(6-(1-methyl-1H-pyrazol-5-yl)-2H-indazol-2-yl)-3-phenylpropanamide | | 362.2 |
| I-0066 | N-hydroxy-3-phenyl-2-(7-phenyl-2H-indazol-2-yl)propanamide | | 358.2 |
| I-0067 | N-hydroxy-2-(7-(1-methyl-1H-pyrazol-5-yl)-2H-indazol-2-yl)-3-phenylpropanamide | | 362.2 |
| I-0078 | N-hydroxy-2-(7-methyl-2H-indazol-2-yl)-3-phenylpropanamide | | 296.1 |
| I-0101 | N-hydroxy-2-(7-(1-methyl-1,2,3,6-tetrahydropyridin-4-yl)-2H-indazol-2-yl)-3-phenylpropanamide | | 377.2 |

TABLE 2-continued

The following compounds were prepared as depicted in example 3, using the appropriate starting materials.

| No. | Name | Structure/¹H-NMR | LCMS (M + H)⁺ |
|---|---|---|---|
| I-0109 | N-hydroxy-2-(7-(1-methyl-1H-pyrazol-4-yl)-2H-indazol-2-yl)-3-phenylpropanamide | | 362.2 |
| I-0110 | 4-(2-(1-(hydroxyamino)-1-oxo-3-phenylpropan-2-yl)-2H-indazol-7-yl)-N,N-dimethylbenzamide | ¹H NMR (400 MHz, DMSO) δ 11.07 (s, 1H), 8.69 (s, 1H), 8.05 (d, J = 8.3 Hz, 2H), 7.73 (d, J = 7.9 Hz, 1H), 7.49 (d, J = 8.3 Hz, 3H), 7.28-7.13 (m, 6H), 5.42 (dd, J = 8.9, 6.8 Hz, 1H), 3.58 (dd, J = 14.1, 8.9 Hz, 1H), 3.49 (dd, J = 14.2, 6.7 Hz, 1H), 3.00 (s, 6H). | 429.2 |
| I-0111 | N-hydroxy-3-phenyl-2-(7-(1,3,5-trimethyl-1H-pyrazol-4-yl)-2H-indazol-2-yl)propanamide | | 390.2 |
| I-0198 | N-hydroxy-3-phenyl-2-(7-(pyrimidin-5-yl)-2H-pyrazolo[3,4-c]pyridin-2-yl)propanamide | | 361.1 |

TABLE 2-continued
The following compounds were prepared as depicted in example 3, using the appropriate starting materials.
| No. | Name | Structure/¹H-NMR | LCMS (M + H)⁺ |
|---|---|---|---|
| I-0199 | N-hydroxy-2-(7-(1-methyl-1H-pyrazol-5-yl)-2H-pyrazolo[3,4-c]pyridin-2-yl)-3-phenylpropanamide | | 363.2 |
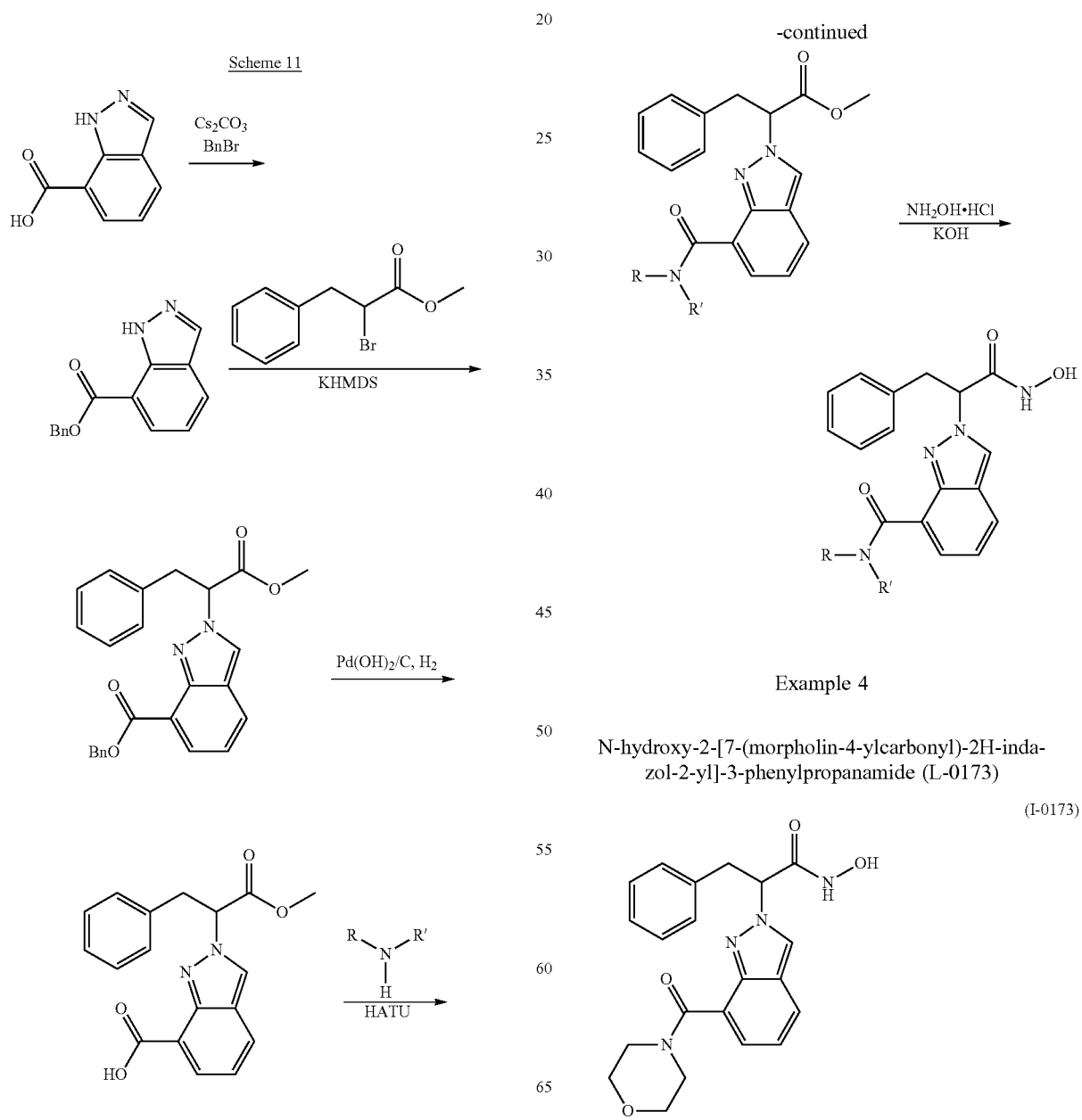
Example 4
N-hydroxy-2-[7-(morpholin-4-ylcarbonyl)-2H-indazol-2-yl]-3-phenylpropanamide (I-0173)

Step 1. Benzyl 1H-indazole-7-carboxylate

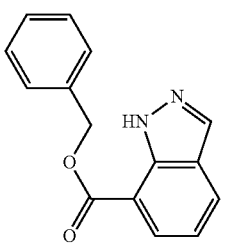 [SMILES: O=C(OCc1ccccc1)c1cccc2cn[nH]c12]

To a mixture of 1H-indazole-7-carboxylic acid (1.700 g, 10.48 mmol), Cs$_2$CO$_3$ (3.756 g, 11.53 mmol) and NaI (272.4 mg, 1.817 mmol) was added DMF (24.0 mL) followed by benzyl bromide (2.146 g, 12.55 mmol) After stirring at room temperature for 1 h, the reaction mixture was diluted with EtOAc, washed with water and brine. The organic layer was dried over anhydrous Na$_2$SO$_4$, filtered and concentrated. The resulting residue was purified on silica gel (120 g, 0-100% EtOAc in hexanes) to give the desired product as a white solid (1.91 g, 72%). LCMS calculated for C$_{15}$H$_{13}$N$_2$O$_2$ (M+H)$^+$: m/z=253.1; found 253.1.

Step 2. Benzyl 2-(1-benzyl-2-methoxy-2-oxoethyl)-2H-indazole-7-carboxylate

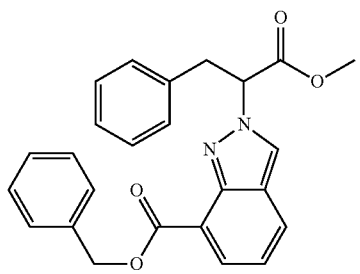 [SMILES: COC(=O)C(Cc1ccccc1)n1cc2cccc(C(=O)OCc3ccccc3)c2n1]

To a solution of benzyl 1H-indazole-7-carboxylate (1189 mg, 4.713 mmol) in THF (15.0 mL) at −78° C. was added 1.0 M KHMDS in THF (5.40 mL, 5.40 mmol) dropwise. The mixture was allowed to warm to 0° C. and stirred for 1 h. Then the reaction was cooled back to −78° C., and a solution of methyl 2-bromo-3-phenylpropanoate (1.607 g, 6.610 mmol) in THF (5.0 mL) was added dropwise. The reaction was allowed to warm to room temperature and stirred for 16 h. The mixture was then diluted with EtOAc, washed with water and brine. The organic layer was dried over anhydrous Na$_2$SO$_4$, filtered and concentrated. The resulting residue was purified on silica gel (120 g, 0-100% EtOAc in hexanes) to give the desired product as a white solid (1.54 g, 79%). LCMS calculated for C$_{25}$H$_{23}$N$_2$O$_4$ (M+H)$^-$: m/z=415.2; found 415.1.

Step 3. 2-(1-benzyl-2-methoxy-2-oxoethyl)-2H-indazole-7-carboxylic acid

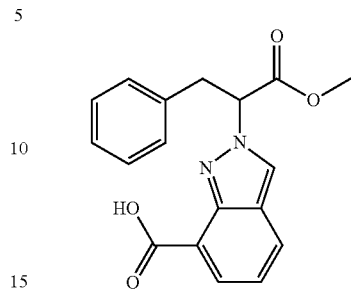

To a solution of benzyl 2-(1-benzyl-2-methoxy-2-oxoethyl)-2H-indazole-7-carboxylate (1.543 g, 3.723 mmol) in MeOH (25.0 mL) under N$_2$ atmosphere was added 20 wt % Pd(OH)$_2$ on carbon (652.5 mg, 0.9292 mmol). The mixture was purged with H$_2$ and stirred under H$_2$ atmosphere (1 atm) for 5 h. The reaction was then filtered through a pad of Celite (eluted with MeOH). The filtrate was concentrated to give the desired product as a white foamy solid (1.125 g, 93%) which was used directly in the next step without further purification. LCMS calculated for C$_{18}$H$_{17}$N$_2$O$_4$ (M+H)$^+$: m/z=325.1; found 325.1.

Step 4. N-hydroxy-2-[7-(morpholin-4-ylcarbonyl)-2H-indazol-2-yl]-3-phenylpropanamide To a vial containing HATU (32.6 mg, 0.0857 mmol) was added a solution of 2-(1-benzyl-2-methoxy-2-oxoethyl)-2H-indazole-7-carboxylic acid (27.9 mg, 0.0860 mmol) in DMF (0.50 mL) followed by N,N-diisopropylethylamine (50.0 μL, 0.287 mmol). The reaction mixture was stirred at room temperature for 20 min, and then a solution of morpholine (8.0 mg, 0.092 mmol) in DMF (0.5 mL) was added. The reaction was stirred at room temperature for 30 min.

To another vial containing hydroxylamine hydrochloride (90.2 mg, 1.30 mmol) was added MeOH (0.20 mL) followed by a solution of KOH (148.8 mg, 2.652 mmol) in MeOH (0.75 mL). The resulting white suspension was stirred at room temperature for 30 min, and then cooled to 0° C. The above DMF solution was added. The reaction mixture was stirred at 0° C. for 30 min, and then neutralized with 0.60 mL 4.0 M HCl (aq). The mixture was diluted with MeOH and filtered. The filtrate was purified using RP-HPLC (Waters SunFire™ C18 column, 30 mm×100 mm, 5 μm particle size, eluting with a gradient of acetonitrile/water containing 0.1% TFA, at flow rate of 60 mL/min) to afford compound (I-0173) as a white solid (25.2 mg). LCMS calculated for C$_{21}$H$_{23}$N$_4$O$_4$ (M+H)$^+$: m/z=395.2; found 395.1. IC50: 1171 nM.

TABLE 3

The compounds in Table 3 were prepared in accordance with the synthetic protocols set forth in Scheme 11 and Example 4, using the appropriate starting materials.

| No. | Name | Structure | LCMS (M + H)+ |
|---|---|---|---|
| I-0172 | methyl 2-(7-(4,4-difluoropiperidine-1-carbonyl)-2H-indazol-2-yl)-3-phenylpropanoate | 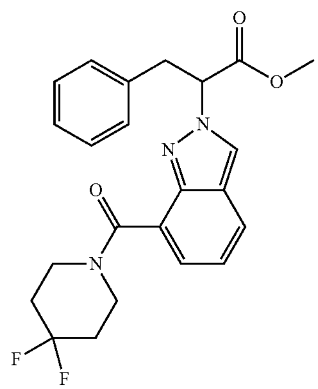 [SMILES: COC(=O)C(Cc1ccccc1)n1cc2cccc(C(=O)N3CCC(F)(F)CC3)c2n1] | 429.2 |
| I-0174 | 2-(7-(2-oxa-7-azaspiro[3.5]nonane-7-carbonyl)-2H-indazol-2-yl)-N-hydroxy-3-phenylpropanamide | 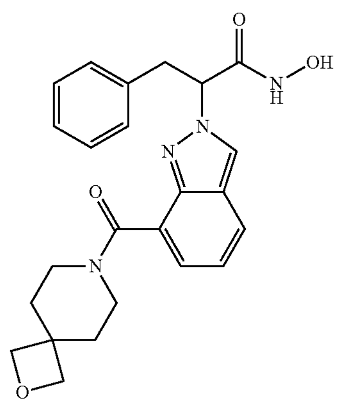 [SMILES: O=C(NO)C(Cc1ccccc1)n1cc2cccc(C(=O)N3CCC4(CC3)COC4)c2n1] | 435.2 |
| I-0175 | 2-(7-(3-oxa-9-azaspiro[5.5]undecane-9-carbonyl)-2H-indazol-2-yl)-N-hydroxy-3-phenylpropanamide | 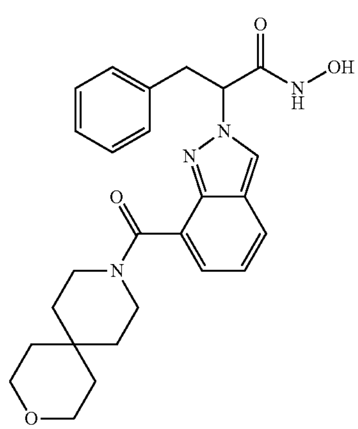 [SMILES: O=C(NO)C(Cc1ccccc1)n1cc2cccc(C(=O)N3CCC4(CCOCC4)CC3)c2n1] | 463.2 |

TABLE 3-continued

The compounds in Table 3 were prepared in accordance with the synthetic protocols set forth in Scheme 11 and Example 4, using the appropriate starting materials.

| No. | Name | Structure | LCMS (M + H)+ |
|---|---|---|---|
| I-0176 | 2-(1-(hydroxyamino)-1-oxo-3-phenylpropan-2-yl)-N-(tetrahydro-2H-pyran-4-yl)-2H-indazole-7-carboxamide | 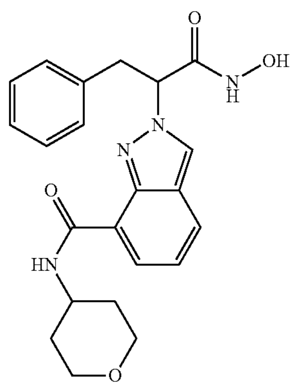 [SMILES: O=C(NC1CCOCC1)c1cccc2cn(C(Cc3ccccc3)C(=O)NO)nc12] | 409.2 |
| I-0177 | 2-(1-(hydroxyamino)-1-oxo-3-phenylpropan-2-yl)-N-((tetrahydro-2H-pyran-4-yl)methyl)-2H-indazole-7-carboxamide | 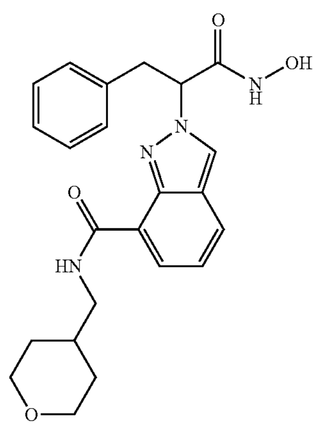 [SMILES: O=C(NCC1CCOCC1)c1cccc2cn(C(Cc3ccccc3)C(=O)NO)nc12] | 423.2 |
| I-0178 | 2-(1-(hydroxyamino)-1-oxo-3-phenylpropan-2-yl)-N-(2-(tetrahydro-2H-pyran-4-yl)ethyl)-2H-indazole-7-carboxamide | 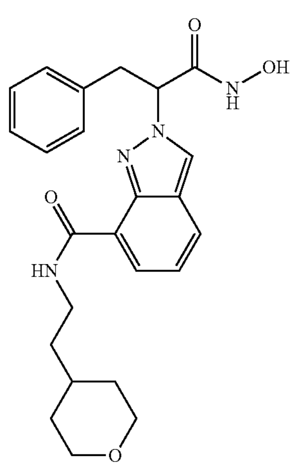 [SMILES: O=C(NCCC1CCOCC1)c1cccc2cn(C(Cc3ccccc3)C(=O)NO)nc12] | 437.2 |

TABLE 3-continued
The compounds in Table 3 were prepared in accordance with the synthetic protocols set forth in Scheme 11 and Example 4, using the appropriate starting materials.
| No. | Name | Structure | LCMS (M + H)+ |
|---|---|---|---|
| I-0179 | 2-(1-(hydroxyamino)-1-oxo-3-phenylpropan-2-yl)-N-(2-morpholinoethyl)-2H-indazole-7-carboxamide | 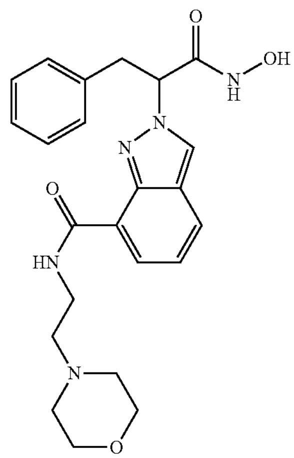 [SMILES: O=C(NCCN1CCOCC1)c1cccc2cn(C(Cc3ccccc3)C(=O)NO)nc12] | 438.2 |
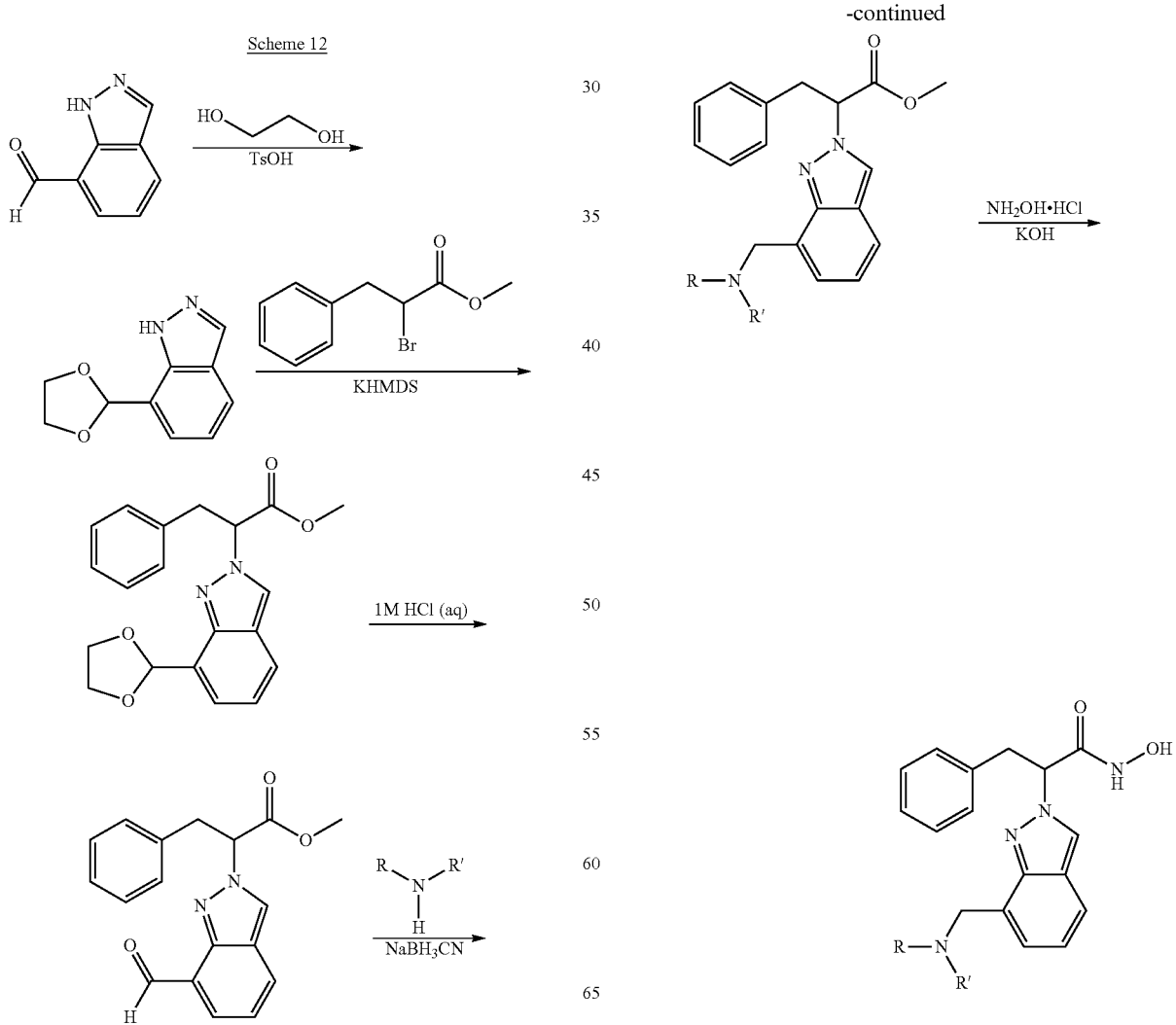
Scheme 12

Example 5

2-{7-[(Cyclopropylamino)methyl]-2H-indazol-2-yl}-N-hydroxy-3-phenylpropanamide (I-0180)

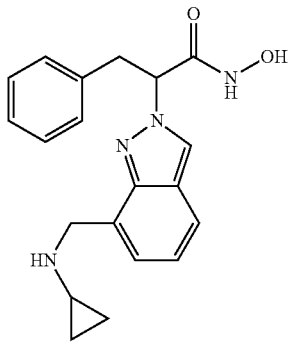 [SMILES: O=C(NO)C(Cc1ccccc1)n1cc2cccc(CNC3CC3)c2n1]

Step 1. 7-(1,3-Dioxolan-2-yl)-1H-indazole

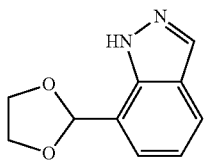 [SMILES: c1cc(C2OCCO2)c2[nH]ncc2c1]

To a solution of 1,2-ethanediol (2.406 g, 38.76 mmol) in Toluene (90.0 mL) was added 1H-indazole-7-carbaldehyde (1.812 g, 12.40 mmol) followed by p-toluenesulfonic acid monohydrate (56.2 mg, 0.295 mmol). The reaction was heated to reflux using a Dean-Stark trap for 16 h. After cooling to the room temperature, the mixture was washed with 1 M $Na_2CO_3$ (aq), and brine. The organic layer was dried over $Na_2SO_4$, filtered and concentrated. The residue was purified on silica gel (120 g, 0-100% EtOAc in hexanes) to give the desired product as a pale yellow solid (1.727 g, 73%). LCMS calculated for $C_{10}H_{11}N_2O_2$ $(M+H)^+$: m/z=191.1; found 191.1.

Step 2. Methyl 2-[7-(1,3-dioxolan-2-yl)-2H-indazol-2-yl]-3-phenylpropanoate

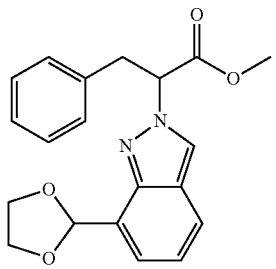 [SMILES: COC(=O)C(Cc1ccccc1)n1cc2cccc(C3OCCO3)c2n1]

To a solution of 7-(1,3-dioxolan-2-yl)-1H-indazole (1.727 g, 9.080 mmol) in THF (30.0 mL) at −78° C. was added 1.0 M KHMDS in THF (10.5 mL, 10.5 mmol) dropwise. The mixture was allowed to warm to 0° C. and stirred for 1 h. The reaction was then cooled back to −78° C. A solution of methyl 2-bromo-3-phenylpropanoate (3.109 g, 12.79 mmol) in THF (10.0 mL) was added dropwise. The reaction mixture was allowed to warm to room temperature and stirred for 16 h. The mixture was then diluted with EtOAc, washed with water and brine. The organic layer was dried over anhydrous $Na_2SO_4$, filtered and concentrated. The resulting residue was purified on silica gel (120 g, 0-100% EtOAc in hexanes) to give the desired product as a white solid (2.36 g, 74%). LCMS calculated for $C_{20}H_{21}N_2O_4$ $(M+H)^+$; m/z=353.2; found 353.1.

Step 3. Methyl 2-(7-formyl-2H-indazol-2-yl)-3-phenylpropanoate

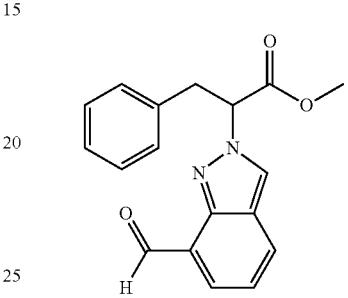

To a solution of methyl 2-[7-(1,3-dioxolan-2-yl)-2H-indazol-2-yl]-3-phenylpropanoate (827.1 mg, 2.347 mmol) in THF (50.0 mL) was added 50.0 mL 1.0 M HCl (aq). After stirring at room temperature for 30 min, the reaction mixture was diluted with EtOAc and washed with sat. $NaHCO_3$ (aq) and brine. The organic layer was dried over anhydrous $Na_2SO_4$, filtered and concentrated to give the desired product (756.2 mg) which was used directly in the next step without further purification. LCMS calculated for $C_{18}H_{17}N_2O_3$ $(M+H)^+$: m/z=309.1; found 309.1.

Step 4. 2-{7-[(Cyclopropylamino)methyl]-2H-indazol-2-yl}-N-hydroxy-3-phenylpropanamide To a vial containing a solution of methyl 2-(7-formyl-2H-indazol-2-yl)-3-phenylpropanoate (36.2 mg, 0.117 mmol) in MeOH (1.00 mL) was added cyclopropylamine (20.0 mg, 0.350 mmol) followed by acetic acid (10.8 mg, 0.180 mmol). The mixture was stirred at room temperature for 3 h. Sodium cyanoborohydride (16.5 mg, 0.262 mmol) was added. The reaction mixture was stirred at room temperature for 16 h.

To another vial containing hydroxylamine hydrochloride (127.4 mg, 1.833 mmol) was added MeOH (0.20 mL) followed by a solution of KOH (199.7 mg, 3.559 mmol) in MeOH (1.00 mL). The resulting white suspension was stirred at room temperature for 30 min, and then cooled to 0° C. The above sodium cyanoborohydride reaction mixture was added. After stirring at 0° C. for 30 min, the reaction was neutralized with 0.80 mL 4.0 M HCl (aq). The mixture was diluted with MeOH and filtered. The filtrate was purified using RP-HPLC (Waters SunFire™ C18 column, 30 mm×100 mm, 5 μm particle size, eluting with a gradient of acetonitrile/water containing 0.1% TFA, at flow rate of 60 mL/min) to afford compound (I-0180) as a white solid (32.3 mg). LCMS calculated for $C_{20}H_{23}N_4O_2$ $(M+H)^+$: m/z=351.2; found 351.1. IC50: 469 nM.

TABLE 4

The compounds listed in Table 4 were prepared in accordance with the synthetic protocols set forth in Scheme 12 and Example 5, using the appropriate starting materials.

| No. | Name | Structure | LCMS (M + H)+ |
|---|---|---|---|
| I-0181 | 2-(7-((cyclopropylmethylamino)methyl)-2H-indazol-2-yl)-N-hydroxy-3-phenylpropanamide | 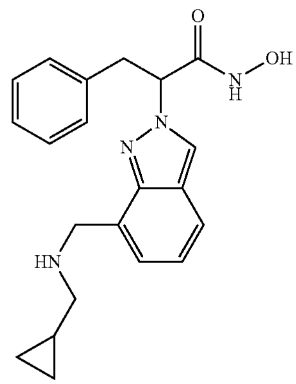 [SMILES: O=C(NO)C(Cc1ccccc1)n1cc2cccc(CNCC3CC3)c2n1] | 365.2 |
| I-0182 | N-hydroxy-3-phenyl-2-(7-((tetrahydro-2H-pyran-4-ylamino)methyl)-2H-indazol-2-yl)propanamide | 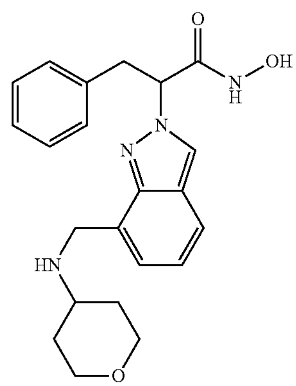 [SMILES: O=C(NO)C(Cc1ccccc1)n1cc2cccc(CNC3CCOCC3)c2n1] | 395.2 |
| I-0183 | N-hydroxy-2-(7-(morpholinomethyl)-2H-indazol-2-yl)-3-phenylpropanamide | 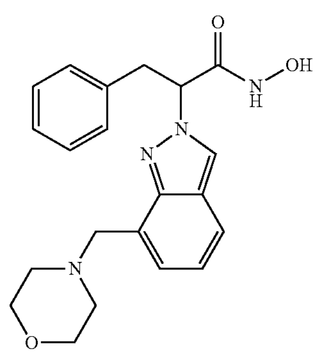 [SMILES: O=C(NO)C(Cc1ccccc1)n1cc2cccc(CN3CCOCC3)c2n1] | 381.2 |
| I-0184 | N-hydroxy-2-(7-((4-methoxypiperidin-1-yl)methyl)-2H-indazol-2-yl)-3-phenylpropanamide | 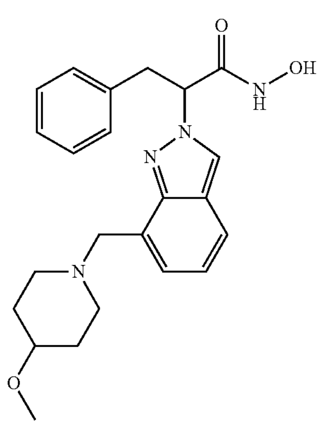 [SMILES: COC1CCN(Cc2cccc3cn(C(Cc4ccccc4)C(=O)NO)nc23)CC1] | 409.2 |

TABLE 4-continued

The compounds listed in Table 4 were prepared in accordance with the synthetic protocols set forth in Scheme 12 and Example 5, using the appropriate starting materials.

| No. | Name | Structure | LCMS (M + H)+ |
|---|---|---|---|
| I-0185 | N-hydroxy-2-(7-((4-morpholinopiperidin-1-yl)methyl)-2H-indazol-2-yl)-3-phenylpropanamide | 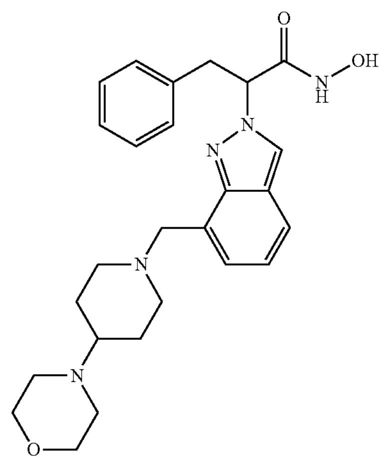 [SMILES: O=C(NO)C(Cc1ccccc1)n1cc2cccc(CN3CCC(N4CCOCC4)CC3)c2n1] | 464.3 |
| I-0186 | 2-(7-(2-oxa-7-azaspiro[3.5]nonan-7-ylmethyl)-2H-indazol-2-yl)-N-hydroxy-3-phenylpropanamide | 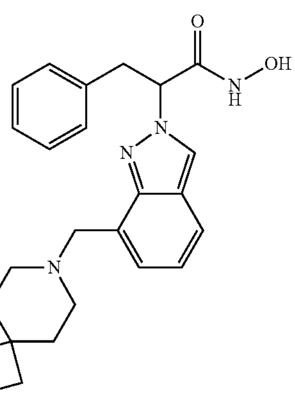 | 421.2 |
| I-0187 | 2-(7-(3-oxa-9-azaspiro[5.5]undecan-9-ylmethyl)-2H-indazol-2-yl)-N-hydroxy-3-phenylpropanamide | 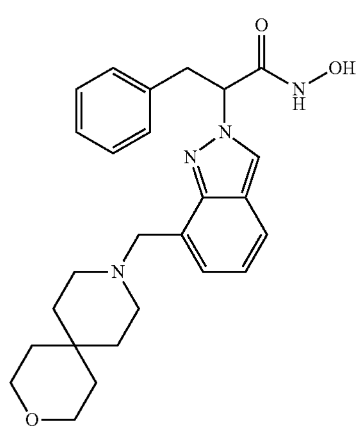 [SMILES: O=C(NO)C(Cc1ccccc1)n1cc2cccc(CN3CCC4(CCOCC4)CC3)c2n1] | 449.3 |

TABLE 4-continued

The compounds listed in Table 4 were prepared in accordance with the synthetic protocols set forth in Scheme 12 and Example 5, using the appropriate starting materials.

| No. | Name | Structure | LCMS (M + H)+ |
|---|---|---|---|
| I-0188 | N-hydroxy-2-(7-((4-methylpiperazin-1-yl)methyl)-2H-indazol-2-yl)-3-phenylpropanamide | 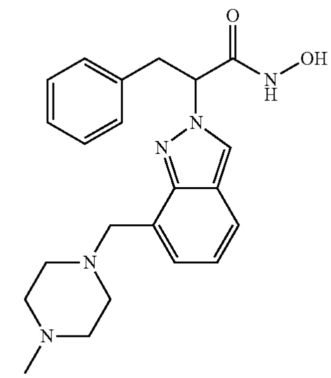 [SMILES: CN1CCN(Cc2cccc3cn(C(Cc4ccccc4)C(=O)NO)nc23)CC1] | 394.2 |
| I-0189 | 2-(7-((4,4-difluoropiperidin-1-yl)methyl)-2H-indazol-2-yl)-N-hydroxy-3-phenylpropanamide | 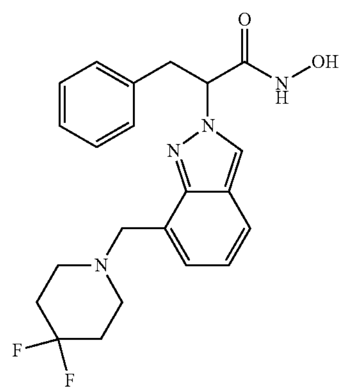 [SMILES: O=C(NO)C(Cc1ccccc1)n1cc2cccc(CN3CCC(F)(F)CC3)c2n1] | 415.2 |
| I-0190 | 2-(7-((3,3-difluoropiperidin-1-yl)methyl)-2H-indazol-2-yl)-N-hydroxy-3-phenylpropanamide | 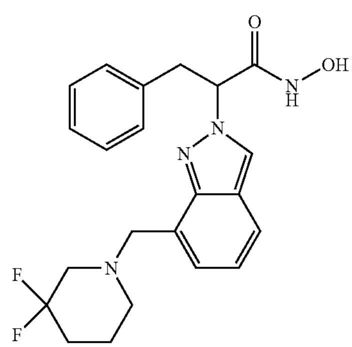 [SMILES: O=C(NO)C(Cc1ccccc1)n1cc2cccc(CN3CCCC(F)(F)C3)c2n1] | 415.2 |
| I-0191 | N-hydroxy-3-phenyl-2-(7-((4-(trifluoromethyl)piperidin-1-yl)methyl)-2H-indazol-2-yl)propanamide | 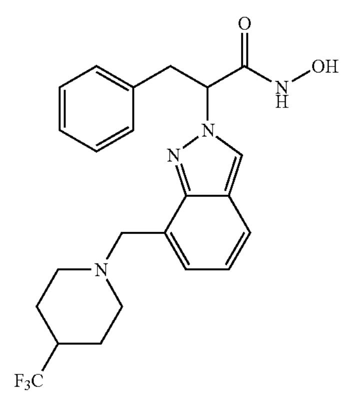 [SMILES: O=C(NO)C(Cc1ccccc1)n1cc2cccc(CN3CCC(C(F)(F)F)CC3)c2n1] | 447.2 |

TABLE 4-continued

The compounds listed in Table 4 were prepared in accordance with the synthetic protocols set forth in Scheme 12 and Example 5, using the appropriate starting materials.

| No. | Name | Structure | LCMS (M + H)+ |
|---|---|---|---|
| I-0192 | N-hydroxy-2-(7-((4-methyl-3-oxopiperazin-1-yl)methyl)-2H-indazol-2-yl)-3-phenylpropanamide | 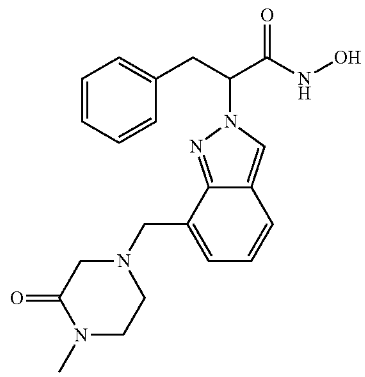 [SMILES: CN1CCN(Cc2cccc3cn(C(Cc4ccccc4)C(=O)NO)nc23)CC1=O] | 408.2 |

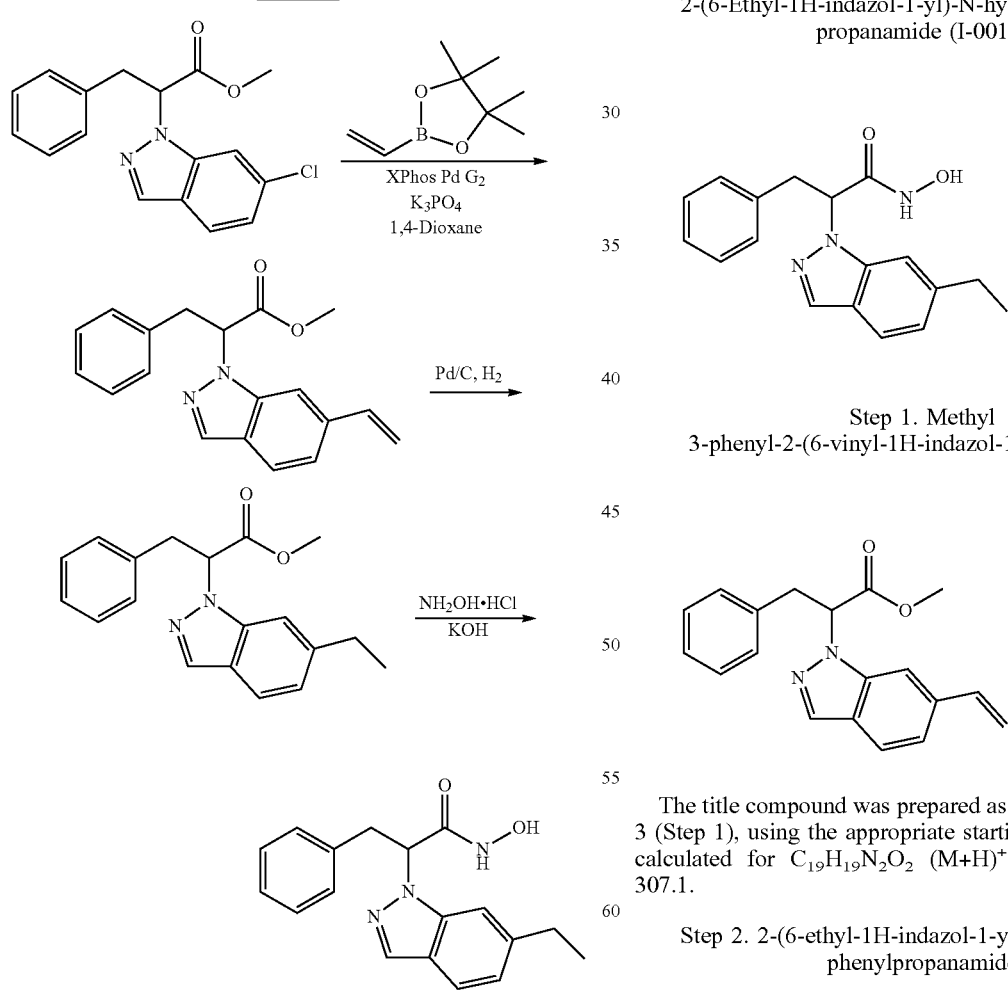

Example 6

2-(6-Ethyl-1H-indazol-1-yl)-N-hydroxy-3-phenyl-propanamide (I-0018)

Step 1. Methyl 3-phenyl-2-(6-vinyl-1H-indazol-1-yl)propanoate

The title compound was prepared as depicted in Example 3 (Step 1), using the appropriate starting materials. LCMS calculated for $C_{19}H_{19}N_2O_2$ (M+H)+: m/z=307.1; found 307.1.

Step 2. 2-(6-ethyl-1H-indazol-1-yl)-N-hydroxy-3-phenylpropanamide

A solution of methyl 3-phenyl-2-(6-vinyl-1H-indazol-1-yl)propanoate (35.0 mg, 0.114 mmol) in ethyl acetate (3.0 mL) under $N_2$ atmosphere was treated with 10 wt % Pd on carbon (30 mg, 0.028 mmol). The mixture was purged with H₂ and stirred under H₂ atmosphere (1 atm) for 25 h. The reaction was then filtered through a pad of Celite (eluted with MeOH). The filtrate was concentrated. The residue was dissolved in 1:1 THF/MeOH (1.0 mL) and then KCN (3 mg, 0.04 mmol) and hydroxylamine (76 µL, 50% aq. solution) were added. The reaction mixture was stirred at room temperature for 17 h and then concentrated. The resulting residue was purified using RP-HPLC (Waters SunFire™ C18 column, 30 mm×100 mm, 5 µm particle size, eluting with a gradient of acetonitrile/water containing 0.1% TFA, at flow rate of 60 mL/min) to afford compound (I-0018) as an off-white solid (21.0 mg). LCMS calculated for $C_{18}H_{20}N_3O_2$ (M+H)⁺: m/z=310.2; found 310.2. IC50: 443 nM.

TABLE 5

The compounds listed in Table 5 were prepared in accordance with the synthetic protocols set forth in Scheme 13 and Example 6, using the appropriate starting materials.

| No. | Chemical Name | Structure | LCMS (M + H)⁺ |
|---|---|---|---|
| I-0020 | 2-(5-ethyl-1H-indazol-1-yl)-N-hydroxy-3-phenylpropanamide | 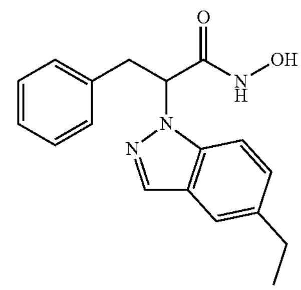 [SMILES: CCc1ccc2c(cnn2C(Cc2ccccc2)C(=O)NO)c1] | 310.2 |
| I-0153 | N-hydroxy-3-phenyl-2-(5-(4-(pyrrolidin-1-yl)cyclohexyl)-1H-indazol-1-yl)propanamide | 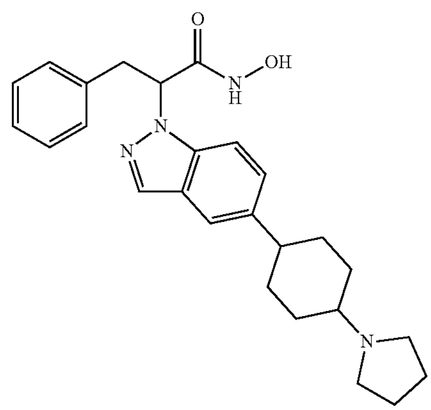 [SMILES: O=C(NO)C(Cc1ccccc1)n1ncc2cc(C3CCC(N4CCCC4)CC3)ccc21] | 433.3 |
| I-0048 | N-hydroxy-2-(6-(1-methylpiperidin-4-yl)-2H-indazol-2-yl)-3-phenylpropanamide | 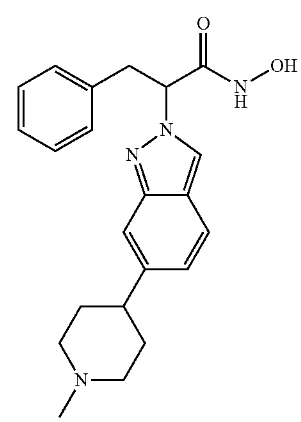 [SMILES: CN1CCC(c2ccc3cn(C(Cc4ccccc4)C(=O)NO)nc3c2)CC1] | 379.2 |

TABLE 5-continued

The compounds listed in Table 5 were prepared in accordance with the synthetic protocols set forth in Scheme 13 and Example 6, using the appropriate starting materials.

| No. | Chemical Name | Structure | LCMS (M + H)+ |
|---|---|---|---|
| I-0065 | N-hydroxy-2-(4-(1-methylpiperidin-4-yl)-2H-indazol-2-yl)-3-phenylpropanamide | 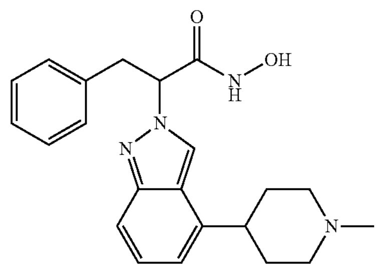 [SMILES: CN1CCC(c2cccc3nn(C(Cc4ccccc4)C(=O)NO)cc23)CC1] | 379.2 |

Scheme 14

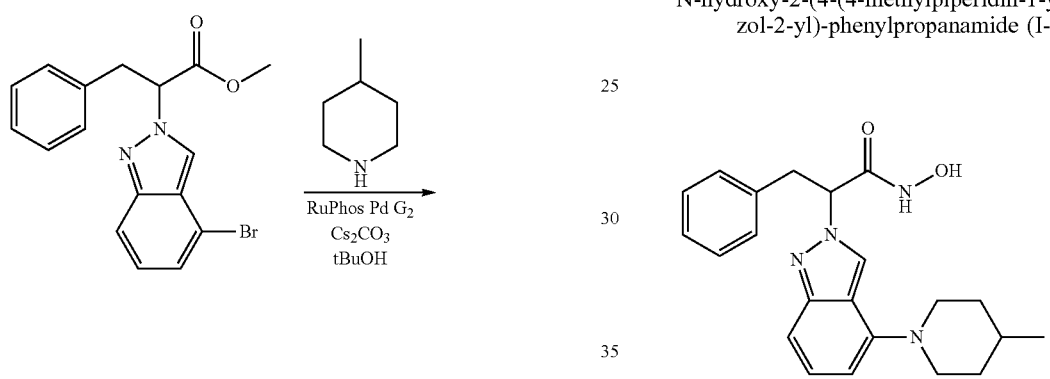

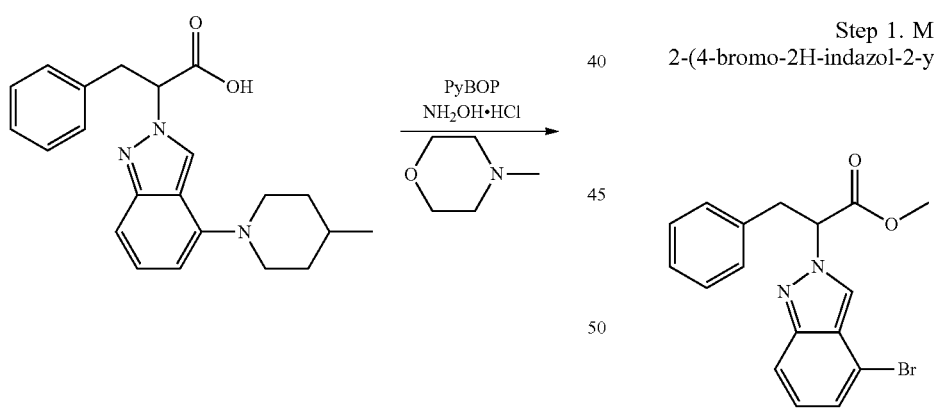

Example 7

N-hydroxy-2-(4-(4-methylpiperidin-1-yl)-2H-indazol-2-yl)-phenylpropanamide (I-0145)

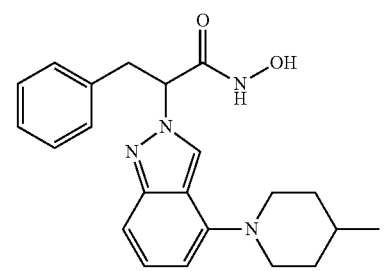

Step 1. Methyl 2-(4-bromo-2H-indazol-2-yl)-3-phenylpropanoate

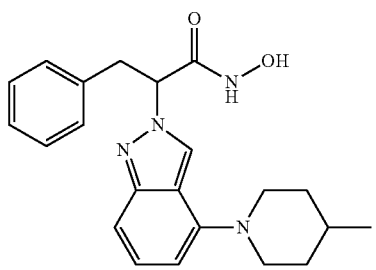

The title compound was prepared as depicted in Example 1 (Step 1), using the appropriate starting materials. LCMS calculated for $C_{17}H_{16}BrN_2O_2$ (M+H)+: m/z=359.0; found 359.0.

Step 2. N-hydroxy-2-(4-(4-methylpiperidin-1-yl)-2H-indazol-2-yl)-3-phenylpropanamide To a screw-cap vial equipped with a magnetic stir bar was added methyl 2-(4-bromo-2H-indazol-2-yl)-3-phenylpropanoate (40.0 mg, 0.111 mmol), dicyclohexyl(2',6'-diisopropoxybiphenyl-2-yl)phosphine-(2'-aminobiphenyl-2-yl)(chloro)palladium (1:1) (RuPhos Pd G2, Aldrich, 21.8 mg.

0.0281 mmol), and Cs$_2$CO$_3$ (149.1 mg, 0.4576 mmol). The vial was sealed with a Teflon-lined septum, evacuated and backfilled with nitrogen (this process was repeated a total of three times). A solution of 4-methylpiperidine (29.0 μL, 0.245 mmol) in anhydrous tert-BuOH (1.00 mL) was added. The mixture was heated to 90° C. for 3 h. After cooling to room temperature, 1 M aqueous HCl solution (5.0 mL) was added. The mixture was washed with EtOAc (2×5.0 mL). The aqueous layer was evaporated to dryness. The residue was then dissolved in DMF (0.5 mL), and treated with a solution of (benzotriazol-1-yloxy)tripyrrolidinophosphonium hexafluorophosphate (81.1 mg, 0.156 mmol) in DMF (0.5 nit). The reaction mixture was stirred at room temperature for 10 min, and then treated with hydroxylamine hydrochloride (9.3 mg, 0.13 mmol), followed by 4-methylmorpholine (50.0 μL, 0.455 mmol). The reaction mixture was stirred at room temperature overnight, and then filtered. The filtrate was purified using RP-HPLC (Waters XBridge™ C18 column, 30 mm×100 mm, 5 μm particle size, eluting with a gradient of MeCN/water containing 0.15% NH$_4$OH, at flow rate of 60 mL/min) to afford compound (I-0145) as a white solid (5.0 mg, 12%). LCMS calculated for C$_{22}$H$_{27}$N$_4$O$_2$ (M+H)$^+$: m/z=379.2; found 379.2. IC50: 717 nM.

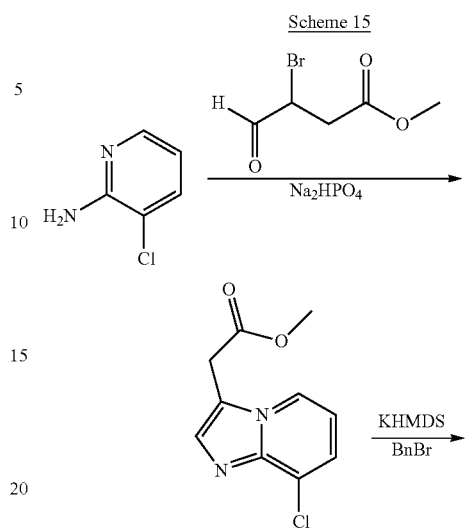

Scheme 15

TABLE 6

The compounds listed in Table 6 were prepared in accordance with the synthetic protocols set forth in Scheme 14 and Example 7, using the appropriate starting materials.

| No. | Chemical Name | Structure | LCMS (M + H)$^+$ |
|---|---|---|---|
| I-0052 | N-hydroxy-3-phenyl-2-(6-(piperidin-1-yl)-2H-indazol-2-yl)propanamide | 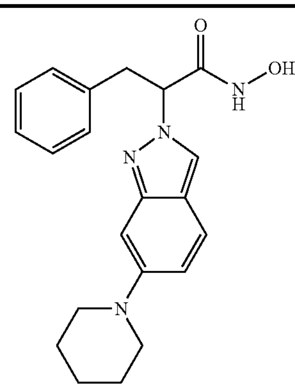 | 365.2 |
| I-0059 | N-hydroxy-2-(4-morpholino-2H-indazol-2-yl)-3-phenylpropanamide | 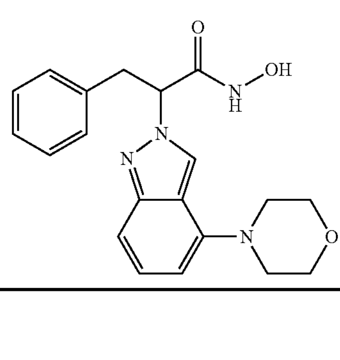 | 367.2 |

-continued

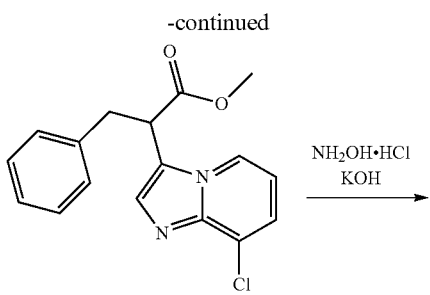

To a mixture of 3-chloropyridin-2-amine (1.93 g, 15.0 mmol), methyl 3-bromo-4-oxobutanoate (2.35 g, 12.0 mmol), and disodium hydrogen phosphate (4.28 g, 30.1 mmol) was added isopropyl alcohol (80.0 mL). The mixture was heated to reflux for 15 h. After cooling to room temperature, the reaction was filtered. The filtrate was concentrated. The residue was purified on silica gel (120 g, 0-50% EtOAc in $CH_2Cl_2$) to give the desired product as a brown oil (706.8 mg, 26%). LCMS calculated for $C_{10}H_{10}ClN_2O_2$ (M+H)$^+$: m/z=225.0; found 225.0.

Step 2. Methyl 2-(8-chloroimidazo[1,2-a]pyridin-3-yl)-3-phenylpropanoate

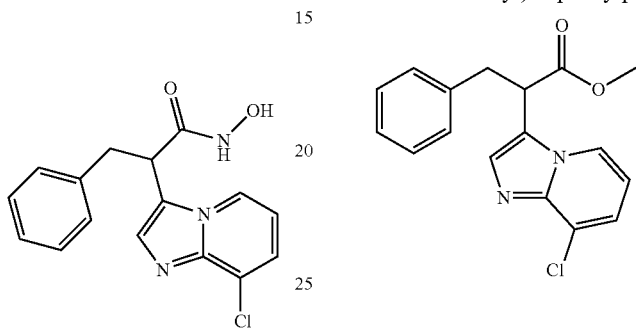

To a solution of methyl (8-chloroimidazo[1,2-a]pyridin-3-yl)acetate (706.8 mg, 3.146 mmol) in THF (5.00 mL) at −78° C. was added 1.0 M KHMDS in THF (3.40 mL, 3.40 mmol) dropwise. The solution was allowed to warm to 0° C. and stirred for 1 h. Then the mixture was cooled back to −78° C. A solution of benzyl bromide (540.0 mg, 3.157 mmol) in THF (4.00 mL) was added dropwise. The reaction was allowed to warm to room temperature. After stirring at room temperature for 16 h, the reaction was diluted with EtOAc and washed with water and brine. The organic layer was dried over anhydrous $Na_2SO_4$, filtered and concentrated. The resulting residue was purified on silica gel (40 g, 0-100% EtOAc in hexanes) to give the desired product a pale yellow oil (877.3 mg, 89%). LCMS calculated for $C_{17}H_{16}ClN_2O_2$ (M+H)$^+$: m/z=315.1; found 315.1.

Step 3. 2-(8-Chloroimidazo[1,2-a]pyridin-3-yl)-N-hydroxy-3-phenylpropanamide

To a suspension of hydroxylamine hydrochloride (92.2 mg, 1.33 mmol) in MeOH (0.20 mL) was added a solution of KOH (99.4 mg, 1.772 mmol) in MeOH (0.50 mL). The resulting white suspension was stirred at room temperature for 30 min, and then cooled to 0° C. A solution of methyl 2-(8-chloroimidazo[1,2-a]pyridin-3-yl)-3-phenylpropanoate (28.8 mg, 0.0915 mmol) in MeOH (1.0 mL) was added. After stirring at 0° C. for 30 min, the reaction was neutralized with 0.30 mL 4.0 M HCl (aq). The mixture was diluted with MeOH and filtered. The filtrate was purified using RP-HPLC (Waters SunFire™ C18 column, 30 mm×100 mm, 5 μm particle size, eluting with a gradient of acetonitrile/water containing 0.1% TFA, at flow rate of 60 mL/min) to afford compound (I-0134) as a white solid (17.9 mg). LCMS calculated for $C_{16}H_{15}ClN_3O_2$ (M+H)$^+$: m/z=316.1; found 316.1. IC50: 258 nM.

Example 8

2-(8-Chloroimidazo[1,2-a]pyridin-3-yl)-N-hydroxy-3-phenylpropanamide (I-0134)

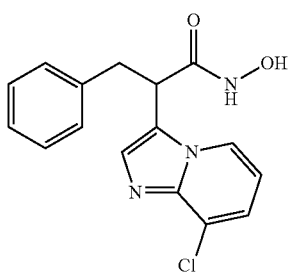 [SMILES: O=C(NO)C(Cc1ccccc1)c1cnc2c(Cl)cccn12]

Step 1. Methyl (8-chloroimidazo[1,2-a]pyridin-3-yl)acetate

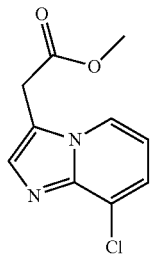

Example 9

2-(7-Chloroimidazo[1,2-a]pyridin-3-yl)-N-hydroxy-3-phenylpropanamide (I-0093)

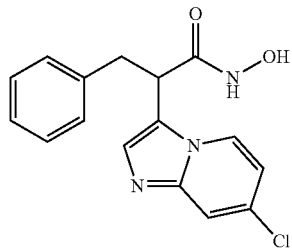 [SMILES: O=C(NO)C(Cc1ccccc1)c1cnc2cc(Cl)ccn12]

Compound (I-0093) was prepared using the synthetic protocols as set forth in Scheme 14 and Example 7, using the appropriate starting materials. LCMS calculated for $C_{16}H_{15}ClN_3O_2$ (M+H)$^+$: m/z=316.1; found 316.1. $^1$H NMR (500 MHz, DMSO) δ 10.82 (s, 1H), 8.74 (d, J=7.4 Hz, 1H), 8.11-7.95 (m, 2H), 7.48 (dd, J=7.4, 1.9 Hz, 1H), 7.21 (dd, J=32.0, 4.3 Hz, 5H), 4.30-4.20 (m, 1H), 3.41 (dd, J=13.7, 8.7 Hz, 1H), 3.18 (dd, J=13.7, 6.9 Hz, 1H), IC50: 22 nM.

Scheme 16

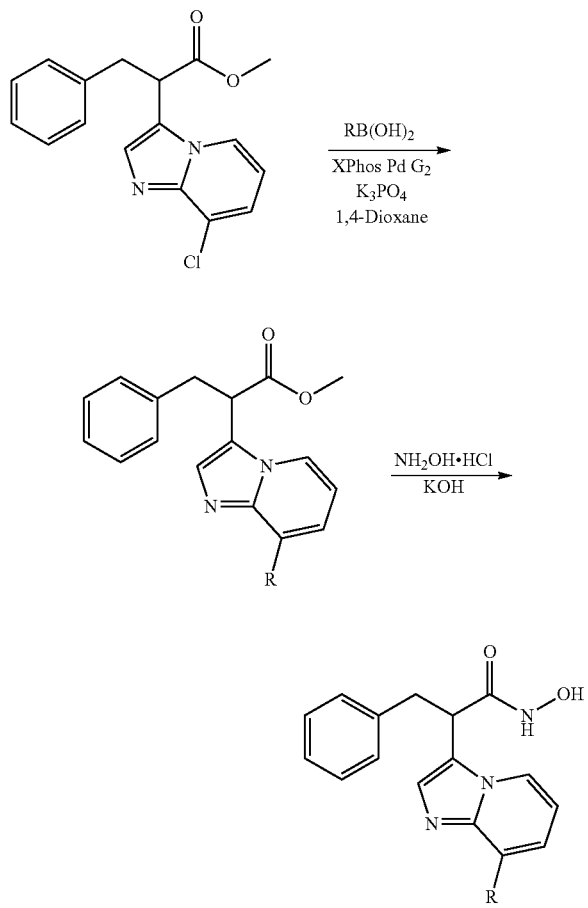

Example 10

N-hydroxy-3-phenyl-2-(8-pyrimidin-5-ylimidazo[1,2-a]pyridin-3-yl)propanamide (I-0164)

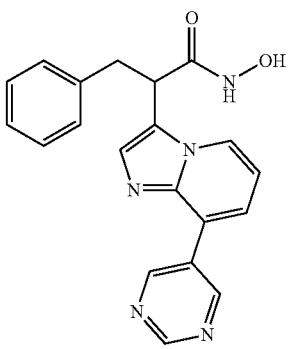 [SMILES: O=C(NO)C(Cc1ccccc1)c1cnc2c(-c3cncnc3)cccn12]

To a screw-cap vial equipped with a magnetic stir bar was added 5-(4,4,5,5-tetramethyl-1,3,2-dioxaborolan-2-yl)pyrimidine (46.1 mg, 0.224 mmol), dicyclohexyl(2',4',6'-triisopropylbiphenyl-2-yl)phosphine-(2'-aminobiphenyl-2-yl)(chloro)palladium (1:1) (XPhos Pd G2, Aldrich, 10.4 mg, 0.0132 mmol), and potassium phosphate (86.4 mg, 0.407 mmol). The vial was sealed with a Teflon-lined septum, evacuated and backfilled with nitrogen (this process was repeated a total of three times). A solution of methyl 2-(8-chloroimidazo[1,2-a]pyridin-3-yl)-3-phenylpropanoate (30.6 mg, 0.0972 mmol) in 1,4-dioxane (1.00 mL) was added followed by degassed water (0.10 mL). The reaction was stirred at 80° C. for 1 h. After cooling to room temperature, the reaction was diluted with $CH_2Cl_2$, filtered and concentrated. The resulting residue was dissolved in 1:1 THF/MeOH (1.0 mL).

To another vial containing hydroxylamine hydrochloride (99.8 mg, 1.44 mmol) was added MeOH (0.30 mL) followed by a solution of KOH (119.3 mg, 2.126 mmol) in MeOH (0.60 mL). The resulting white suspension was stirred at room temperature for 30 min, and then cooled to 0° C. The above THF/MeOH solution was added. The reaction mixture was stirred at 0° C. for 30 min, and then neutralized with 0.60 mL 4.0 M (aq). The mixture was diluted with MeOH and filtered. The filtrate was purified using RP-HPLC (Waters SunFire™ C18 column, 30 mm×100 mm, 5 μm particle size, eluting with a gradient of acetonitrile/water containing 0.1% TFA, at flow rate of 60 mL/min) to afford compound (I-0164) as a white solid (23.9 mg). LCMS calculated for $C_{20}H_{18}N_5O_2$ (M+H)$^+$: m/z=360.1; found 360.1.

TABLE 7

The compounds listed in Table 7 were prepared in accordance with the synthetic protocols set forth in Scheme 16 and Example 10, using the appropriate starting materials.

| No. | Name | Structure ¹H-NMR | LCMS (M + H)⁺ |
|---|---|---|---|
| I-0162 | N-hydroxy-3-phenyl-2-(8-(pyridin-4-yl)imidazo[1,2-a]pyridin-3-yl)propanamide | | 359.2 |
| I-0163 | N-hydroxy-3-phenyl-2-(8-(pyridin-3-yl)imidazo[1,2-a]pyridin-3-yl)propanamide | | 359.2 |
| I-0167 | 4-(3-(1-(hydroxyamino)-1-oxo-3-phenylpropan-2-yl)imidazo[1,2-a]pyridin-8-yl)benzamide | | 401.2 |

TABLE 7-continued

The compounds listed in Table 7 were prepared in accordance with the synthetic protocols set forth in Scheme 16 and Example 10, using the appropriate starting materials.

| No. | Name | Structure $^1$H-NMR | LCMS (M + H)$^+$ |
|---|---|---|---|
| I-0168 | 4-(3-(1-(hydroxyamino)-1-oxo-3-phenylpropan-2-yl)imidazo[1,2-a]pyridin-8-yl)-N,N-dimethylbenzamide | | 429.2 |
| I-0169 | 3-(3-(1-(hydroxyamino)-1-oxo-3-phenylpropan-2-yl)imidazo[1,2-a]pyridin-8-yl)benzamide | | 401.2 |
| I-0170 | 2-(8-cyclopropylimidazo[1,2-a]pyridin-3-yl)-N-hydroxy-3-phenylpropanamide | | 322.2 |
| I-0171 | N-hydroxy-2-(8-methylimidazo[1,2-a]pyridin-3-yl)-3-phenylpropanamide | | 296.1 |

TABLE 7-continued

The compounds listed in Table 7 were prepared in accordance with the synthetic protocols set forth in Scheme 16 and Example 10, using the appropriate starting materials.

| No. | Name | Structure ¹H-NMR | LCMS (M + H)⁺ |
|---|---|---|---|
| I-0112 | N-hydroxy-3-phenyl-2-(7-(pyrimidin-5-yl)imidazo[1,2-a]pyridin-3-yl)propanamide | ¹H NMR (400 MHz, DMSO) δ 10.85 (s, 1H), 9.39-9.32 (m, 2H), 9.30 (s, 1H), 8.90 (d, J = 7.3 Hz, 1H), 8.33 (d, J = 10.0 Hz, 1H), 8.16 (s, 1H), 7.92 (dd, J = 14.1, 6.5 Hz, 1H), 7.35-7.10 (m, 5H), 4.38-4.25 (m, 1H), 3.46 (dd, J = 13.6, 8.8 Hz, 1H), 3.24 (dd, J = 13.6, 6.8 Hz, 1H). | 360.1 |
| I-0113 | N-hydroxy-3-phenyl-2-(7-(pyridin-4-yl)imidazo[1,2-a]pyridin-3-yl)propanamide | ¹H NMR (400 MHz, DMSO) δ 10.85 (s, 1H), 8.87 (d, J = 7.2 Hz, 1H), 8.82 (d, J = 6.3 Hz, 2H), 8.34 (d, J = 10.2 Hz, 1H), 8.17 (s, 1H), 8.05 (d, J = 6.1 Hz, 2H), 7.92 (d, J = 7.2 Hz, 1H), 7.34-7.11 (m, 5H), 4.33 (t, J = 7.8 Hz, 1H), 3.46 (dd, J = 13.7, 8.6 Hz, 1H), 3.24 (dd, J = 13.8, 6.9 Hz, 1H). | 359.2 |

TABLE 7-continued

The compounds listed in Table 7 were prepared in accordance with the synthetic protocols set forth in Scheme 16 and Example 10, using the appropriate starting materials.

| No. | Name | Structure ¹H-NMR | LCMS (M + H)⁺ |
|---|---|---|---|
| I-0114 | N-hydroxy-3-phenyl-2-(7-(pyridin-3-yl)imidazo[1,2-a]pyridin-3-yl)propanamide | ¹H NMR (400 MHz, DMSO) δ 10.86 (s, 1H), 9.14 (d, J = 2.0 Hz, 1H), 8.89 (d, J = 7.2 Hz, 1H), 8.72 (dd, J = 4.8, 1.4 Hz, 1H), 8.36 (d, J = 8.2 Hz, 1H), 8.25 (s, 1H), 8.19 (s, 1H), 7.94 (d, J = 5.7 Hz, 1H), 7.62 (dd, J = 7.8, 4.9 Hz, 1H), 7.38-6.99 (m, 5H), 4.38-4.27 (m, 1H), 3.46 (dd, J = 13.7, 8.6 Hz, 1H), 3.24 (dd, J = 13.6, 6.9 Hz, 1H). | 359.2 |
| I-0115 | N-hydroxy-2-(7-(1-methyl-1H-pyrazol-5-yl)imidazo[1,2-a]pyridin-3-yl)-3-phenylpropanamide | ¹H NMR (400 MHz, DMSO) δ 10.86 (s, 1H), 8.83 (d, J = 7.2 Hz, 1H), 8.17 (s, 1H), 8.04 (s, 1H), 7.67 (dd, J = 7.2, 1.5 Hz, 1H), 7.58 (d, J = 1.9 Hz, 1H), 7.33-7.15 (m, 5H), 6.76 (d, J = 1.9 Hz, 1H), 4.33 (t, J = 7.7 Hz, 1H), 4.00 (s, 3H), 3.45 (dd, J = 13.6, 8.7 Hz, 1H), 3.23 (dd, J = 13.6, 6.9 Hz, 1H). | 362.2 |
| I-0150 | N-hydroxy-2-(7-(4-(methoxymethyl)phenyl)imidazo[1,2-a]pyridin-3-yl)-3-phenylpropanamide | | 402.2 |

TABLE 7-continued

The compounds listed in Table 7 were prepared in accordance with the synthetic protocols set forth in Scheme 16 and Example 10, using the appropriate starting materials.

| No. | Name | Structure $^1$H-NMR | LCMS (M + H)$^+$ |
|---|---|---|---|
| I-0151 | N-hydroxy-2-(7-(4-(4-methylpiperazin-1-yl)phenyl)imidazo[1,2-a]pyridin-3-yl)-3-phenylpropanamide | | 456.2 |
| I-0152 | N-hydroxy-2-(7-(6-(4-methylpiperazin-1-yl)pyridin-3-yl)imidazo[1,2-a]pyridin-3-yl)-3-phenylpropanamide | | 457.2 |

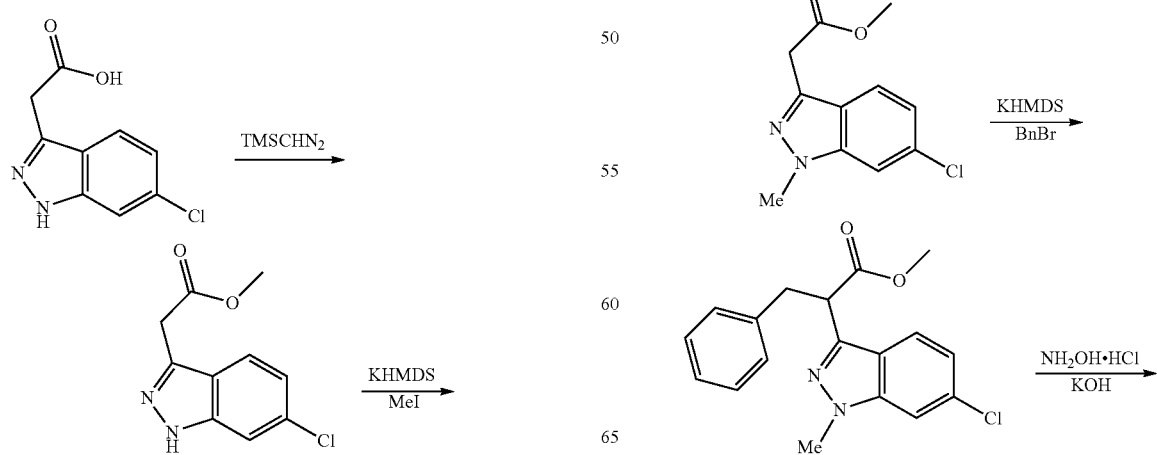

Scheme 17

-continued

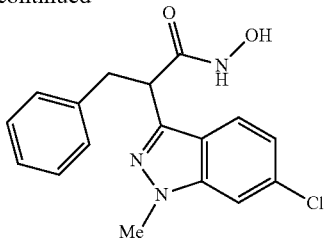

Example 11

2-(6-Chloro-1-methyl-1H-indazol-3-yl)-N-hydroxy-3-phenylpropanamide (I-0202)

Step 1. Methyl (6-chloro-1H-indazol-3-yl)acetate

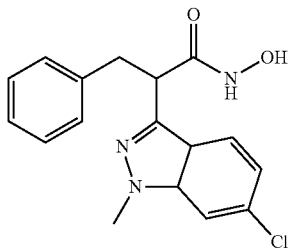 [SMILES: CN1N=C(C(Cc2ccccc2)C(=O)NO)C2C=CC(Cl)=CC21]

To a solution of (6-chloro-1H-indazol-3-yl)acetic acid (865.5 mg, 4.109 mmol) in MeOH (8.00 mL) at 0° C. was added 2.0 M trimethylsilyldiazomethane in ethyl ether (5.00 mL, 10.0 mmol) dropwise. The mixture was allowed to warm to room temperature. After stirring at room temperature for 2 h, the reaction was concentrated. The residue was purified on silica gel (120 g, 0-100% EtOAc in hexanes) to give the desired product as a pale yellow solid (475.6 mg, 51%). LCMS calculated for $C_{10}H_{10}ClN_2O_2$ (M+H)$^+$: m/z=225.0; found 225.0.

Step 2. Methyl (6-chloro-1-methyl-1H-indazol-3-yl)acetate

To a solution of methyl (6-chloro-1H-indazol-3-yl)acetate (475.6 mg, 2.117 mmol) in THF (3.00 mL) at −78° C. was added 1.0 M KHMDS in THF (2.50 mL, 2.50 mmol) dropwise. The reaction mixture was allowed to warm to room temperature and stirred for 30 min. Then the reaction was cooled back to −78° C. A solution of MeI (932.7 mg, 6.571 mmol) in THF (3.00 mL, 37.0 mmol) was added dropwise. The reaction mixture was allowed to warm to room temperature. After stirring at room temperature for 1 h, the mixture was then diluted with $CH_2Cl_2$, filtered and concentrated. The residue was purified on silica gel (40 g, 0-100% EtOAc in hexanes) to give the desired product as a pale yellow solid (286.5 mg, 57%). LCMS calculated for $C_{11}H_{12}ClN_2O_2$ (M+H)$^+$: m/z=239.1; found 239.0.

Step 3. Methyl 2-(6-chloro-1-methyl-1H-indazol-3-yl)-3-phenylpropanoate

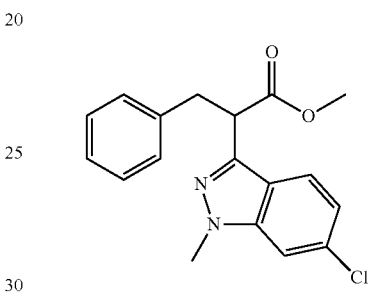

To a stirred solution of methyl (6-chloro-1-methyl-1H-indazol-3-yl)acetate (286.5 mg, 1.200 mmol) in THF (3.00 mL, 37.0 mmol) at −78° C. was added 1.0 M KHMDS in THF (1.40 mL, 1.40 mmol) dropwise. The solution was allowed to warm to 0° C. and stirred for 30 min. Then the mixture was cooled back to −78° C. A solution of benzyl bromide (211.2 mg, 1.235 mmol) in THF (2.00 mL) was added dropwise. The reaction was allowed to warm to room temperature. After stirring at room temperature for 3 h, the reaction was diluted with EtOAc, washed with brine. The organic layer was dried over anhydrous $Na_2SO_4$, filtered and concentrated. The resulting residue was purified on silica gel (40 g, 0-100% EtOAc in hexanes) to give the desired product a colorless oil (317.6 mg, 80%). LCMS calculated for $C_{18}H_{18}ClN_2O_2$ (M+H)$^+$: m/z=329.1; found 329.1.

Step 4. 2-(6-Chloro-1-methyl-1H-indazol-3-yl)-N-hydroxy-3-phenylpropanamide

To a suspension of hydroxylamine hydrochloride (94.4 mg, 1.36 mmol) in MeOH (0.20 mL) was added a solution of KOH (158.1 mg, 2.818 mmol) in MeOH (0.80 mL). The resulting white suspension was stirred at room temperature for 30 min, and then cooled to 0° C. A solution of methyl 2-(6-chloro-1-methyl-1H-indazol-3-yl)-3-phenylpropanoate (31.7 mg, 0.0964 mmol) in MeOH (1.0 mL) was added. The reaction mixture was stirred at 0° C. for 30 min, and then neutralized with 0.60 mL 4.0 M HCl (aq). The mixture was diluted with MeOH and filtered. The filtrate was purified using RP-HPLC (Waters SunFire™ C18 column, 30 mm×100 mm, 5 μm particle size, eluting with a gradient of acetonitrile/water containing 0.1% TEA, at flow rate of 60 mL/min) to afford compound (I-0202) as a white solid (21.0 mg). LCMS calculated for $C_{17}H_{17}ClN_3O_2$ (M+H)$^+$: m/z=330.1; found 330.1. $^1$H NMR (500 MHz, DMSO) δ 10.74 (s, 1H), 7.99 (d, J=8.6 Hz, 1H), 7.75 (d, J=1.6 Hz, 1H),

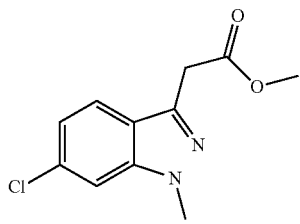 [SMILES: CNc1cc(Cl)ccc1C(=N)CC(=O)OC]

7.26-7.11 (m, 6H), 4.07 (dd, J=9.2, 6.3 Hz, 1H), 3.95 (s, 3H), 3.45 (dd, J=13.7, 9.3 Hz, 1H), 3.17 (dd, J=13.7, 6.3 Hz, 1H). IC50: 39 nM.

Scheme 18

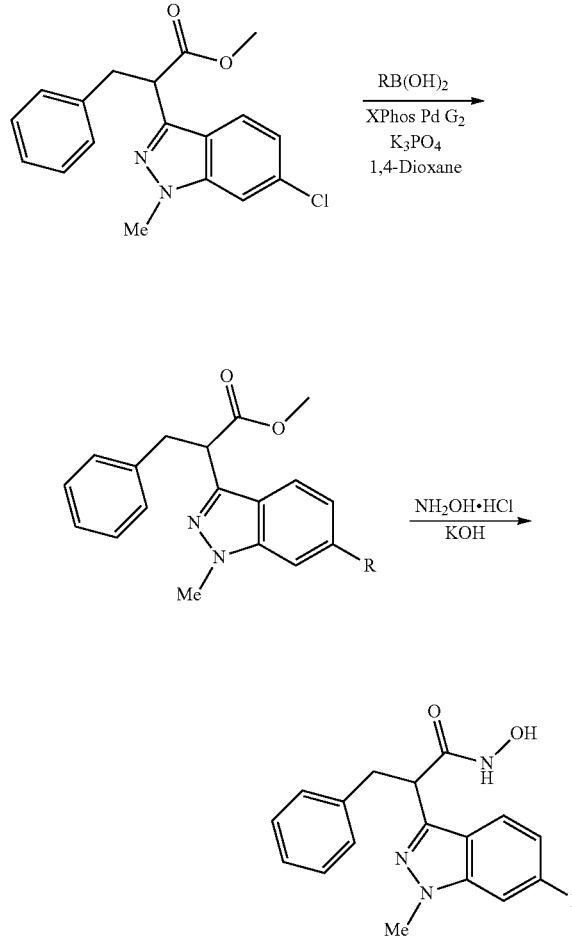

Example 12

N-hydroxy-2-(1-methyl-6-pyrimidin-5-yl-1H-indazol-3-yl)-3-phenylpropanamide (I-0204)

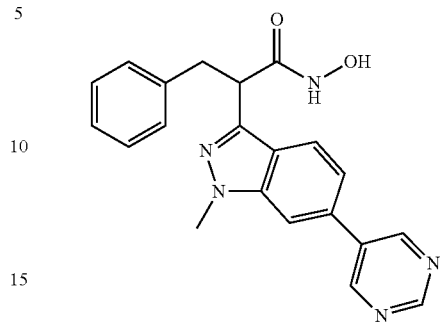

To a screw-cap vial equipped with a magnetic stir bar was added 5-(4,4,5,5-tetramethyl-1,3,2-dioxaborolan-2-yl)pyrimidine (51.0 mg, 0.248 mmol), dicyclohexyl(2',4',6'-triisopropylbiphenyl-2-yl)phosphine-(2-yl)-aminobiphenyl-2-yl)(chloro)palladium (1:1) (XPhos Pd G2, Aldrich, 9.3 mg, 0.0118 mmol), and potassium phosphate (103.9 mg, 0.4895 mmol). The vial was sealed with a Teflon-lined septum, evacuated and backfilled with nitrogen (this process was repeated a total of three times). A solution of methyl 2-(8-chloroimidazo[1,2-a]pyridin-3-yl)-3-phenylpropanoate (39.3 mg, 0.120 mmol) in 1,4-dioxane (1.00 mL) was added followed by degassed water (0.10 mL). The reaction was stirred at 80° C. for 1 h. After cooling to room temperature, the reaction was diluted with $CH_2Cl_2$, filtered and concentrated. The resulting residue was dissolved in 1:1 THF/MeOH (1.0 mL).

To another vial containing hydroxylamine hydrochloride (133.2 mg, 1.917 mmol) was added MeOH (0.30 mL) followed by a solution of KOH (197.5 mg, 3.52 mmol) in MeOH (1.00 mL). The resulting white suspension was stirred at room temperature for 30 min, and then cooled to 0° C. The above THF/MeOH solution was added. The reaction mixture was stirred at 0° C. for 30 min, and then neutralized with 0.80 mL 4.0 M HCl (aq). The mixture was diluted with MeOH and filtered. The filtrate was purified using RP-HPLC (Waters SunFire™ C18 column, 30 mm×100 mm, 5 μm particle size, eluting with a gradient of acetonitrile/water containing 0.1% TFA, at flow rate of 60 mL/min) to afford compound (I-0204) as a white solid (9.5 mg). LCMS calculated for $C_{21}H_{20}N_5O_2$ $(M+H)^+$: m/z=374.2; found 374.1. IC50: 84 nM.

TABLE 8

The compounds listed in Table 8 were prepared in accordance with the synthetic protocols set forth in Scheme 18 and Example 12, using the appropriate starting materials.

| No. | Chemical Name | Structure | LCMS (M + H)+ |
|---|---|---|---|
| I-0203 | N-hydroxy-2-(1-methyl-6-(1-methyl-1H-pyrazol-5-yl)-1H-indazol-3-yl)-3-phenylpropanamide | 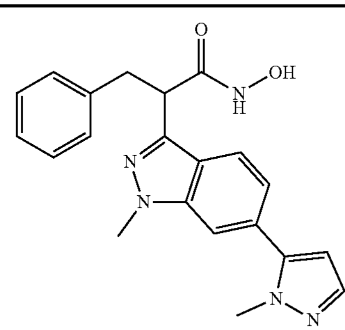 | 376.2 |

151
TABLE 8-continued
The compounds listed in Table 8 were prepared in accordance with the synthetic protocols set forth in Scheme 18 and Example 12, using the appropriate starting materials.
| No. | Chemical Name | Structure | LCMS (M + H)+ |
|---|---|---|---|
| I-0205 | N-hydroxy-2-(1-methyl-6-(pyridin-4-yl)-1H-indazol-3-yl)-3-phenylpropanamide | 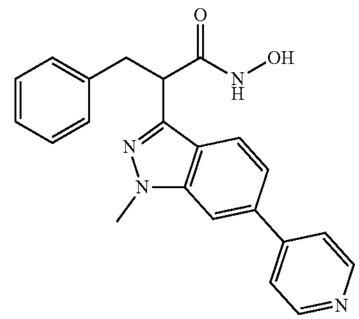 [SMILES: Cn1nc(C(Cc2ccccc2)C(=O)NO)c2ccc(-c3ccncc3)cc21] | 373.2 |
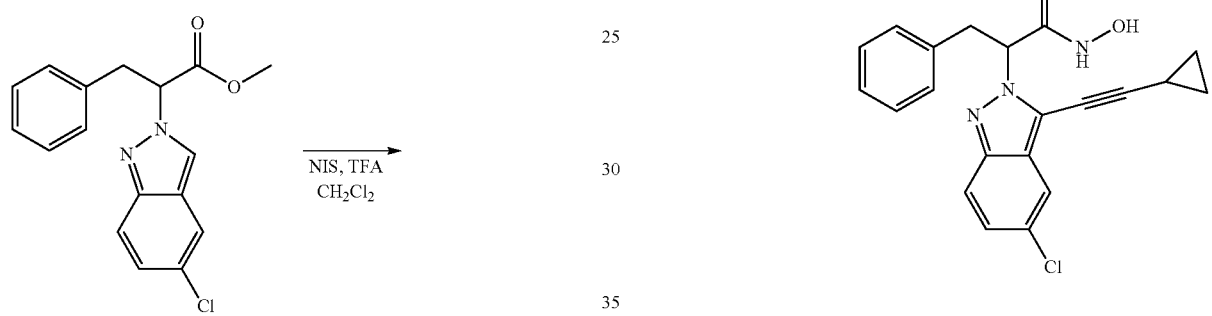
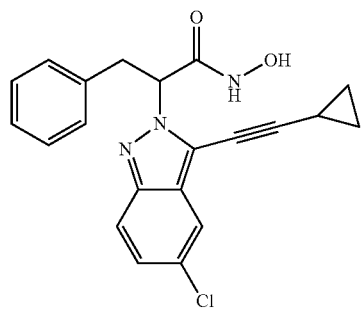
Example 13
2-[5-Chloro-3-(cyclopropylethynyl)-2H-indazol-2-yl]-N-hydroxy-3-phenylpropanamide (I-0005)
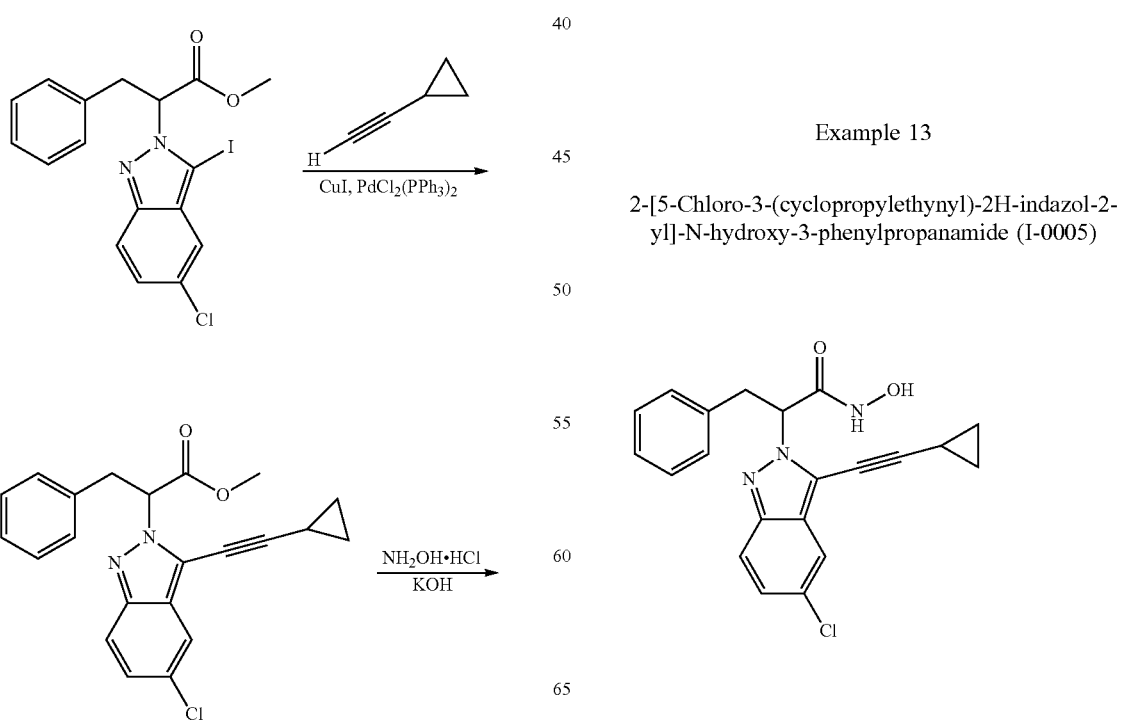

Step 1. Methyl 2-(5-chloro-2H-indazol-2-yl)-3-phenylpropanoate

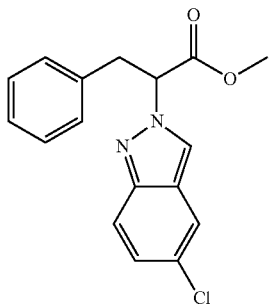 [SMILES: COC(=O)C(Cc1ccccc1)n1cc2cc(Cl)ccc2n1]

The title compound was prepared as depicted in Example 1 (Step 1). LCMS calculated for $C_{17}H_{16}ClN_2O_2$ (M+H)$^+$: m/z=315.1; found 315.1.

Step 2. Methyl 2-(5-chloro-3-iodo-2H-indazol-2-yl)-3-phenylpropanoate

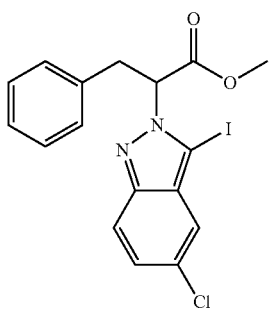 [SMILES: COC(=O)C(Cc1ccccc1)n1nc2ccc(Cl)cc2c1I]

To a solution of methyl 2-(5-chloro-2H-indazol-2-yl)-3-phenylpropanoate (189.1 mg, 0.6008 mmol) in $CH_2Cl_2$ (3.00 mL) at room temperature was added N-Iodosuccinimide (183.1 mg, 0.8138 mmol) followed by trifluoroacetic acid (50.0 μL, 0.649 mmol). After stirring at room temperature for 4 h, the reaction mixture was diluted with EtOAc, washed with 1 M NaHSO$_3$ (aq), 1 M Na$_2$CO$_3$ (aq) and brine. The organic layer was dried over anhydrous Na$_2$SO$_4$, filtered and concentrated. The residue was purified on silica gel (40 g, 0-50% EtOAc in hexanes) to give the desired product as a pale yellow solid (1909 mg, 72%). LCMS calculated for $C_{17}H_{15}ClIN_2O_2$ (M+H)$^+$: m/z=441.0; found 440.9.

Step 3. Methyl 2-[5-chloro-3-(cyclopropylethynyl)-2H-indazol-2-yl]-3-phenylpropanoate

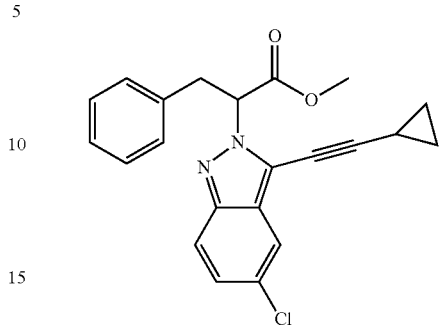

To a screw-cap vial equipped with a magnetic stir bar was added methyl 2-(5-chloro-3-iodo-2H-indazol-2-yl)-3-phenylpropanoate (190.9 mg, 0.4332 mmol), CuI (26.0 mg, 0.136 mmol) and bis(triphenylphosphine)palladium(1.1) chloride (88.8 mg, 0.126 mmol). The vial was sealed with a Teflon-lined septum, evacuated and backfilled with nitrogen (this process was repeated a total of three times). A solution of ethynylcyclopropane (52.5 mg, 0.794 mmol) in MeCN (3.00 mL) was added followed by triethylamine (200.0 μL, 1.435 mmol). The mixture was stirred at room temperature for 16 h. The reaction was then concentrated in vacuo. The residue was purified on silica gel (40 g, 0-50% EtOAc in hexanes) to give the desired product as a brown semi-oil (131.3 mg, 80%). LCMS calculated for $C_{22}H_{20}ClN_2O_2$ (M+H)$^+$: m/z=379.1; found 379.0.

Step 4. 2-[5-Chloro-3-(cyclopropylethynyl)-2H-indazol-2-yl]-N-hydroxy-3-phenylpropanamide To a suspension of hydroxylamine hydrochloride (99.6 mg, 1.43 mmol) in MeOH (0.50 mL) was added a solution of KOH (156.8 mg, 2.795 mmol) in MeOH (0.50 mL). The resulting white suspension was stirred at room temperature for 30 min, and then cooled to 0° C. A solution of methyl 2-[5-chloro-3-(cyclopropylethynyl)-2H-indazol-2-yl]-3-phenylpropanoate (52.6 mg, 0.139 mmol) in MeOH (1.0 mL) was added. The reaction was stirred at 0° C. for 30 min, and then neutralized with 0.5 mL 4.0 M HCl (aq). The mixture was diluted with MeOH and filtered. The filtrate was purified using RP-HPLC (Waters XBridge™ C18 column, 30 mm×100 mm, 5 μm particle size, eluting with a gradient of MeCN/water containing 0.15% NH$_4$OH, at flow rate of 60 mL/min) to afford compound (I-0005) as a white solid (8.4 mg, 16%). LCMS calculated for $C_{21}H_{19}ClN_3O_2$ (M+H)$^+$: m/z=380.1; found 380.1, IC50: 22 nM.

TABLE 9

The compounds listed in Table 9 were prepared in accordance with the synthetic protocols set forth in Scheme 19 and Example 13, using the appropriate starting materials.

| No. | Name | Structure $^1$H-NMR | LCMS (M + H)$^+$ |
|---|---|---|---|
| I-0136 | 2-(7-chloro-3-(cyclopropylethynyl)-2H-indazol-2-yl)-N-hydroxy-3-phenylpropanamide | | 380.1 |
| I-0206 | 2-(3-(cyclopropylethynyl)-4,5,6,7-tetrahydro-2H-indazol-2-yl)-N-hydroxy-3-phenylpropanamide | $^1$H NMR (500 MHz, DMSO) δ 7.21 (t, J = 7.3 Hz, 2H), 7.16 (t, J = 7.3 Hz, 1H), 7.09 (d, J = 7.3 Hz, 2H), 4.97 (dd, J = 8.6, 6.5 Hz, 1H), 3.38-3.26 (m, 2H), 2.49 (m, 2H), 2.33 (m, 2H), 1.67 (m, 2H), 1.63-1.57 (m, 2H), 1.54 (m, 1H), 0.92-0.85 (m, 2H), 0.72 (m, 2H). | 350.2 |

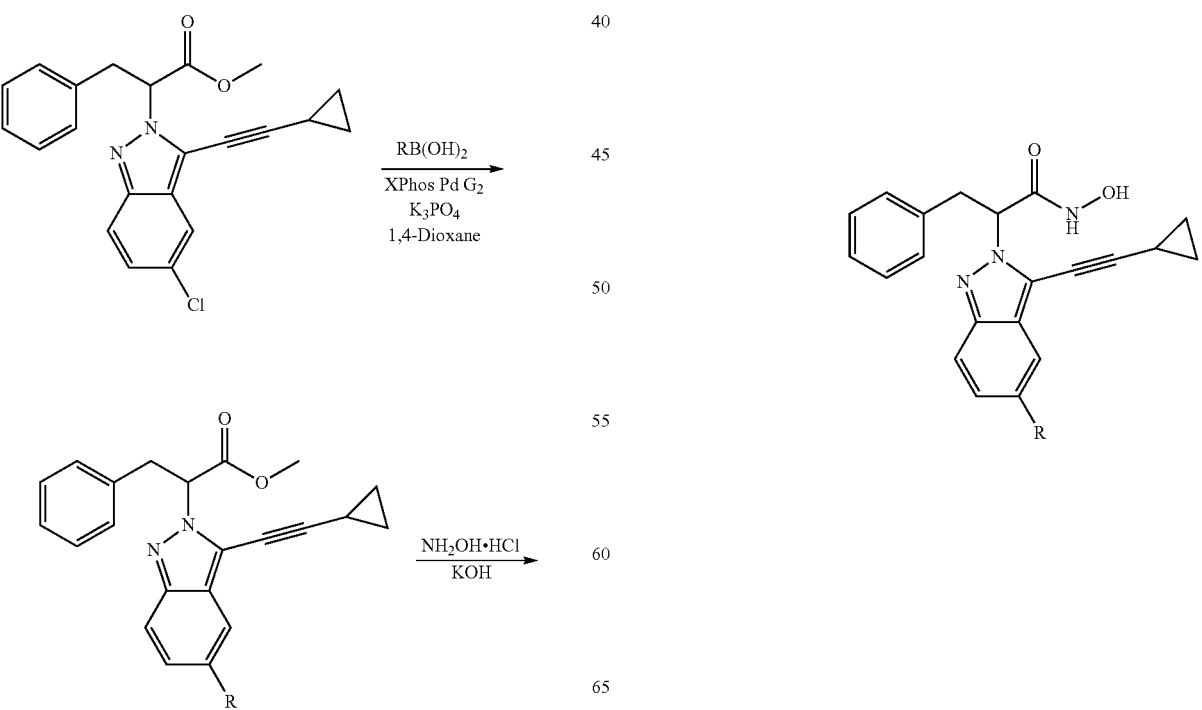

Scheme 20

Example 14

2-[3-(Cyclopropylethynyl)-5-phenyl-2H-indazol-2-yl]-hydroxy-3-phenylpropanamide (I-0025)

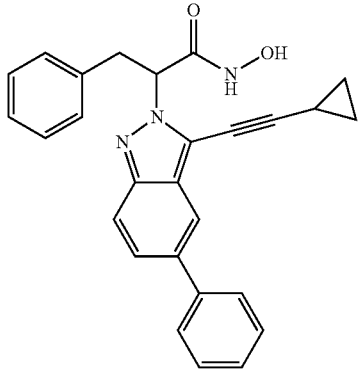 [SMILES: O=C(NO)C(Cc1ccccc1)n1nc2ccc(-c3ccccc3)cc2c1C#CC1CC1]

Step 1. Methyl 2-[3-(cyclopropylethynyl)-5-phenyl-2H-1-indazol-2-yl]-3-phenylpropanoate

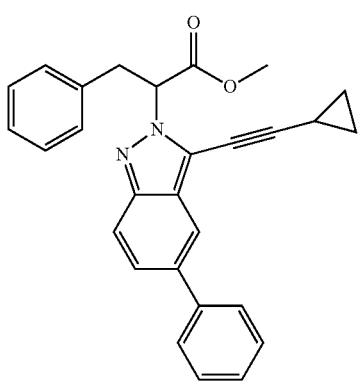 [SMILES: COC(=O)C(Cc1ccccc1)n1nc2ccc(-c3ccccc3)cc2c1C#CC1CC1]

To a screw-cap vial equipped with a magnetic stir bar was added 4,4,5,5-tetramethyl-2-phenyl-1,3,2-dioxaborolane (43.9 mg, 0.215 mmol), dicyclohexyl(2',4',6'-triisopropylbiphenyl-2-yl)phosphine-(2'-aminobiphenyl-2-yl)(chloro)palladium (1:1) (XPhos Pd G2, Aldrich, 9.6 mg, 0.0122 mmol), and potassium phosphate (87.3 mg, 0.411 mmol). The vial was sealed with a Teflon-lined septum, evacuated and backfilled with nitrogen (this process was repeated a total of three times). A solution of methyl 2-[5-chloro-3-(cyclopropylethynyl)-2H-indazol-2-yl]-3-phenylpropanoate (33.5 mg, 0.0884 mmol) in 1,4-dioxane (1.0 mL) was added followed by degassed water (0.10 mL). The reaction was stirred at 80° C. for 1 h. After cooling to room temperature, the reaction was filtered through a silica gel plug (eluted with EtOAc). The filtrate was concentrated. The resulting residue was purified on silica gel (40 g, 0-100% EtOAc in hexanes) to give the desired product as a pale yellow semi-oil (30.3 mg, 82%). LCMS calculated for $C_{28}H_{25}N_2O_2$ (M+H)$^+$: m/z=421.2; found 421.2.

Step 2. 2-[3-(Cyclopropylethynyl)-5-phenyl-2H-indazol-2-yl]-N-hydroxy-3-phenylpropanamide To a suspension of hydroxylamine hydrochloride (52.6 mg, 0.757 mmol) in MeOH (0.3 mL) was added a solution of KOH (66.6 mg, 1.19 mmol) in MeOH (0.5 mL). The resulting white suspension was stirred at room temperature for 30 min, and then cooled to 0° C. A solution of methyl 2-[3-(cyclopropylethynyl)-5-phenyl-2H-indazol-2-yl]-3-phenylpropanoate (30.3 mg, 0.0720 mmol) in MeOH (1.0 mL) was added. The reaction was stirred at 0° C. for 30 min, and then neutralized with 0.20 mL 4.0 M HCl (aq). The mixture was diluted with MeOH and filtered. The filtrate was purified using RP-HPLC (Waters SunFire™ C18 column, 30 mm×100 mm, 5 μm particle size, eluting with a gradient of acetonitrile/water containing 0.1% TFA, at flow rate of 60 mL/min) to afford compound (I-0025) as a white solid (15.2 mg). LCMS calculated for $C_{27}H_{24}N_3O_2$ (M+H)$^+$: m/z=422.2; found 422.2. IC50: 134 nM.

TABLE 10

The compounds in Table 10 were prepared in accordance with the synthetic protocols set forth in Scheme 14 and Example 14, using the appropriate starting materials.

| No. | Name | Structure $^1$H-NMR | LCMS (M + H)$^+$ |
|---|---|---|---|
| I-0026 | 4-(3-(cyclopropylethynyl)-2-(1-(hydroxyamino)-1-oxo-3-phenylpropan-2-yl)-2H-indazol-5-yl)benzamide | | 465.2 |

TABLE 10-continued

The compounds in Table 10 were prepared in accordance with the synthetic protocols set forth in Scheme 14 and Example 14, using the appropriate starting materials.

| No. | Name | Structure ¹H-NMR | LCMS (M + H)⁺ |
|---|---|---|---|
| I-0027 | 2-(3-(cyclopropylethynyl)-5-(2,6-difluorophenyl)-2H-indazol-2-yl)-N-hydroxy-3-phenylpropanamide | | 458.2 |
| I-0028 | 2-(3-(cyclopropylethynyl)-5-(1-methyl-1H-pyrazol-5-yl)-2H-indazol-2-yl)-N-hydroxy-3-phenylpropanamide | | 426.2 |
| I-0029 | 2-(3-(cyclopropylethynyl)-5-(pyridin-4-yl)-2H-indazol-2-yl)-N-hydroxy-3-phenylpropanamide | | 423.2 |

TABLE 10-continued

The compounds in Table 10 were prepared in accordance with the synthetic protocols set forth in Scheme 14 and Example 14, using the appropriate starting materials.

| No. | Name | Structure <br> ¹H-NMR | LCMS (M + H)⁺ |
|---|---|---|---|
| I-0030 | 2-(3-(cyclopropylethynyl)-5-(pyrimidin-5-yl)-2H-indazol-2-yl)-N-hydroxy-3-phenylpropanamide | 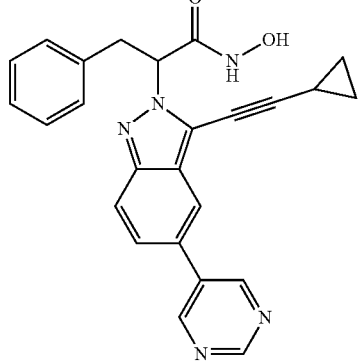<br>¹H NMR (500 MHz, DMSO) δ 9.18 (s, 2H), 9.15 (s, 1H), 7.98 (dd, J = 1.5, 0.7 Hz, 1H), 7.83 (dd, J = 9.0, 0.7 Hz, 1H), 7.70 (dd, J = 9.0, 1.5 Hz, 1H), 7.19-7.03 (m, 5H), 5.53 (dd, J = 10.1, 5.1 Hz, 1H), 3.62-3.47 (m, 2H), 1.68 (m, 1H), 0.99 (m, 2H), 0.93-0.85 (m, 2H). | 424.2 |
| I-0031 | 2-(3-(cyclopropylethynyl)-5-(2-methoxypyrimidin-5-yl)-2H-indazol-2-yl)-N-hydroxy-3-phenylpropanamide | 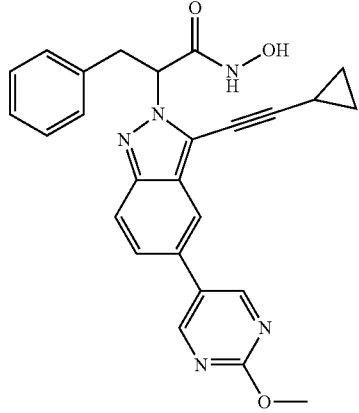 | 454.2 |
| I-0032 | 2-(3-(cyclopropylethynyl)-5-methyl-2H-indazol-2-yl)-N-hydroxy-3-phenylpropanamide | 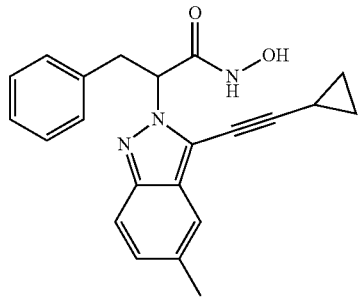<br>¹H NMR (500 MHz, DMSO) δ 7.56 (d, J = 9.0 Hz, 1H), 7.28-7.26 (m, 1H), 7.18-7.01 (m, 6H), 5.43 (dd, J = 9.9, 5.2 Hz, 1H), 3.60-3.41 (m, 2H), 2.34 (s, 3H), 1.65 (m, 1H), 1.03-0.91 (m, 2H), 0.88-0.78 (m, 2H). | 360.2 |

TABLE 10-continued

The compounds in Table 10 were prepared in accordance with the synthetic protocols set forth in Scheme 14 and Example 14, using the appropriate starting materials.

| No. | Name | Structure<br>¹H-NMR | LCMS<br>(M + H)⁺ |
|---|---|---|---|
| I-0044 | 2-(3-(cyclopropylethynyl)-5-(1-methyl-1H-pyrazol-4-yl)-2H-indazol-2-yl)-N-hydroxy-3-phenylpropanamide | 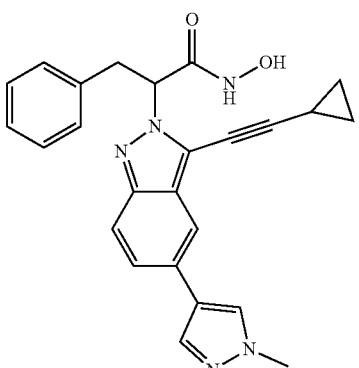 | 426.2 |
| I-0045 | 2-(3-(cyclopropylethynyl)-5-(pyridin-3-yl)-2H-indazol-2-yl)-N-hydroxy-3-phenylpropanamide | 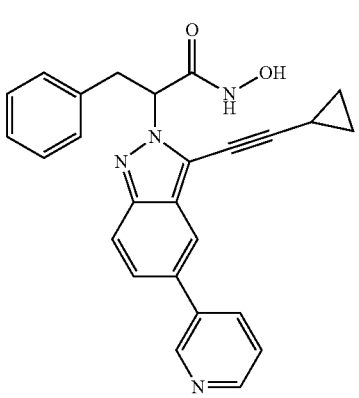 [SMILES: O=C(NO)C(Cc1ccccc1)n1nc2ccc(-c3ccncc3)cc2c1C#CC1CC1]<br>¹H NMR (500 MHz, DMSO) δ 9.13 (d, J = 2.0 Hz, 1H), 8.70 (dd, J = 5.2, 1.3 Hz, 1H), 8.53 (d, J = 8.1 Hz, 1H), 7.98-7.96 (m, 1H), 7.86-7.82 (m, 1H), 7.78 (dd, J = 8.1, 5.2 Hz, 1H), 7.70 (dd, J = 9.1, 1.7 Hz, 1H), 7.18-7.04 (m, 5H), 5.53 (dd, J = 10.2, 5.1 Hz, 1H), 3.62-3.48 (m, 2H), 1.69 (m, 1H), 0.99 (m, 2H), 0.93-0.84 (m, 2H). | 423.2 |
| I-0046 | 2-(3-(cyclopropylethynyl)-5-(6-methoxypyridin-3-yl)-2H-indazol-2-yl)-N-hydroxy-3-phenylpropanamide | 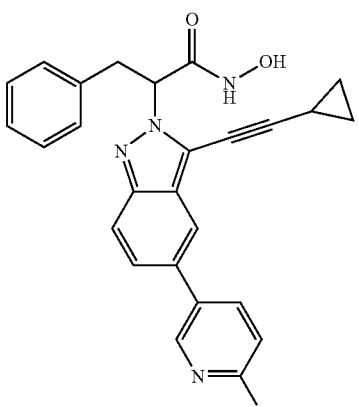 | 453.2 |

TABLE 10-continued

The compounds in Table 10 were prepared in accordance with the synthetic protocols set forth in Scheme 14 and Example 14, using the appropriate starting materials.

| No. | Name | Structure ¹H-NMR | LCMS (M + H)⁺ |
|---|---|---|---|
| I-0137 | 2-(3-(cyclopropylethynyl)-7-(1-methyl-1H-pyrazol-5-yl)-2H-indazol-2-yl)-N-hydroxy-3-phenylpropanamide | | 426.2 |
| I-0138 | 4-(3-(cyclopropylethynyl)-2-(1-(hydroxyamino)-1-oxo-3-phenylpropan-2-yl)-2H-indazol-7-yl)benzamide | | 465.2 |
| I-0139 | 4-(3-(cyclopropylethynyl)-2-(1-(hydroxyamino)-1-oxo-3-phenylpropan-2-yl)-2H-indazol-7-yl)-N,N-dimethylbenzamide | | 493.2 |
| I-0154 | 2-(3-(cyclopropylethynyl)-7-(pyridin-4-yl)-2H-indazol-2-yl)-N-hydroxy-3-phenylpropanamide | | 423.2 |
| I-0155 | 2-(3-(cyclopropylethynyl)-7-(pyridin-3-yl)-2H-indazol-2-yl)-N-hydroxy-3-phenylpropanamide | | 423.2 |

TABLE 10-continued

The compounds in Table 10 were prepared in accordance with the synthetic protocols set forth in Scheme 14 and Example 14, using the appropriate starting materials.

| No. | Name | Structure ¹H-NMR | LCMS (M + H)⁺ |
|---|---|---|---|
| I-0156 | 2-(3-(cyclopropylethynyl)-7-(pyrimidin-5-yl)-2H-indazol-2-yl)-N-hydroxy-3-phenylpropanamide | | 424.2 |
| I-0157 | 3-(3-(cyclopropylethynyl)-2-(1-(hydroxyamino)-1-oxo-3-phenylpropan-2-yl)-2H-indazol-7-yl)benzamide | | 465.2 |
| I-0158 | 3-(3-(cyclopropylethynyl)-2-(1-(hydroxyamino)-1-oxo-3-phenylpropan-2-yl)-2H-indazol-7-yl)-N-methylbenzamide | | 479.2 |
| I-0159 | 3-(3-(cyclopropylethynyl)-2-(1-(hydroxyamino)-1-oxo-3-phenylpropan-2-yl)-2H-indazol-7-yl)-N,N-dimethylbenzamide | | 493.2 |

TABLE 10-continued

The compounds in Table 10 were prepared in accordance with the synthetic protocols set forth in Scheme 14 and Example 14, using the appropriate starting materials.

| No. | Name | Structure <br> ¹H-NMR | LCMS (M + H)⁺ |
|---|---|---|---|
| I-0160 | 2-(7-cyclopropyl-3-(cyclopropylethynyl)-2H-indazol-2-yl)-N-hydroxy-3-phenylpropanamide | | 386.2 |
| I-0161 | 2-(3-(cyclopropylethynyl)-7-methyl-2H-indazol-2-yl)-N-hydroxy-3-phenylpropanamide | | 360.2 |
| I-0165 | 2-(3-(cyclopropylethynyl)-7-(1-(2-methoxyethyl)-3-methyl-1H-pyrazol-4-yl)-2H-indazol-2-yl)-N-hydroxy-3-phenylpropanamide | | 484.2 |
| I-0166 | 2-(3-(cyclopropylethynyl)-7-(3-methyl-1H-pyrazol-4-yl)-2H-indazol-2-yl)-N-hydroxy-3-phenylpropanamide | | 426.2 |

Example 15

2-[1-Benzyl-2-(hydroxyamino)-2-oxethyl]-3-(cyclopropylethynyl)-N-[2-(tetrahydro-2H-pyran-4-yl)ethyl]-2H-indazole-7-carboxamide (I-0197)

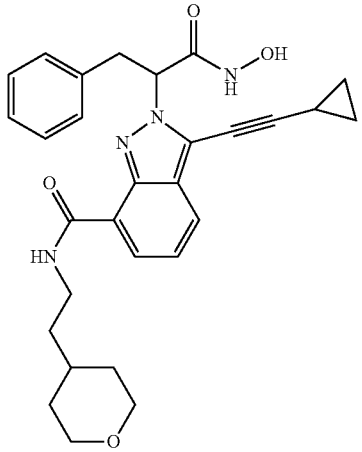 [SMILES: O=C(NCCC1CCOCC1)c1cccc2c(C#CC3CC3)n(C(Cc3ccccc3)C(=O)NO)nc12]

Step 1. Methyl 3-phenyl-2-(7-(2-(tetrahydro-2H-pyran-4-yl)ethylcarbamoyl)-2H-indazol-2-yl)propanoate

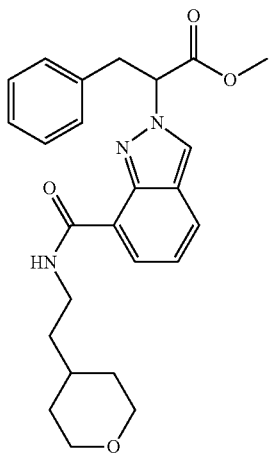 [SMILES: COC(=O)C(Cc1ccccc1)n1cc2cccc(C(=O)NCCC3CCOCC3)c2n1]

The title compound was prepared as depicted in Example 4, using the appropriate starting materials. LCMS calculated for $C_{25}H_{30}N_3O_4$ (M+H)$^+$: m/z=436.2; found 436.2.

Step 2. Methyl 2-[3-iodo-7-({[2-(tetrahydro-2H-pyran-4-yl)ethyl]amino}carbonyl)-2H-indazol-2-yl]-3-phenylpropanoate

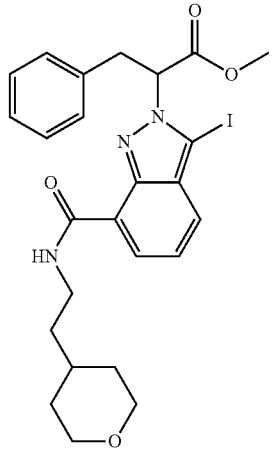 [SMILES: COC(=O)C(Cc1ccccc1)n1nc2c(C(=O)NCCC3CCOCC3)cccc2c1I]

To a solution of methyl 3-phenyl-2-[7-({[2-(tetrahydro-2H-pyran-4-yl)ethyl]amino}carbonyl)-2H-indazol-2-yl]propanoate (148.7 mg, 0.3414 mmol) in $CH_2Cl_2$ (3.00 mL) at room temperature was added N-iodosuccinimide (102.9 mg, 0.4574 mmol) followed by trifluoroacetic acid (40.0 µL, 0.519 mmol). The reaction was heated to 50° C. for 16 h. The mixture was then diluted with EtOAc, washed with 1 M $NaHSO_3$ (aq), 1 M $Na_2CO_3$ (aq) and brine. The organic layer was dried over anhydrous $Na_2SO_4$, filtered and concentrated. The residue was purified on silica gel (40 g, 0-50% EtOAc in hexanes) to give the desired product as a colorless oil (68.3 mg, 36%). LCMS calculated for $C_{25}H_{29}IN_3O_4$ (M+H)$^+$: m/z=562.1; found 562.1.

Step 3. Methyl 2-[3-(cyclopropylethynyl)-7-({[2-(tetrahydro-2H-pyran-4-yl)ethyl]amino}carbonyl)-2H-indazol-2-yl]-3-phenylpropanoate

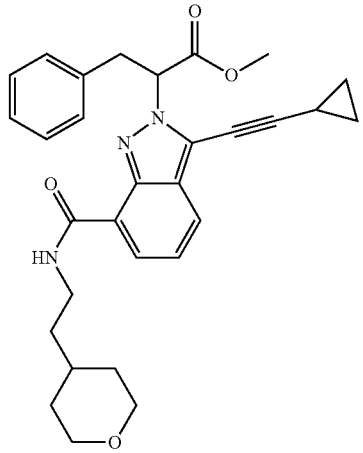 [SMILES: COC(=O)C(Cc1ccccc1)n1nc2c(C(=O)NCCC3CCOCC3)cccc2c1C#CC1CC1]

To a screw-cap vial equipped with a magnetic stir bar was added methyl 2-[3-iodo-7-({[2-(tetrahydro-2H-pyran-4-yl)ethyl]amino}carbonyl)-2H-indazol-2-yl]-3-phenylpropanoate (68.3 mg, 0.122 mmol), CuI (13.0 mg, 0.0682 mmol) and bis(triphenylphosphine)palladium(II) chloride (26.2 mg, 0.0373 mmol). The vial was sealed with a Teflon-lined septum, evacuated and backfilled with nitrogen (this process was repeated a total of three times). A solution of ethynylcyclopropane (30.0 μL, 0.354 mmol) in MeCN (2.00 mL) was added followed by triethylamine (70.0 μL, 0.502 mmol). The mixture was stirred at room temperature for 16 h. The reaction was then concentrated in vacuo. The residue was purified on silica gel (20 g, 0-100% EtOAc in hexanes) to give the desired product as a brown semi-oil (60.8 mg). LCMS calculated for $C_{30}H_{34}N_3O_4$ $(M+H)^+$: m/z=500.3; found 500.2.

Step 4. 2-[1-Benzyl-2-(hydroxyamino)-2-oxoethyl]-3-(cyclopropylethynyl)-N-[2-(tetrahydro-2H-pyran-4-yl)ethyl]-2H-indazole-7-carboxamide To a suspension of hydroxylamine hydrochloride (133.5 mg, 1.921 mmol) in MeOH (0.20 mL) was added a solution of KOH (158.1 mg, 2.818 mmol) in MeOH (0.80 mL). The resulting white suspension was stirred at room temperature for 30 min, and then cooled to 0° C. A solution of methyl 2-[3-(cyclopropylethynyl)-7-({[2-(tetrahydro-2H-pyran-4-yl)ethyl]amino}carbonyl)-2H-indazol-2-yl]-3-phenylpropanoate (60.8 mg, 0.122 mmol) in MeOH (1.0 mL) was added. The reaction mixture was stirred at 0° C. for 30 min, and then neutralized with 0.6 mL 4.0 M HCl (aq). The mixture was diluted with MeOH and filtered. The filtrate was purified using RP-HPLC (Waters SunFire™ C18 column, 30 mm×100 mm, 5 μm particle size, eluting with a gradient of acetonitrile/water containing 0.1% TFA, at flow rate of 60 mL/min) to afford compound (I-0197) as a white solid (23.0 mg). LCMS calculated for $C_{29}H_{33}N_4O_4$ $(M+H)^+$: m/z=501.3; found 501.2. $^1H$ NMR (500 MHz, DMSO) δ 10.95 (s, 1H), 9.03 (t, J=5.5 Hz, 1H), 7.99 (dd, J=7.1, 1.0 Hz, 1H), 7.75 (dd, J=8.3, 1.0 Hz, 1H), 7.22 (dd, J=8.3, 7.1 Hz, 1H), 7.19-7.07 (m, 5H), 5.55 (dd, J=10.2, 5.1 Hz, 1H), 3.81 (in, 2H), 3.65 (m, 1H), 3.57 (m, 2H), 3.45 (m, 1H), 3.33-3.24 (m, 2H), 1.77-1.63 (m, 4H), 1.57 (m, 2H), 1.22 (m, 2H), 1.00 (m, 2H), 0.90 (m, 2H). IC50: 16 nM.

Scheme 21

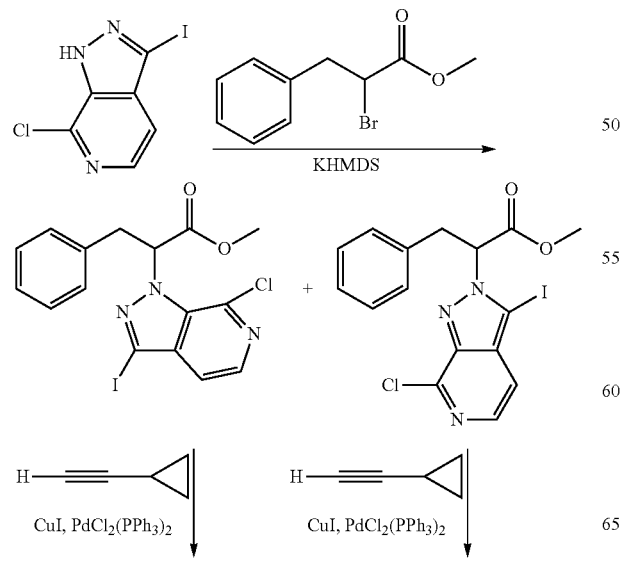

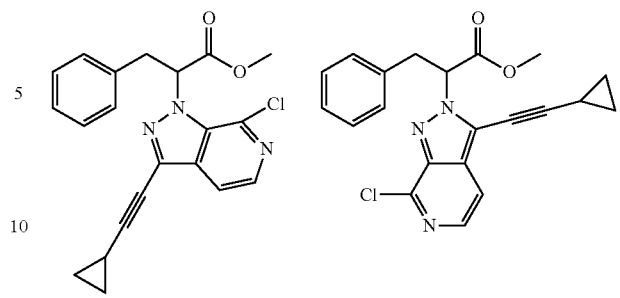

| NH$_2$OH·HCl
KOH

| NH$_2$OH·HCl
KOH

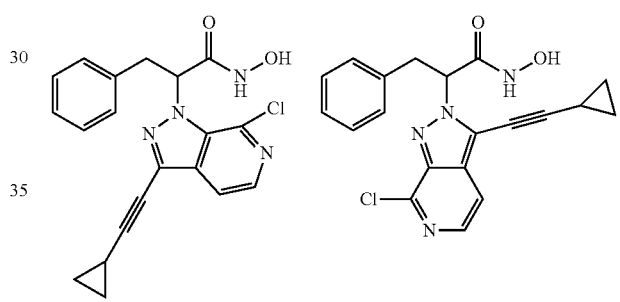

Example 16

2-[7-Chloro-3-(cyclopropylethynyl)-1H-pyrazolo[3,4-c]pyridin-1-yl]-N-hydroxy-3-phenylpropanamide (I-0126)

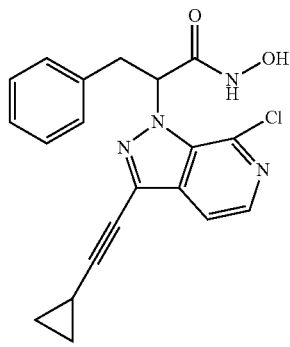 [SMILES: O=C(NO)C(Cc1ccccc1)n1nc(C#CC2CC2)c2ccnc(Cl)c21]

Step 1. 7-chloro-3-iodo-1H-pyrazolo[3,4-c]pyridine

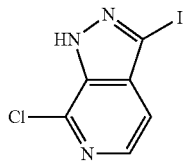 [SMILES: Clc1nccc2c(I)n[nH]c12]

To a solution of 7-chloro-1H-pyrazolo[3,4-c]pyridine (1032 mg, 6.720 mmol) in DMF (18 mL) was added N-iodosuccinimide (2.32 g, 10.3 mmol). The reaction mixture was heated to 80° C. for 1 h. The mixture was then diluted with EtOAc, washed with 1 M NaHSO$_3$ (aq), 1 M Na$_2$CO$_3$ (aq) and brine. The organic layer was dried over anhydrous Na$_2$SO$_4$, filtered and concentrated. The residue was triturated with 10% CH$_2$Cl$_2$ in hexanes to give the desired product as a pale yellow solid (1.69 g, 90%). LCMS calculated for C$_6$H$_4$ClIN$_3$ (M+H)$^+$: m/z=279.9; found 279.9.

Step 2. Methyl 2-(7-chloro-3-iodo-1H-pyrazolo[3,4-c]pyridin-1-yl)-3-phenylpropanoate and methyl 2-(7-chloro-3-iodo-2H-pyrazolo[3,4-c]pyridin-2-yl)-3-phenylpropanoate

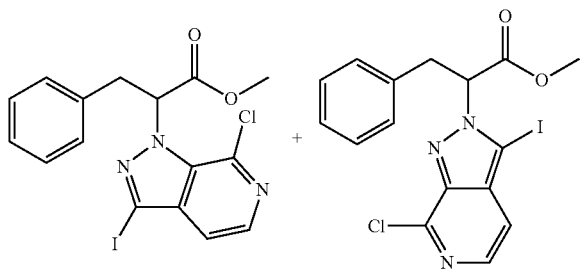

To a solution of 7-chloro-3-iodo-1H-pyrazolo[3,4-c]pyridine (1068 mg, 3.822 mmol) in THF (8.00 mL) at −78° C. was added 1.0 M KHMDS in THF (4.00 mL, 4.00 mmol) dropwise. The mixture was allowed to warm to 0° C. and stirred for 1 h. The reaction was cooled back to −78° C. A solution of methyl 2-bromo-3-phenylpropanoate (1055 mg, 4.340 mmol) in THF (5.0 mL) was added dropwise. The reaction was allowed to warm to room temperature, and then stirred at 40° C. for 16 h. After cooling down to room temperature, the reaction mixture was diluted with EtOAc, washed with water and brine. The organic layer was dried over anhydrous Na$_2$SO$_4$, filtered and concentrated. The residue was purified on silica gel (120 g, 0-100% EtOAc in hexanes) to give methyl 2-(7-chloro-3-iodo-1H-pyrazolo[3,4-c]pyridin-1-yl)-3-phenylpropanoate (465.7 mg, 28%, LCMS calculated for C$_{16}$H$_{14}$ClIN$_3$O$_2$ (M+H)$^+$: m/z=442.0; found 441.9) and methyl 2-(7-chloro-3-iodo-2H-pyrazolo[3,4-c]pyridin-2-yl)-3-phenylpropanoate (618.1 mg, 38%, LCMS calculated for C$_{16}$H$_{14}$ClIN$_3$O$_2$ (M+H)$^+$: m/z=442.0; found 442.0).

Step 3. Methyl 2-[7-chloro-3-(cyclopropylethynyl)-1H-pyrazolo[3,4-c]pyridin-1-yl]-3-phenylpropanoate

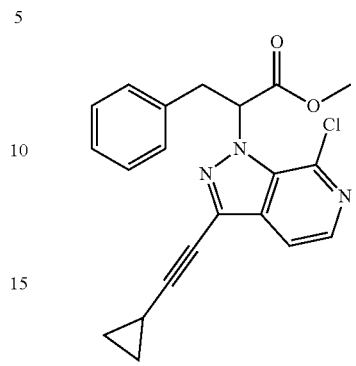

To a screw-cap vial equipped with a magnetic stir bar was added methyl 2-(7-chloro-3-iodo-1H-pyrazolo[3,4-c]pyridin-1-yl)-3-phenylpropanoate (465.7 mg, 1.054 mmol), CuI (105.0 mg, 0.5513 mmol) and bis(triphenylphosphine)palladium(II) chloride (220.1 mg, 0.3136 mmol). The vial was sealed with a Teflon-lined septum, evacuated and backfilled with nitrogen (this process was repeated a total of three times). A solution of ethynylcyclopropane (84.6 mg, 1.28 mmol) in MeCN (5.00 mL) was added followed by triethylamine (550.0 µL, 3.946 mmol). The mixture was stirred at room temperature for 16 h. The reaction was then concentrated in vacuo. The residue was purified on silica gel (40 g, 0-100% EtOAc in hexanes) to give the desired product as a brown semi-oil (352.4 mg, 88%). LCMS calculated for C$_{21}$H$_{19}$ClN$_3$O$_2$ (M+H)$^+$: m/z=380.1; found 380.1.

Step 4. 2-[7-Chloro-3-(cyclopropylethynyl)-1H-pyrazolo[3,4-c]pyridin-1-yl]-N-hydroxy-3-phenylpropanamide To a suspension of hydroxylamine hydrochloride (78.4 mg, 1.13 mmol) in MeOH (0.2 mL) was added a solution of KOH (79.6 mg, 1.419 mmol) in MeOH (0.4 mL). The resulting white suspension was stirred at room temperature for 30 min, and then cooled to 0° C. A solution of methyl 2-[7-chloro-3-(cyclopropylethynyl)-1H-pyrazolo[3,4-c]pyridin-1-yl]-3-phenylpropanoate (28.9 mg, 0.0761 mmol) in MeOH (1.0 mL) was added. The reaction was stirred at 0° C. for 30 min, and then neutralized with 0.30 mL 4.0 M (aq). The mixture was diluted with MeOH and filtered. The filtrate was purified using RP-HPLC (Waters SunFire™ C18 column, 30 mm×100 mm, 5 µm particle size, eluting with a gradient of acetonitrile/water containing 0.1% TFA, at flow rate of 60 ml min) to afford compound (I-0126) as a white solid (7.8 mg). LCMS calculated for C$_{20}$H$_{18}$ClN$_4$O$_2$ (M+H)$^+$: m/z=381.1; found 381.1. IC50: 101 nM.

TABLE 11

The following compound was prepared in accordance with the synthetic protocols set forth in Scheme 21 and Example 16, using the appropriate starting materials.

| No. | Name | Structure<br>¹H-NMR | LCMS<br>(M + H)⁺ |
|---|---|---|---|
| I-0009 | 2-(5-chloro-3-(cyclopropylethynyl)-1H-indazol-1-yl)-N-hydroxy-3-phenylpropanamide | ¹H NMR (500 MHz, DMSO) δ 7.74 (d, J = 9.0 Hz, 1H), 7.65 (d, J = 1.8 Hz, 1H), 7.40 (dd, J = 9.0, 1.8 Hz, 1H), 7.20-7.07 (m, 5H), 5.39 (dd, J = 8.8, 6.7 Hz, 1H), 3.57-3.41 (m, 2H), 1.67-1.61 (m, 1H), 0.97-0.92 (m, 2H), 0.87-0.83 (m, 2H). | 380.1 |

Example 17

2-[7-Chloro-3-(cyclopropylethynyl)-2H-pyrazolo[3,4-c]pyridin-2-yl]-N-hydroxy-3-phenylpropanamide (I-0127)

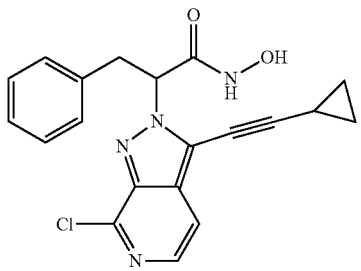 [SMILES: O=C(NO)C(Cc1ccccc1)n1nc2c(Cl)nccc2c1C#CC1CC1]

Step 1. Methyl 2-[7-chloro-3-(cyclopropylethynyl)-2H-pyrazolo[3,4-c]pyridin-2-yl]-3-phenylpropanoate

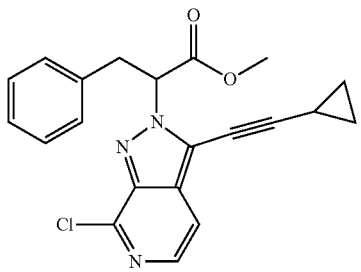 [SMILES: COC(=O)C(Cc1ccccc1)n1nc2c(Cl)nccc2c1C#CC1CC1]

To a screw-cap vial equipped with a magnetic stir bar was added methyl 2-(7-chloro-3-iodo-2H-pyrazolo[3,4-c]pyridin-2-yl)-3-phenylpropanoate (525.0 mg, 1.189 mmol), CuI (117.1 mg, 0.6148 mmol) and bis(triphenylphosphine)palladium(II) chloride (300.7 mg, 0.4284 mmol). The vial was sealed with a Teflon-lined septum, evacuated and backfilled with nitrogen (this process was repeated a total of three times). A solution of ethynylcyclopropane (96.2 mg, 1.46 mmol) in MeCN (5.00 mL) was added followed by triethylamine (442.9 mg, 4.377 mmol). The mixture was stirred at room temperature for 5 h. Additional ethynylcyclopropane (48.6 mg, 0.735 mmol) in MeCN (2.00 mL) was added. The mixture was stirred at room temperature for another 16 h. The reaction was then concentrated. The residue was purified on silica gel (40 g, 0-100% EtOAc in hexanes) to give the desired product as a brown semi-oil (174.2 mg, 39%). LCMS calculated for $C_{21}H_{19}ClN_3O_2$ (M+H)⁺: m/z=380.1; found 380.1.

Step 2. 2-[7-chloro-3-(cyclopropylethynyl)-2H-pyrazolo[3,4-c]pyridin-2-yl]-N-hydroxy-3-phenylpropanamide

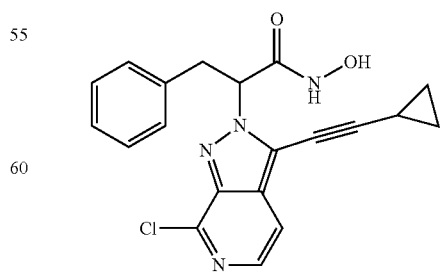

To a suspension of hydroxylamine hydrochloride (70.7 mg, 1.02 mmol) in MeOH (0.20 mL) was added a solution of KOH (79.6 mg, 1.419 mmol) in MeOH (0.40 mL). The resulting white suspension was stirred at room temperature for 30 min, and then cooled to 0° C. A solution of methyl 2-[7-chloro-3-(cyclopropylethynyl)-2H-pyrazolo[3,4-c]pyridin-2-yl]-3-phenylpropanoate (24.2 mg, 0.0637 mmol) in MeOH (1.0 mL) was added. The reaction mixture was stirred at 0° C. for 30 min, and then neutralized with 0.3 mL 4.0 M HCl (a.q). The mixture was diluted with MeOH and filtered. The filtrate was purified using RP-HPLC (Waters SunFire™ C18 column, 30 mm×100 mm, 5 μm particle size, eluting with a gradient of acetonitrile/water containing 0.1% TFA, at flow rate of 60 mL/min) to afford compound (I-0127) as a white solid (5.9 mg). LCMS calculated for $C_{20}H_{18}ClN_4O_2$ $(M+H)^+$: m/z=381.1; found 381.0. IC50: 5.7 nM.

Scheme 22

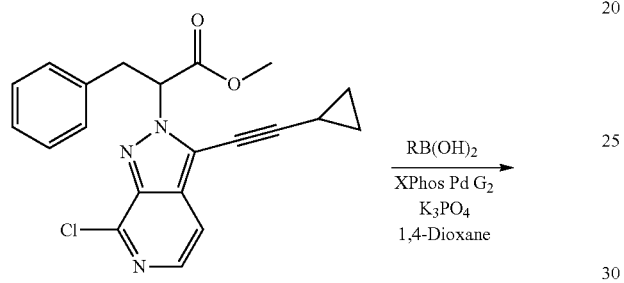

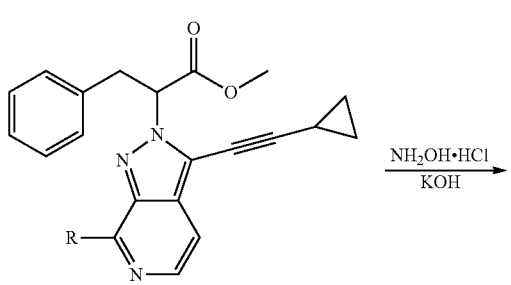

Example 18

2-[3-(Cyclopropylethynyl)-7-(1-methyl-1H-pyrazol-5-yl)-2H-pyrazolo[3,4-c]pyridin-2-yl]-N-hydroxy-3-phenylpropanamide (I-0128)

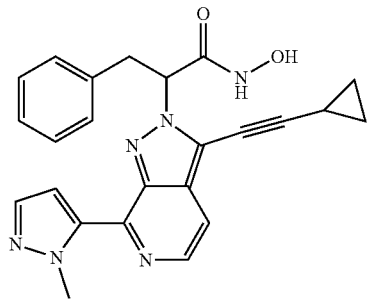 [SMILES: Cn1nccc1-c1nccc2c(C#CC3CC3)n(C(Cc3ccccc3)C(=O)NO)nc12]

To a screw-cap vial equipped with a magnetic stir bar was added 1-methyl-5-(4,4,5,5-tetramethyl-1,3,2-dioxaborolan-2-yl)-1H-pyrazole (36.3 mg, 0.174 mmol), dicyclohexyl(2',4',6'-triisopropylbiphenyl-2-yl)phosphine-(2'-aminobiphenyl-2-yl)(chloro)palladium (1:1) (XPhos Pd G2, Aldrich, 7.6 mg, 0.0097 mmol), and potassium phosphate (73.4 mg, 0.346 mmol). The vial was sealed with a Teflon-lined septum, evacuated and backfilled with nitrogen (this process was repeated a total of three times). A solution of methyl 2-[7-chloro-3-(cyclopropylethynyl)-2H-pyrazolo[3,4-c]pyridin-2-yl]-3-phenylpropanoate (31.9 mg, 0.0840 mmol) in 1,4-dioxane (1.00 mL) was added followed by degassed water (0.10 mL). The reaction was stirred at 80° C. for 1 h. After cooling to room temperature, the reaction was diluted with $CH_2Cl_2$, filtered and concentrated. The resulting residue was dissolved in 1:1 THF/MeOH (1.0 mL).

To another vial containing hydroxylamine hydrochloride (83.3 mg, 1.20 mmol) was added MeOH (0.20 mL) followed by a solution of KOH (99.4 mg, 1.772 mmol) in MeOH (0.50 mL). The resulting white suspension was stirred at room temperature for 30 min, and then cooled to 0° C. The above THF/MeOH solution was added. The reaction mixture was stirred at 0° C. for 30 min, and then neutralized with 0.40 mL 4.0 M HCl (aq). The mixture was diluted with MeOH and filtered. The filtrate was purified using RP-HPLC (Waters SunFire™ C18 column, 30 mm×100 mm, 5 μm particle size, eluting with a gradient of acetonitrile/water containing 0.1% TFA, at flow rate of 60 mL/min) to afford compound (I-0128) as a yellow solid (14.6 mg). LCMS calculated for $C_{24}H_{23}N_6O_2$ $(M+H)^+$: m/z=427.2; found 427.2. IC50: 4.3 nM.

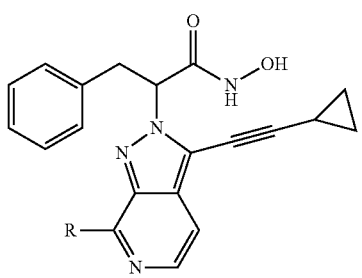

TABLE 12

The compounds in Table 12 were prepared in accordance with the synthetic protocols set forth in Scheme 22 and Example 18, using the appropriate starting materials.

| No. | Name | Structure <br> ¹H-NMR | LCMS (M + H)⁺ |
|---|---|---|---|
| I-0140 | 4-(3-(cyclopropylethynyl)-2-(1-(hydroxyamino)-1-oxo-3-phenylpropan-2-yl)-2H-pyrazolo[3,4-c]pyridin-7-yl)benzamide | 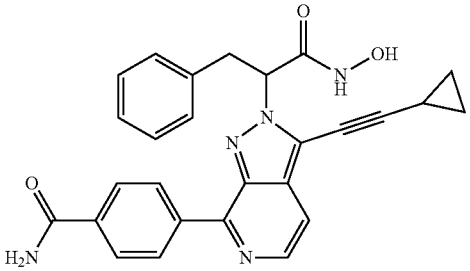 <br> ¹H NMR (500 MHz, DMSO) δ 8.65 (d, J = 8.5 Hz, 2H), 8.24 (d, J = 5.9 Hz, 1H), 8.07 (m, 3H), 7.62 (d, J = 5.9 Hz, 1H), 7.47 (s, 1H), 7.19-7.06 (m, 5H), 5.71 (dd, J = 10.4, 4.9 Hz, 1H), 3.73-3.57 (m, 2H), 1.76-1.69 (m, 1H), 1.02 (m, 2H), 0.93 (m, 2H). | 466.3 |
| I-0141 | 4-(3-(cyclopropylethynyl)-2-(1-(hydroxyamino)-1-oxo-3-phenylpropan-2-yl)-2H-pyrazolo[3,4-c]pyridin-7-yl)-N-methylbenzamide | 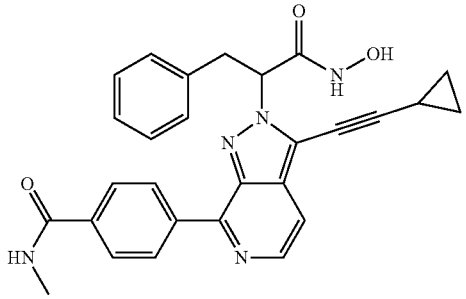 [SMILES: CNC(=O)c1ccc(-c2nccc3c(C#CC4CC4)n(C(Cc4ccccc4)C(=O)NO)nc23)cc1] | 480.2 |
| I-0142 | 4-(3-(cyclopropylethynyl)-2-(1-(hydroxyamino)-1-oxo-3-phenylpropan-2-yl)-2H-pyrazolo[3,4-c]pyridin-7-yl)-N,N-dimethylbenzamide | 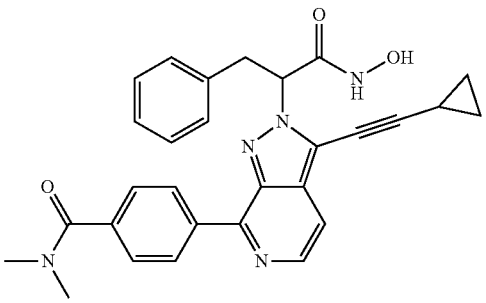 | 494.2 |

TABLE 12-continued

The compounds in Table 12 were prepared in accordance with the synthetic protocols set forth in Scheme 22 and Example 18, using the appropriate starting materials.

| No. | Name | Structure ¹H-NMR | LCMS (M + H)⁺ |
|---|---|---|---|
| I-0207 | 2-(3-(cyclopropylethynyl)-7-(pyrimidin-5-yl)-2H-pyrazolo[3,4-c]pyridin-2-yl)-N-hydroxy-3-phenylpropanamide | 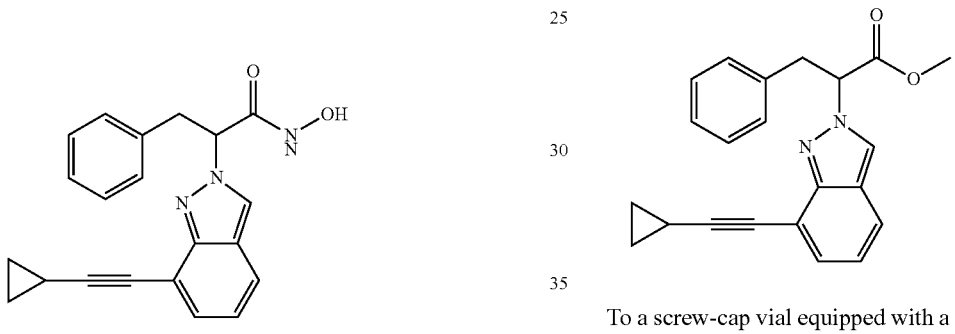 | 425.2 |

Example 19

2-(7-(Cyclopropylethynyl)-2H-indazol-2-yl)-N-hydroxy-3-phenylpropanamide (I-0082)

Step 1. Methyl 2-(7-bromo-2H-1-indazol-2-yl)-3-phenylpropanoate

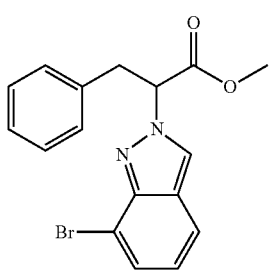 [SMILES: COC(=O)C(Cc1ccccc1)n1cc2cccc(Br)c2n1]

The title compound was prepared as described in Example 1 (Step 1). LCMS calculated for $C_{17}H_{16}BrN_2O_2$ (M+H)⁺: m/z=359.0; found 359.0.

Step 2. 2-[7-(cyclopropylethynyl)-2H-indazol-2-yl]-3-phenylpropanoate

To a screw-cap vial equipped with a magnetic stir bar was added methyl 2-(7-bromo-2H-indazol-2-yl)-3-phenylpropanoate (100.0 mg, 0.2784 mmol), CuI (17.7 mg, 0.0929 mmol) and bis(triphenylphosphine)palladium(II) chloride (58.3 mg, 0.0831 mmol). The vial was sealed with a Teflon-lined septum, evacuated and backfilled with nitrogen (this process was repeated a total of three times). A solution of ethynylcyclopropane (34.2 mg, 0.517 mmol) in MeCN (1.50 mL) was added followed by triethylamine (140.0 µL, 1.004 mmol). The mixture was stirred at room temperature for 16 h. The reaction was then concentrated in vacuo. The residue was purified on silica gel (40 g, 0-50% EtOAc in hexanes) to give the desired product as a brown semi-oil (34.4 mg, 36%). LCMS calculated for $C_{22}H_{21}N_2O_2$ (M+H)⁺: m/z=345.2; found 345.2.

Step 3. 2-(7-(Cyclopropylethynyl)-2H-indazol-2-yl)-N-hydroxy-3-phenylpropanamide To a suspension of hydroxylamine hydrochloride (99.6 mg, 1.43 mmol) in MeOH (0.50 mL) was added a solution of KOH (156.8 mg, 2.795 mmol) in MeOH (0.50 mL). The resulting white suspension was stirred at room temperature for 30 min, and then cooled to 0° C. A solution of methyl 2-[7-(cyclopropylethynyl)-2H-indazol-2-yl]-3-phenylpropanoate (34.4 mg, 0.100 mmol) in MeOH (1.0 mL) was added. The reaction was stirred at 0° C. for 30 min, and then neutralized with 0.5 mL 4.0 M HCl (aq). The mixture was diluted with MeOH and filtered. The filtrate was purified using RP-HPLC (Waters XBridge™ C18 column, 30 mm×100 mm, 5 µm particle size, eluting with a gradient of MeCN/water containing 0.15% NH₄OH at flow rate of 60 mL/min) to afford compound (I-0082) as a white solid (6.8 mg). LCMS calculated for $C_{21}H_{20}N_3O_2$ (M+H)⁺: m/z=346.2; found 346.2. IC50: 372 nM.

TABLE 13

The following compound was prepared using the similar synthetic processes as shown in Example 19, using the appropriate starting materials.

| No. | Name | Structure ¹H-NMR | LCMS (M + H)⁺ |
|---|---|---|---|
| I-0053 | 2-(7-(cyclopropylethynyl)-2H-pyrazolo[4,3-c]pyridin-2-yl)-N-hydroxy-3-phenylpropanamide | ¹H NMR (500 MHz, DMSO) δ 11.23 (s, 1H), 9.45 (s, 1H), 9.37 (s, 1H), 8.34 (s, 1H), 7.29-7.10 (m, 5H), 5.59 (dd, J = 8.7, 7.1 Hz, 1H), 3.67-3.51 (m, 2H), 1.73-1.66 (m, 1H), 1.02-0.95 (m, 2H), 0.86-0.78 (m, 2H). | 347.2 |

Example A

HDAC8 Enzymatic Assay

Materials

HDAC-Glo™ I/II Assay Kit was purchased from Promega Corporation (Madison, Wis.), including the following components: HDAC-Glo I/II Buffer (25 mM Tris buffer, pH 8.0, supplemented with 137 mM: NaCl, 2.7 mM KCl, 1% v/v Triton X-100 and 1 mM: MgCl2), luminogenic substrates Boc-GAK(Ac)-aminoluciferin (HDAC-Glo I/II substrate), proprietary developer reagent (containing trypsin). Human recombinant Histone Deacetylase 8 (HDAC8) was purchased from Enzo Life Sciences (Plymouth Meeting, Pa.).

HDAC8 Assay

The HDAC8 reaction was performed at room temperature in white 384-well polystyrene, flat-bottom microtiter plate (Greiner Bio-one, Monroe, N.C.) in a final volume of 20 μL. Test compounds were first diluted serially in DMSO and 100 nL were transferred to the plate wells by Echo 550 (Labcyte, Sunnyvale, Calif.) before the addition of other reaction components. The final concentration of DMSO in the assay was 0.5%. The HDAC-Glo I/II assay reagent was prepared by rehydration of lyophilized HDAC-Glo I/II substrate in 10 mL. HDAC-Glo I/II assay buffer followed with the addition of 10 μL of developer reagent. 10 uL of 3 nM HDAC8 in the HDAC-Glo I/II assay buffer were first dispensed into the microliter plate containing the compounds and incubated at room temperature for 30 min. The reactions were initiated with the addition of 10 uL HDAC-Glo I/II assay reagent with Multidrop (Thermo, Waltham, Mass.). The final concentration of HDAC8 and HDAC-Glo I/II substrate in the reaction were 1.5 nM and 50 μM, respectively. The assay plate was mixed for 1 min by orbital shaking (500 rpm) and centrifuged for 1 min at 1500 rpm. After 15 min at room temperature, luminescence signals were measured on Top-Count (Perkin Elmer). Wells with no compound served as the positive controls and wells containing no HDAC8 were used as negative controls. IC50 determination was performed by fitting the curve of percentage control activity versus the log of the compound concentration using the GraphPad Prism 6.0 software.

The compounds of the invention were found to be inhibitors of HDAC according to the HDAC8 Enzymatic Assay. Compounds of Formula (I), any subformulas of Formula (I), and all the compounds as described herein have been tested and exhibit an $IC_{50}$ of less than 1 μM.

The compounds of the invention were found to be inhibitors of HDAC8. $IC_{50}$ data is provided below in Table 14. The symbol "+" indicates an $IC_{50} \leq 50$ nM, "++" indicates an $IC_{50}$ more than 50 nM but less than or equal to 200 nM, "+++" indicates an $IC_{50}$ more than 200 nM but less than or equal to 500 nM, and "++++" indicates an $IC_{50}$ more than 500 nM.

TABLE 14

| No. | HDAC8 IC50 (nM) |
|---|---|
| I-0001 | ++ |
| I-0002 | +++ |
| I-0003 | +++ |
| I-0004 | +++ |
| I-0005 | + |
| I-0006 | +++ |
| I-0007 | +++ |
| I-0008 | +++ |
| I-0009 | ++ |
| I-0010 | ++ |
| I-0011 | ++ |
| I-0012 | ++ |
| I-0013 | +++ |
| I-0014 | +++ |
| I-0015 | +++ |
| I-0016 | ++ |
| I-0017 | ++ |
| I-0018 | +++ |
| I-0019 | ++++ |
| I-0020 | +++ |
| I-0021 | ++++ |
| I-0022 | ++++ |

TABLE 14-continued

| No. | HDAC8 IC50 (nM) |
|---|---|
| I-0023 | ++++ |
| I-0024 | ++++ |
| I-0025 | ++ |
| I-0026 | + |
| I-0027 | +++ |
| I-0028 | + |
| I-0029 | ++ |
| I-0030 | + |
| I-0031 | + |
| I-0032 | + |
| I-0033 | ++ |
| I-0034 | +++ |
| I-0035 | +++ |
| I-0036 | ++++ |
| I-0037 | ++++ |
| I-0038 | ++++ |
| I-0039 | ++++ |
| I-0040 | ++++ |
| I-0041 | +++ |
| I-0042 | +++ |
| I-0043 | ++++ |
| I-0044 | ++ |
| I-0045 | ++ |
| I-0046 | +++ |
| I-0047 | +++ |
| I-0048 | ++++ |
| I-0049 | ++++ |
| I-0050 | +++ |
| I-0051 | +++ |
| I-0052 | ++++ |
| I-0053 | +++ |
| I-0054 | ++++ |
| I-0055 | +++ |
| I-0056 | ++++ |
| I-0057 | ++++ |
| I-0058 | +++ |
| I-0059 | ++++ |
| I-0060 | ++++ |
| I-0061 | +++ |
| I-0062 | ++++ |
| I-0063 | +++ |
| I-0064 | ++++ |
| I-0065 | ++++ |
| I-0066 | ++++ |
| I-0067 | ++ |
| I-0068 | +++ |
| I-0069 | ++ |
| I-0070 | ++ |
| I-0071 | ++ |
| I-0072 | +++ |
| I-0073 | +++ |
| I-0074 | ++ |
| I-0075 | +++ |
| I-0076 | ++ |
| I-0077 | ++++ |
| I-0078 | ++++ |
| I-0079 | ++++ |
| I-0080 | ++++ |
| I-0081 | ++ |
| I-0082 | +++ |
| I-0083 | ++ |
| I-0084 | ++++ |
| I-0085 | +++ |
| I-0086 | ++++ |
| I-0087 | ++++ |
| I-0088 | ++++ |
| I-0089 | +++ |
| I-0090 | +++ |
| I-0091 | ++++ |
| I-0092 | +++ |
| I-0093 | + |
| I-0094 | +++ |
| I-0095 | +++ |
| I-0096 | ++++ |
| I-0097 | ++++ |
| I-0098 | ++++ |
| I-0099 | ++++ |
| I-0100 | ++++ |
| I-0101 | ++++ |
| I-0102 | ++++ |
| I-0103 | +++ |
| I-0104 | ++ |
| I-0105 | ++ |
| I-0106 | +++ |
| I-0107 | ++ |
| I-0109 | +++ |
| I-0110 | + |
| I-0111 | ++++ |
| I-0112 | ++ |
| I-0113 | ++++ |
| I-0114 | +++ |
| I-0115 | +++ |
| I-0116 | ++++ |
| I-0117 | ++++ |
| I-0118 | +++ |
| I-0119 | +++ |
| I-0120 | +++ |
| I-0121 | +++ |
| I-0122 | +++ |
| I-0123 | +++ |
| I-0124 | ++ |
| I-0125 | ++ |
| I-0126 | ++ |
| I-0127 | + |
| I-0128 | + |
| I-0129 | +++ |
| I-0130 | ++++ |
| I-0131 | +++ |
| I-0132 | +++ |
| I-0133 | ++++ |
| I-0134 | +++ |
| I-0135 | +++ |
| I-0136 | + |
| I-0137 | + |
| I-0138 | + |
| I-0139 | + |
| I-0140 | + |
| I-0141 | + |
| I-0142 | + |
| I-0143 | ++++ |
| I-0144 | ++ |
| I-0145 | ++++ |
| I-0146 | +++ |
| I-0147 | +++ |
| I-0148 | ++ |
| I-0149 | ++ |
| I-0150 | ++++ |
| I-0151 | ++++ |
| I-0152 | +++ |
| I-0153 | ++ |
| I-0154 | + |
| I-0155 | + |
| I-0156 | + |
| I-0157 | + |
| I-0158 | + |
| I-0159 | + |
| I-0160 | + |
| I-0161 | + |
| I-0162 | +++ |
| I-0163 | ++++ |
| I-0164 | ++++ |
| I-0165 | + |
| I-0166 | + |
| I-0167 | +++ |
| I-0168 | ++++ |
| I-0169 | +++ |
| I-0170 | ++++ |
| I-0171 | +++ |
| I-0172 | +++ |
| I-0173 | ++++ |
| I-0174 | ++++ |
| I-0175 | ++++ |
| I-0176 | ++ |
| I-0177 | + |

TABLE 14-continued

| No. | HDAC8 IC50 (nM) |
|---|---|
| I-0178 | + |
| I-0179 | ++ |
| I-0180 | +++ |
| I-0181 | ++++ |
| I-0182 | ++++ |
| I-0183 | +++ |
| I-0184 | +++ |
| I-0185 | ++++ |
| I-0186 | ++++ |
| I-0187 | ++++ |
| I-0188 | ++++ |
| I-0189 | +++ |
| I-0190 | +++ |
| I-0191 | ++++ |
| I-0192 | ++ |
| I-0193 | ++++ |
| I-0194 | ++++ |
| I-0195 | +++ |
| I-0196 | +++ |
| I-0197 | + |
| I-0198 | + |
| I-0199 | + |
| I-0200 | +++ |
| I-0201 | +++ |
| I-0202 | + |
| I-0203 | ++ |
| I-0204 | ++ |
| I-0205 | ++ |
| I-0206 | + |
| I-0207 | + |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula (I):

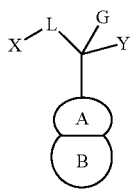

(I)

or a pharmaceutically acceptable salt, a tautomer or a stereoisomer thereof, wherein:

Y is —C(O)NHOH and ring A is fused pyrazolyl, fused imidazolyl or fused triazolyl, each of which is optionally substituted with an $R^1$ substituent;

ring B is fused phenyl, fused pyridyl, fused pyrimidinyl, fused pyrazinyl, fused pyridazinyl, fused triazinyl or fused cyclohexyl, each of which is optionally substituted with 1 to 4 independently selected $R^2$ substituents;

wherein one of the two bridgehead atoms between ring A and ring B is optionally nitrogen;

X is $C_{6-10}$ aryl or 5- to 6-membered heteroaryl, each of which is optionally substituted with from 1-3 independently selected $R^3$ substituents;

L is $C_{1-4}$ alkylene, optionally substituted with from 1-3 $R^q$ substituents independently selected from halo, CN, OH, $C_{1-4}$ alkyl, —$OC_{1-2}$ alkyl, $C_{1-2}$ haloalkyl, and $C_{1-2}$ haloalkoxy; or two $R^q$ substituents attached to the same carbon taken together form $C_{3-6}$ cycloalkyl or 4- to 6-membered heterocycloalkyl, wherein the $C_{3-6}$ cycloalkyl and 4- to 6-membered heterocycloalkyl are each optionally substituted with 1-2 independently selected $R^r$ substituents;

G is H, CN, OH, $C_{1-4}$ alkyl, —$OC_{1-4}$ alkyl, $C_{1-4}$ haloalkyl, or $C_{1-4}$ haloalkoxy, wherein the $C_{1-4}$ alkyl, —$OC_{1-4}$ alkyl, $C_{1-4}$ haloalkyl, or $C_{1-4}$ haloalkoxy of G is optionally substituted with 1-2 substituents independently selected from halo, CN, OH, $NH_2$, $NHR^5$, $NR^5R^5$, —$C(O)NR^5R^5$, $C_{1-4}$ alkyl, —$OC_{1-2}$ alkyl, $C_{1-2}$ haloalkyl and $C_{1-2}$ haloalkoxy, wherein each $R^5$ is independently $C_{1-4}$ alkyl;

each $R^1$ is independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^1$ are each optionally substituted with 1, 2, 3, or 4 $R^b$ substituents independently selected from halo, $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)R^c$ or $S(O)_2NR^cR^c$; wherein $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{14}$ alkyl-, (5-10 membered heteroaryl)-$C_{1-4}$ alkyl-and (4-10 membered heterocycloalkyl)-$C_{1-4}$ alkyl- of $R^b$ are each further optionally substituted with from 1-3 $R^d$ substituents;

each $R^2$ and $R^3$ is independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, —$NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^2$ or $R^3$ are each optionally substituted with 1, 2, 3, or 4 $R^b$ substituents independently selected from halo, $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)$ $NR^cR^c$, $NHR^c$, $NR^cR^c$, $NR^cC(O)R^c$, $NR^cC(O)OR^c$, $NR^cC(O)NR^cR^c$, $NR^cS(O)R$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$; wherein $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_1$-4 alkyl-and (4-10 membered heterocycloalkyl)-$C_1$-4 alkyl- of $R^b$ are each further optionally substituted with from 1-3 $R^d$ substituents;

or two adjacent $R^3$ substituents on the $C_{6-10}$ aryl of X, taken together with the atoms to which they are attached, form fused $C_{3-6}$cycloalkyl, or fused 5- or 6-membered heterocycloalkyl;

or two adjacent $R^3$ substituents on the 5- to 6-membered heteroaryl of X, taken together with the atoms to which they are attached, form fused phenyl, fused $C_{3-6}$ cycloalkyl, fused 5- or 6-membered heteroaryl or fused 5- or 6-membered heterocycloalkyl, wherein the fused 5- or 6-membered heteroaryl or fused 5- or 6-membered heterocycloalkyl has 1-2 heteroatoms as ring members selected from N, O and S; and wherein fused phenyl, fused $C_{3-6}$ cycloalkyl, fused 5- or 6-membered heteroaryl and fused 5- or 6-membered heterocycloalkyl are each optionally substituted with 1 or 2 $R^b$ substituents;

each $R^a$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{14}$ alkyl-, $C_{3-10}$ cycloalkyl-$C_{1-4}$ alkyl-, (5-10 membered heteroaryl)-$C_{14}$ alkyl-, and (4-10 membered heterocycloalkyl)-$C_{1-4}$ alkyl-, wherein the $C_6$ alkyl, $C_{2-6}$ alkenyl, $C_{2-6}$ alkynyl, $C_6$-10 aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of R are each optionally substituted with 1, 2, 3, 4, or 5 $R^d$ substituents independently selected from $C_{1-4}$ alkyl, $C_{1-4}$ haloalkyl, halo, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $—R^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $S(O)R$, $S(O)NR^eR^e$, $S(O)_2R^e$, $NR^eS(O)_2R^e$, $NR^eS(O)_2NR^eR^e$, and $S(O)_2NR^eR^e$, wherein the aliphatic or aromatic portion of $R^d$ is further optionally substituted with 1-3 independently selected R substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 $R^f$ substituents independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 $R^n$ substituents independently selected from $C_{1-4}$ alkyl, $C_{1-4}$ haloalkyl, halo, CN, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR)NR^oR^o$, $NR^oC(=NR)NR^oR^o$, $S(O)R^o$, $S(O)NR^oR^o$, $S(O)_2R^o$, $NR^oS(O)_2R$, $NR^oS(O)_2NR^oR^o$, and $S(O)_2NR^oR^o$;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_6$-10 aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with from 1-3 $R^p$ substituents;

or any two $R^a$ substituents together with the nitrogen atom to which they are attached form a 4-, 5-, 6-, 7-, 8-, 9- or 10-membered heterocycloalkyl group optionally substituted with 1, 2 or 3 $R^h$ substituents independently selected from $C_{1-6}$ alkyl, $C_{3-10}$ cycloalkyl, 4-7 membered heterocycloalkyl, $C_{6-10}$ aryl, 5-6 membered heteroaryl, $C_{1-6}$ haloalkyl, $C_{2-6}$ alkenyl, $C_{2-6}$ alkynyl, halo, CN, $OR^i$, $SR^i$, $NHOR^i$, $C(O)R^i$, $C(O)NR^iR^i$, $C(O)OR^i$, $OC(O)R^i$, $OC(O)NR^iR^i$, $NHR^i$, $NR^iR^i$, $NR^iC(O)R^i$, $NR^iC(O)NR^iR^i$, $NR^iC(O)OR^i$, $C(=NR^i)NR^iR^i$, $NR^iC(=NR^i)NR^iR^i$, $S(O)R^i$, $S(O)NR^iR^i$, $S(O)_2R^i$, $NR'S(O)_2R$, $NR'S(O)_2NR^iR^i$, and $S(O)_2NR^iR^i$, wherein the $C_{1-6}$ alkyl, $C_{3-10}$ cycloalkyl, 4-7 membered heterocycloalkyl, $C_{6-10}$ aryl, and 5-6 membered heteroaryl of $R^h$ are each further optionally substituted by 1, 2, or 3 $R^j$ substituents independently selected from $C_{3-6}$ cycloalkyl, $C_{6-10}$ aryl, 5 or 6-membered heteroaryl, $C_{2-4}$ alkenyl, $C_{2-4}$ alkynyl, halo, $C_{1-4}$ alkyl, $C_{1-4}$ haloalkyl, CN, $NHOR^k$, $OR^k$, $SR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $NR^kC(O)NR^kR^k$, $NR^kC(O)OR^k$, $C(=NR^k)NR^kR^k$, $NR^kC(=NR^k)NR^kR^k$, $S(O)R^k$, $S(O)NR^kR^k$, $S(O)_2R^k$, $NR^kS(O)_2R^k$, $NR^kS(O)_2NR^kR^k$, and $S(O)_2NR^kR^k$;

or two $R^h$ groups attached to the same carbon atom of the 4- to 10-membered heterocycloalkyl taken together with the carbon atom to which they attach form a $C_{3-6}$ cycloalkyl or 4- to 6-membered heterocycloalkyl having 1-2 heteroatoms as ring members selected from O, N or S;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

or any two $R^e$ substituents together with the nitrogen atom to which they are attached form a 4-, 5-, 6-, or 7-membered heterocycloalkyl group optionally substituted with 1, 2, or 3 independently selected $R^h$ substituents;

or any two $R^g$ substituents together with the nitrogen atom to which they are attached form a 4-, 5-, 6-, or 7-membered heterocycloalkyl group optionally substituted with 1, 2, or 3 independently selected $R^h$ substituents;

or any two $R^o$ substituents together with the nitrogen atom to which they are attached form a 4-, 5-, 6-, or 7-membered heterocycloalkyl group optionally substituted with 1, 2, or 3 independently selected $R^h$ substituents; and each $R^e$, $R^i$, $R^k$, $R^o$ or $R^p$ is independently selected from H, $C_{1-4}$ alkyl, $C_{3-6}$ cycloalkyl, $C_{6-10}$ aryl, 5 or 6-membered heteroaryl, $C_{1-4}$ haloalkyl, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, $C_{2-4}$ alkenyl, and $C_{2-4}$ alkynyl of $R^e$, $R^i$, $R^k$, $R^o$ or $R^p$ are each optionally substituted with 1, 2 or 3 $R^r$ substituents independently selected from OH, CN, amino, halo, $C_{1-4}$ alkyl, $C_{1-4}$ alkoxy, $C_{1-4}$ alkylthio, $NHR^6$, $NR^6R^6$, $C_{1-4}$ haloalkyl, and $C_{1-4}$ haloalkoxy, wherein each $R^6$ is independently H or $C_{1-6}$ alkyl.

2. The compound of claim 1, or a pharmaceutically acceptable salt, a tautomer or a stereoisomer thereof, wherein the moiety:

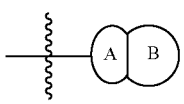

in formula (I) is selected from:

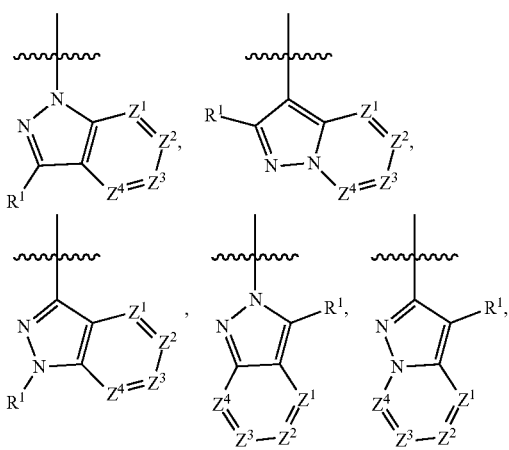

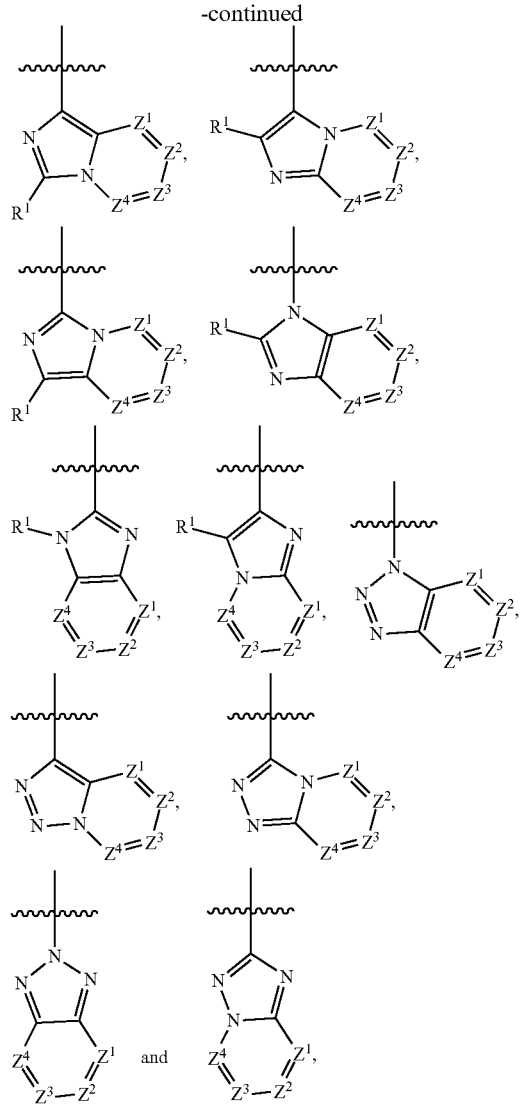

wherein $Z^1$, $Z^2$, $Z^3$ and $Z^4$ are each independently N or $CR^2$ with the proviso that at least two of $Z^1$, $Z^2$, $Z^3$ and $Z^4$ are $CR^2$ and the wavy line indicates the point of attachment to the rest of the molecule.

3. The compound of claim 2, or a pharmaceutically acceptable salt, a tautomer or a stereoisomer thereof, wherein $Z^1$, $Z^2$, $Z^3$ and $Z^4$ are each independently $CR^2$.

4. The compound of claim 2, or a pharmaceutically acceptable salt, a tautomer or a stereoisomer thereof, wherein one or two of $Z^1$, $Z^2$, $Z^3$ and $Z^4$ are N and the others are each independently $CR^2$.

5. The compound of claim 1, or a pharmaceutically acceptable salt, a tautomer or a stereoisomer thereof, wherein ring B is fused cyclohexyl optionally substituted with 1-4 independently selected $R^2$ substituents.

6. The compound of claim 1, or a pharmaceutically acceptable salt, a tautomer or a stereoisomer thereof, wherein X is $C_{6-10}$ aryl, optionally substituted with 1-3 independently selected $R^3$ substituents.

7. The compound of claim 1, or a pharmaceutically acceptable salt, a tautomer or a stereoisomer thereof, wherein X is phenyl, optionally substituted with 1-3 independently selected $R^3$ substituents.

8. The compound of claim 1, or a pharmaceutically acceptable salt, a tautomer or a stereoisomer thereof, wherein L is $CH_2$, optionally substituted with 1-3 independently selected $R^q$ substituents.

9. The compound of claim 1, or a pharmaceutically acceptable salt, a tautomer or a stereoisomer thereof, wherein L is $CH_2$.

10. The compound of claim 1, or a pharmaceutically acceptable salt, a tautomer or a stereoisomer thereof, wherein G is H.

11. The compound of claim 1, or a pharmaceutically acceptable salt, a tautomer or a stereoisomer thereof, wherein Y is —C(O)NHOH.

12. The compound of claim 1, or a pharmaceutically acceptable salt, a tautomer or a stereoisomer thereof, wherein $R^1$ is H, halo or $C_{2-6}$ alkynyl, wherein the $C_{2-6}$ alkynyl is optionally substituted with $C_{3-6}$ cycloalkyl, 4 to 6-membered heterocycloalkyl, phenyl or 5- or 6-membered heteroaryl, each of which is optionally substituted with 1-3 independently selected $R^b$ substituents.

13. The compound of claim 1, or a pharmaceutically acceptable salt, a tautomer or a stereoisomer thereof, wherein $R^1$ is H, halo, or 2-cyclopropylethynyl optionally substituted with 1-3 independently selected $R^b$ substituents.

14. The compound of claim 1, or a pharmaceutically acceptable salt, a tautomer or a stereoisomer thereof, wherein $R^2$ is H, halo, $C_{1-6}$ alkyl, phenyl, 5- or 6-membered heteroaryl, $C_{3-6}$ cycloalkyl, 4 to 6-membered heterocycloalkyl, 4 to 6-membered heterocycloalkyl-$C_{1-4}$alkyl, 5- or 6-membered heteroaryl-$C_{1-4}$alkyl, $C_{3-6}$cycloalkyl-$C_{1-4}$alkyl, —C(O)$R^a$, —C(O)NH$R^a$ or —O$R^a$, wherein each $R^a$ is independently selected from $C_{1-6}$ alkyl, 4 to 6-membered heterocycloalkyl, 4 to 6-membered heterocycloalkyl-$C_{1-4}$alkyl, $C_{3-6}$ cycloalkyl, $C_{3-6}$ cycloalkyl-$C_{1-4}$ alkyl, 5- to 10-membered heteroaryl and 5- to 10-membered heteroaryl-$C_{1-4}$alkyl, each of which is optionally substituted with 1-3 independently selected $R^d$ substituents; and wherein $C_{1-6}$ alkyl, phenyl, 5- or 6-membered heteroaryl, $C_{3-6}$ cycloalkyl, 4 to 6-membered heterocycloalkyl, 4 to 6-membered heterocycloalkyl-$C_{1-4}$ alkyl, 5- or 6-membered heteroaryl-$C_{1-4}$ alkyl, and $C_{3-6}$ cycloalkyl-$C_{1-4}$ alkyl of $R^2$ are each optionally substituted with 1-3 independently selected $R^b$ groups.

15. The compound of claim 14, or a pharmaceutically acceptable salt, a tautomer or a stereoisomer thereof, wherein said $C_{1-6}$ alkyl, phenyl, 5- or 6-membered heteroaryl, $C_{3-6}$ cycloalkyl, 4 to 6-membered heterocycloalkyl, 4 to 6-membered heterocycloalkyl-$C_{1-4}$ alkyl, 5- or 6-membered heteroaryl-$C_{1-4}$ alkyl, and $C_{3-6}$ cycloalkyl-$C_{1-4}$ alkyl of $R^2$ are each optionally substituted with 1-3 independently selected $R^b$ groups selected from halo, CN, $C_{1-6}$ alkyl, —O$R^c$, —C(O)N$R^cR^c$, $R^e$O—$C_{1-6}$alkyl-, NH$R^c$ or 4- to 10-membered heterocycloalkyl optionally substituted with 1-2 independently selected $R^d$ substituents.

16. The compound of claim 1, or a pharmaceutically acceptable salt, a tautomer or a stereoisomer thereof, wherein $R^2$ is H, F, Cl, Br, I, $C_{1-4}$ alkyl, phenyl, 2-pyridyl, 3-pyridyl, 4-pyridyl, 5-pyrimidinyl, 2-pyrimidinyl, 4-pyrimidinyl, 1-pyrazolyl, 3-pyrazolyl, 4-pyrazolyl, 1-piperidinyl, 4-piperidinyl, 4-morpholinyl, 1-piperazinyl, 2-tetrahydrofuranyl, 3-tetrahydrofuranyl, 2-tetrahydro-2H-pyranyl, 3-tetrahydropyranyl, 4-tetrahydropyranyl, 7-azaspiro[3.5]nonan-7-yl, 2-oxa-7-azaspiro[3.5]nonan-7-yl, 8-azaspiro[4.5]decan-8-yl, 3-azaspiro[5.5]undecan-3-yl, 3-oxa-9-azaspiro[5.5]undecan-9-yl, cyclopropyl, cyclobutyl, cyclopentyl, cyclohexyl, —C(O)$R^a$, —C(O)NH$R^a$, or —$CH_2R^b$, wherein $R^a$ and $R^b$ are each independently selected from 1-piperidinyl, 4-piperidinyl, 4-morpholinyl, 1-piperazinyl, 2-tetrahydrofuranyl, 3-tetrahydrofuranyl, 2-tetrahydropyranyl, 3-tetrahydropyranyl, 4-tetrahydropyranyl, 7-azaspiro[3.5]nonan-7-yl, 2-oxa-7-azaspiro[3.5]nonan-7-yl, 8-azaspiro[4.5]decan-8-yl, 3-azaspiro[5.5]undecan-3-yl, 3-oxa-9-azaspiro[5.5]undecan-9-yl, cyclopropyl, cyclobutyl, cyclopentyl, cyclohexyl, cyclopropyl-$C_{1-2}$alkyl, cyclobutyl-$C_{1-2}$alkyl, cyclopentyl-$C_{1-2}$alkyl, cyclohexyl-$C_{1-12}$alkyl, 4-morpholinyl-$C_{1-12}$alkyl, and 4-tetrahydropyranyl-$C_{1-2}$alkyl.

17. The compound of claim 1, or a pharmaceutically acceptable salt, a tautomer or a stereoisomer thereof, wherein $R^3$ is selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, C(O)$R^a$, C(O)N$R^aR^a$, C(O)O$R^a$, OC(O)$R^a$, OC(O)N$R^aR^a$, NH$R^a$, N$R^aR^a$, $NR^aC(O)R^a$, $NR^a$-C(O)O$R^a$, $NR^aC(O)NR^aR^a$, C(=N$R^a$)$R^a$, C(=N$R^a$)N$R^aR^a$, $NR^aC(=NR^a)NR^aR^a$, $NR^aS(O)R^a$, $NR^aS(O)_2R^a$, $NR^aS(O)_2NR^aR^a$, S(O)$R^a$, S(O)N$R^aR^a$, S(O)$_2R^a$, and S(O)$_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^3$ are each optionally substituted with 1, 2, 3, or 4 $R^b$ substituents independently selected from halo, $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NH_2$, $NO_2$, NHO$R^c$, O$R^c$, S$R^c$, C(O)$R^c$, C(O)N$R^cR^c$, C(O)O$R^c$, OC(O)$R^c$, OC(O)N$R^cR^c$, C(=N$R^c$)N$R^cR^c$, $NR^cC(=NR^c)NR^cR^c$, NH$R^c$, N$R^cR^c$, $NR^cC(O)R^c$, $NR^cC(O)OR$, $NR^cC(O)NR^cR^c$, $NR^cS(O)R^c$, $NR^cS(O)_2R^c$ $NR^cS(O)_2NR^cR^c$, S(O)$R^c$, S(O)N$R^cR^c$, S(O)$_2R^c$ or S(O)$_2NR^iR^i$; wherein $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-and (4-10 membered heterocycloalkyl)-$C_{1-4}$ alkyl- of $R^b$ are each further optionally substituted with from 1-3 $R^d$ substituents.

18. The compound of claim 1, or a pharmaceutically acceptable salt, a tautomer or a stereoisomer thereof, wherein $R^3$ is H.

19. The compound of claim 1, having Formula (II):

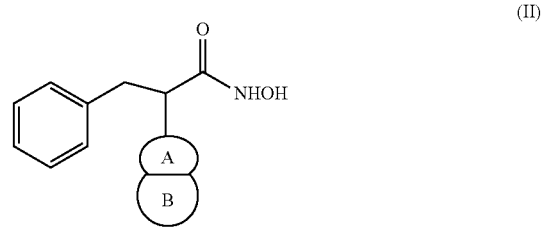

(II)

or a pharmaceutically acceptable salt, a tautomer or a stereoisomer thereof.

20. The compound of claim 19, or a pharmaceutically acceptable salt, a tautomer or a stereoisomer thereof, wherein the moiety:

is:

<image: structure with rings A and B>

<image: six pyrazole/imidazole fused ring structures with Z¹, Z², Z³, Z⁴ positions and R¹ substituents> wherein Z¹, Z², Z³ and Z⁴ are each independently N or CR² with the proviso that at least two of Z¹, Z², Z³ and Z⁴ are CR² and the wavy line indicates the point of attachment to the rest of the molecule.

21. The compound of claim 19, or a pharmaceutically acceptable salt, a tautomer or a stereoisomer thereof, wherein the moiety:

<image: structure with rings A and B> is:

<image: four fused bicyclic structures with R¹ and (R²)ₘ substituents>

<image: additional fused bicyclic structure with R¹ and (R²)ₘ> wherein the subscript m is 1, 2, 3 or 4 and the wavy line indicates the point of attachment to the rest of the molecule.

22. The compound of claim 1, wherein the compound is selected from:
- 2-(5-Chloro-1H-indazol-1-yl)-N-hydroxy-3-phenylpropanamide,
- N-hydroxy-2-(2H-indazol-2-yl)-3-phenylpropanamide,
- 2-(5-Chloro-2H-indazol-2-yl)-N-hydroxy-3-phenylpropanamide,
- 2-(6-bromo-2H-indazol-2-yl)-N-hydroxy-3-phenylpropanamide,
- 2-[5-Chloro-3-(cyclopropylethynyl)-2H-indazol-2-yl]-N-hydroxy-3-phenylpropanamide,
- N-hydroxy-3-phenyl-2-(6-phenyl-2H-indazol-2-yl)propanamide,
- N-hydroxy-3-phenyl-2-(6-(pyrimidin-5-yl)-2H-indazol-2-yl)propanamide,
- N-hydroxy-3-phenyl-2-(6-(pyridin-3-yl)-2H-indazol-2-yl)propanamide,
- 2-(5-chloro-3-(cyclopropylethynyl)-1H-indazol-1-yl)-N-hydroxy-3-phenylpropanamide,
- N-hydroxy-2-(5-(1-methyl-1H-pyrazol-5-yl)-1H-indazol-1-yl)-3-phenylpropanamide,
- N-hydroxy-3-phenyl-2-(5-pyridin-4-yl-1H-indazol-1-yl)propanamide,
- N-hydroxy-3-phenyl-2-(5-(pyrimidin-5-yl)-1H-indazol-1-yl)propanamide,
- N-hydroxy-3-phenyl-2-(5-phenyl-1H-indazol-1-yl)propanamide,
- 2-(5-(2,6-difluorophenyl)-1H-indazol-1-yl)-N-hydroxy-3-phenylpropanamide,
- 2-(5-(4-cyanophenyl)-1H-indazol-1-yl)-N-hydroxy-3-phenylpropanamide,
- N-hydroxy-2-(5-methyl-1H-indazol-1-yl)-3-phenylpropanamide,
- 2-(5-bromo-1H-indazol-1-yl)-N-hydroxy-3-phenylpropanamide,
- 2-(6-Ethyl-1H-indazol-1-yl)-N-hydroxy-3-phenylpropanamide,
- 2-(5-cyclopropyl-1H-indazol-1-yl)-N-hydroxy-3-phenylpropanamide,
- 2-(5-ethyl-1H-indazol-1-yl)-N-hydroxy-3-phenylpropanamide,
- 2-(6-bromo-1H-indazol-1-yl)-N-hydroxy-3-phenylpropanamide,
- N-hydroxy-3-phenyl-2-(6-phenyl-1H-indazol-1-yl)propanamide,
- N-hydroxy-3-phenyl-2-(6-(pyrimidin-5-yl)-1H-indazol-1-yl)propanamide,
- 2-(5-bromo-2H-indazol-2-yl)-N-hydroxy-3-phenylpropanamide,
- 2-[3-(Cyclopropylethynyl)-5-phenyl-2H-indazol-2-yl]-N-hydroxy-3-phenylpropanamide,
- 4-(3-(cyclopropylethynyl)-2-(1-(hydroxyamino)-1-oxo-3-phenylpropan-2-yl)-2H-indazol-5-yl)benzamide,
- 2-(3-(cyclopropylethynyl)-5-(2,6-difluorophenyl)-2H-indazol-2-yl)-N-hydroxy-3-phenylpropanamide, 2-(3-(cyclopropylethynyl)-5-(1-methyl-1H-pyrazol-5-yl)-2H-indazol-2-yl)-N-hydroxy-3-phenylpropanamide,
2-(3-(cyclopropylethynyl)-5-(pyridin-4-yl)-2H-indazol-2-yl)-N-hydroxy-3-phenylpropanamide,
2-(3-(cyclopropylethynyl)-5-(pyrimidin-5-yl)-2H-indazol-2-yl)-N-hydroxy-3-phenylpropanamide,
2-(3-(cyclopropylethynyl)-5-(2-methoxypyrimidin-5-yl)-2H-indazol-2-yl)-N-hydroxy-3-phenylpropanamide,
2-(3-(cyclopropylethynyl)-5-methyl-2H-indazol-2-yl)-N-hydroxy-3-phenylpropanamide,
(Z)—N-hydroxy-2-(5-(4-(N'-hydroxycarbamimidoyl)phenyl)-2H-indazol-2-yl)-3-phenylpropanamide,
N-hydroxy-2-(5-(1-methyl-1H-pyrazol-5-yl)-2H-indazol-2-yl)-3-phenylpropanamide,
N-hydroxy-2-(5-(2-methoxypyrimidin-5-yl)-2H-indazol-2-yl)-3-phenylpropanamide,
N-hydroxy-3-phenyl-2-(5-phenyl-2H-indazol-2-yl)propanamide,
2-(6-fluoro-2H-indazol-2-yl)-N-hydroxy-3-phenylpropanamide,
N-hydroxy-3-phenyl-2-(6-(trifluoromethyl)-2H-indazol-2-yl)propanamide,
2-(6-bromo-5-methyl-2H-indazol-2-yl)-N-hydroxy-3-phenylpropanamide,
N-hydroxy-2-(6-methyl-2H-indazol-2-yl)-3-phenylpropanamide,
2-(1H-benzo[d]imidazol-1-yl)-N-hydroxy-3-phenylpropanamide,
N-hydroxy-3-phenyl-2-(1H-pyrazolo[4,3-c]pyridin-1-yl)propanamide,
N-hydroxy-3-phenyl-2-(2H-pyrazolo [4, 3-c]pyridin-2-yl)propanamide,
2-(3-(cyclopropylethynyl)-5-(1-methyl-1H-pyrazol-4-yl)-2H-indazol-2-yl)-N-hydroxy-3-phenylpropanamide,
2-(3-(cyclopropylethynyl)-5-(pyridin-3-yl)-2H-indazol-2-yl)-N-hydroxy-3-phenylpropanamide,
2-(3-(cyclopropylethynyl)-5-(6-methoxypyridin-3-yl)-2H-indazol-2-yl)-N-hydroxy-3-phenylpropanamide,
N-hydroxy-2-(6-(1-methyl-1H-pyrazol-5-yl)-2H-indazol-2-yl)-3-phenylpropanamide,
N-hydroxy-2-(6-(1-methylpiperidin-4-yl)-2H-indazol-2-yl)-3-phenylpropanamide,
N-hydroxy-2-(5-methyl-2H-indazol-2-yl)-3-phenylpropanamide,
N-hydroxy-3-phenyl-2-(5-(pyridin-4-yl)-2H-indazol-2-yl)propanamide,
N-hydroxy-3-phenyl-2-(5-(pyrimidin-5-yl)-2H-indazol-2-yl)propanamide,
N-hydroxy-3-phenyl-2-(6-(piperidin-1-yl)-2H-indazol-2-yl)propanamide,
2-(7-(cyclopropylethynyl)-2H-pyrazolo[4,3-c]pyridin-2-yl)-N-hydroxy-3-phenylpropanamide,
N-hydroxy-2-(7-iodo-2H-pyrazolo[4,3-c]pyridin-2-yl)-3-phenylpropanamide,
2-(4-chloro-1H-pyrazolo[4,3-c]pyridin-1-yl)-N-hydroxy-3-phenylpropanamide,
2-(4-chloro-2H-pyrazolo[4,3-c]pyridin-2-yl)-N-hydroxy-3-phenylpropanamide,
N-hydroxy-2-(4-(1-methyl-1,2,3,6-tetrahydropyridin-4-yl)-2H-indazol-2-yl)-3-phenylpropanamide,
N-hydroxy-3-phenyl-2-(4-(pyridin-4-yl)-2H-indazol-2-yl)propanamide,
N-hydroxy-2-(4-morpholino-2H-indazol-2-yl)-3-phenylpropanamide,
N-hydroxy-3-phenyl-2-(4-phenyl-2H-indazol-2-yl)propanamide,
N-hydroxy-2-(4-(1-methyl-1H-pyrazol-5-yl)-2H-indazol-2-yl)-3-phenylpropanamide,
2-(4-cyclopropyl-2H-indazol-2-yl)-N-hydroxy-3-phenylpropanamide,
N-hydroxy-3-phenyl-2-(4-(pyrimidin-5-yl)-2H-indazol-2-yl)propanamide,
N-hydroxy-2-(4-methyl-2H-indazol-2-yl)-3-phenylpropanamide,
N-hydroxy-2-(4-(1-methylpiperidin-4-yl)-2H-indazol-2-yl)-3-phenylpropanamide,
N-hydroxy-3-phenyl-2-(7-phenyl-2H-indazol-2-yl)propanamide,
N-hydroxy-2-(7-(1-methyl-1H-pyrazol-5-yl)-2H-indazol-2-yl)-3-phenylpropanamide,
2-(7-bromo-2H-indazol-2-yl)-N-hydroxy-3-phenylpropanamide,
N-hydroxy-2-(4-(1-methyl-1H-pyrazol-5-yl)-1H-pyrazolo[4,3-c]pyridin-1-yl)-3-phenylpropanamide,
N-hydroxy-3-phenyl-2-(4-(pyridin-4-yl)-1H-pyrazolo[4,3-c]pyridin-1-yl)propanamide,
N-hydroxy-3-phenyl-2-(4-(pyrimidin-5-yl)-1H-pyrazolo[4,3-c]pyridin-1-yl)propanamide,
N-hydroxy-2-(5-(1-methyl-1H-pyrazol-5-yl)-1H-pyrazolo[4,3-b]pyridin-1-yl)-3-phenylpropanamide,
N-hydroxy-3-phenyl-2-(5-(pyridin-4-yl)-1H-pyrazolo[4,3-b]pyridin-1-yl)propanamide,
N-hydroxy-3-phenyl-2-(5-(pyrimidin-5-yl)-1H-pyrazolo[4,3-b]pyridin-1-yl)propanamide,
N-hydroxy-2-(5-methyl-1H-pyrazolo[4,3-b]pyridin-1-yl)-3-phenylpropanamide,
2-(5-chloro-1H-pyrazolo[4,3-b]pyridin-1-yl)-N-hydroxy-3-phenylpropanamide,
2-(5-chloro-2H-pyrazolo[4,3-b]pyridin-2-yl)-N-hydroxy-3-phenylpropanamide,
N-hydroxy-2-(7-methyl-2H-indazol-2-yl)-3-phenylpropanamide,
N-hydroxy-3-phenyl-2-(4-phenyl-1H-indazol-1-yl)propanamide,
4-(1-(1-(hydroxyamino)-1-oxo-3-phenylpropan-2-yl)-1H-indazol-4-yl)benzamide,
N-hydroxy-3-phenyl-2-(4-(pyrimidin-5-yl)-1H-indazol-1-yl)propanamide,
2-(7-(Cyclopropylethynyl)-2H-indazol-2-yl)-N-hydroxy-3-phenylpropanamide,
N-hydroxy-2-(4-(1-methyl-1H-pyrazol-5-yl)-1H-indazol-1-yl)-3-phenylpropanamide,
N-hydroxy-2-(4-methyl-1H-indazol-1-yl)-3-phenylpropanamide,
N-hydroxy-2-(4-(1-methyl-1,2,3,6-tetrahydropyridin-4-yl)-1H-indazol-1-yl)-3-phenylpropanamide,
N-hydroxy-3-phenyl-2-(5-phenyl-1H-pyrazolo [3, 4-c]pyridin-1-yl)propanamide,
2-(5-(2,6-difluorophenyl)-1H-pyrazolo[3,4-c]pyridin-1-yl)-N-hydroxy-3-phenylpropanamide,
2-(5-(4-cyanophenyl)-1H-pyrazolo[3,4-c]pyridin-1-yl)-N-hydroxy-3-phenylpropanamide,
4-(1-(1-(hydroxyamino)-1-oxo-3-phenylpropan-2-yl)-1H-pyrazolo[3,4-c]pyridin-5-yl)benzamide,
N-hydroxy-2-(5-(1-methyl-1H-pyrazol-5-yl)-1H-pyrazolo [3,4-c]pyridin-1-yl)-3-phenylpropanamide,
N-hydroxy-2-(5-(1-methyl-1H-pyrazol-4-yl)-1H-pyrazolo [3,4-c]pyridin-1-yl)-3-phenylpropanamide,
N-hydroxy-3-phenyl-2-(5-(pyrimidin-5-yl)-1H-pyrazolo[3,4-c]pyridin-1-yl)propanamide, 2-(7-Chloroimidazo[1,2-a]pyridin-3-yl)-N-hydroxy-3-phenylpropanamide,
N-hydroxy-2-(5-(2-methoxypyrimidin-5-yl)-1H-pyrazolo[3,4-c]pyridin-1-yl)-3-phenylpropanamide,
N-hydroxy-3-phenyl-2-(5-(pyridin-3-yl)-1H-pyrazolo[3,4-c]pyridin-1-yl)propanamide,
N-hydroxy-2-(5-(6-methoxypyridin-3-yl)-1H-pyrazolo[3,4-c]pyridin-1-yl)-3-phenylpropanamide,
N-hydroxy-3-phenyl-2-(5-(pyridin-4-yl)-1H-pyrazolo[3,4-c]pyridin-1-yl)propanamide,
2-(5-cyclopropyl-6H-pyrazolo[3,4-c]pyridin-1-yl)-N-hydroxy-3-phenylpropanamide,
2-(5-bromo-1H-pyrazolo[3,4-c]pyridin-1-yl)-N-hydroxy-3-phenylpropanamide,
2-(5-bromo-2H-pyrazolo[3,4-c]pyridine-2-yl)-N-hydroxy-3-phenylpropanamide,
N-hydroxy-2-(7-(1-methyl-1,2,3,6-tetrahydropyridin-4-yl)-2H-indazol-2-yl)-3-phenylpropanamide,
N-hydroxy-2-(1H-indazol-1-yl)-3-phenylpropanamide,
N-hydroxy-3-phenyl-2-(5-(1,3,5-trimethyl-1H-pyrazol-4-yl)-1H-indazol-1-yl)propanamide,
N-hydroxy-3-phenyl-2-(5-(pyridin-3-yl)-1H-indazol-1-yl)propanamide,
N-hydroxy-2-(5-(1-methyl-1H-pyrazol-4-yl)-1H-indazol-1-yl)-3-phenylpropanamide,
4-(1-(1-(hydroxyamino)-1-oxo-3-phenylpropan-2-yl)-1H-indazol-5-yl)-N,N-dimethylbenzamide,
(Z)—N-hydroxy-2-(5-(3-(N'-hydroxycarbamimidoyl)phenyl)-1H-indazol-1-yl)-3-phenylpropanamide,
N-hydroxy-2-(7-(1-methyl-1H-pyrazol-4-yl)-2H-indazol-2-yl)-3-phenylpropanamide,
4-(2-(1-(hydroxyamino)-1-oxo-3-phenylpropan-2-yl)-2H-indazol-7-yl)-N,N-dimethylbenzamide,
N-hydroxy-3-phenyl-2-(7-(1,3,5-trimethyl-1H-pyrazol-4-yl)-2H-indazol-2-yl)propanamide,
N-hydroxy-3-phenyl-2-(7-(pyrimidin-5-yl)imidazo[1,2-a]pyridin-3-yl)propanamide,
N-hydroxy-3-phenyl-2-(7-(pyridin-4-yl)imidazo[1,2-a]pyridin-3-yl)propanamide,
N-hydroxy-3-phenyl-2-(7-(pyridin-3-yl)imidazo[1,2-a]pyridin-3-yl)propanamide,
N-hydroxy-2-(7-(1-methyl-1H-pyrazol-5-yl)imidazo[1,2-a]pyridin-3-yl)-3-phenylpropanamide,
N-hydroxy-3-phenyl-2-(5-phenyl-1H-pyrazolo[3,4-b]pyridin-1-yl)propanamide,
2-(5-(4-cyanophenyl)-1H-pyrazolo[3,4-b]pyridin-1-yl)-N-hydroxy-3-phenylpropanamide,
4-(1-(1-(hydroxyamino)-1-oxo-3-phenylpropan-2-yl)-1H-pyrazolo[3,4-b]pyridin-5-yl)benzamide,
N-hydroxy-2-(5-(1-methyl-1H-pyrazol-5-yl)-1H-pyrazolo[3,4-b]pyridin-1-yl)-3-phenylpropanamide,
N-hydroxy-2-(5-(1-methyl-1H-pyrazol-4-yl)-1H-pyrazolo[3,4-b]pyridin-1-yl)-3-phenylpropanamide,
N-hydroxy-32-(5-(1-phenyl-2-(5-(pyrimidin-5-yl)-1H-pyrazolo[3,4-b]pyridin-1-yl)propanamide,
2-(5-bromo-1H-pyrazolo[3,4-b]pyridin-1-yl)-N-hydroxy-3-phenylpropanamide,
2-(5-bromo-2H-pyrazolo[3,4-b]pyridin-2-yl)-N-hydroxy-3-phenylpropanamide,
2-(7-chloro-3-iodo-2H-pyrazolo[3,4-c]pyridin-2-yl-N-hydroxy-3-phenylpropanamide,
2-(7-chloro-3-iodo-2H-pyrazolo[3,4-c]pyridin-2-yl)-N-hydroxy-3-phenylpropanamide,
2-[7-Chloro-3-(cyclopropylethynyl)-1H-pyrazolo[3,4-c]pyridin-1-yl]-N-hydroxy-3-phenylpropanamide,
2-[7-Chloro-3-(cyclopropylethynyl)-2H-pyrazolo [3,4-c]pyridin-2-yl]-N-hydroxy-3-phenylpropanamide,
2-[3-(Cyclopropylethynyl)-7-(1-methyl-1H-pyrazol-5-yl)-2H-pyrazolo [3,4-c]pyridin-2-yl]-N-hydroxy-3-phenylpropanamide,
2-(7-chloro-2H-pyrazolo[3,4-c]pyridin-2-yl)-N-hydroxy-3-phenylpropanamide,
2-(5-(3-cyanophenyl)-1H-pyrazolo[3,4-b]pyridin-1-yl)-N-hydroxy-3-phenylpropanamide,
3-(1-(1-(hydroxyamino)-1-oxo-3-phenylpropan-2-yl)-1H-pyrazolo[3,4-b]pyridin-5-yl)benzamide,
N-hydroxy-3-phenyl-2-(5-(pyridin-3-yl)-1H-pyrazolo[3,4-b]pyridin-1-yl)propanamide,
N-hydroxy-3-phenyl-2-(5-(pyridin-4-yl)-1H-pyrazolo[3,4-b]pyridin-1-yl)propanamide,
2-(8-Chloroimidazo[1,2-a]pyridin-3-yl)-N-hydroxy-3-phenylpropanamide,
2-(7-chloro-3-iodo-2H-indazol-2-yl)-N-hydroxy-3-phenylpropanamide,
2-(7-chloro-3-(cyclopropylethynyl)-2H-indazol-2-yl)-N-hydroxy-3-phenylpropanamide,
2-(3-(cyclopropylethynyl)-7-(1-methyl-1H-pyrazol-5-yl)-2H-indazol-2-yl)-N-hydroxy-3-phenylpropanamide,
4-(3-(cyclopropylethynyl)-2-(1-(hydroxyamino)-1-oxo-3-phenylpropan-2-yl)-2H-indazol-7-yl)benzamide,
4-(3-(cyclopropylethynyl)-2-(1-(hydroxyamino)-1-oxo-3-phenylpropan-2-yl)-2H-indazol-7-yl)-N,N-dimethylbenzamide,
4-(3-(cyclopropylethynyl)-2-(1-(hydroxyamino)-1-oxo-3-phenylpropan-2-yl)-2H-pyrazolo[3,4-c]pyridin-7-yl)benzamide,
4-(3-(cyclopropylethynyl)-2-(1-(hydroxyamino)-1-oxo-3-phenylpropan-2-yl)-2H-pyrazolo[3,4-c]pyridin-7-yl)-N-methylbenzamide,
4-(3-(cyclopropylethynyl)-2-(1-(hydroxyamino)-1-oxo-3-phenylpropan-2-yl)-2H-pyrazolo[3,4-c]pyridin-7-yl)-N,N-dimethylbenzamide,
N-hydroxy-2-(6-(1-(2-morpholinoethyl)-1H-pyrazol-4-yl)-1H-indazol-1-yl)-3-phenylpropanamide,
2-(6-(5-(4-acetylpiperazin-1-yl)pyridin-3-yl)-1H-indazol-1-yl)-N-hydroxy-3-phenylpropanamide,
N-hydroxy-2-(4-(4-methylpiperidin-1-yl)-2H-indazol-2-yl)-3-phenylpropanamide,
N-hydroxy-2-(4-(6-isopropoxypyridin-3-yl)-2H-indazol-2-yl)-3-phenylpropanamide,
N-hydroxy-2-(4-(4-(methoxymethyl)phenyl)-2H-indazol-2-yl)-3-phenylpropanamide,
N-hydroxy-2-(4-(4-(4-methylpiperazin-1-yl)phenyl)-2H-indazol-2-yl)-3-phenylpropanamide,
N-hydroxy-2-(4-(6-(4-methylpiperazin-1-yl)pyridin-3-yl)-2H-indazol-2-yl)-3-phenylpropanamide,
N-hydroxy-2-(7-(4-(methoxymethyl)phenyl)imidazo[1,2-a]pyridin-3-yl)-3-phenylpropanamide,
N-hydroxy-2-(7-(4-(4-methylpiperazin-1-yl)phenyl)imidazo[1,2-a]pyridin-3-yl)-3-phenylpropanamide,
N-hydroxy-2-(7-(6-(4-methylpiperazin-1-yl)pyridin-3-yl)imidazo[1,2-a]pyridin-3-yl)-3-phenylpropanamide,
N-hydroxy-3-phenyl-2-(5-(4-(pyrrolidin-1-yl)cyclohexyl)-1H-indazol-1-yl)propanamide,
2-(3-(cyclopropylethynyl)-7-(pyridin-4-yl)-2H-indazol-2-yl)-N-hydroxy-3-phenylpropanamide,
2-(3-(cyclopropylethynyl)-7-(pyridin-3-yl)-2H-indazol-2-yl)-N-hydroxy-3-phenylpropanamide,
2-(3-(cyclopropylethynyl)-7-(pyrimidin-5-yl)-2H-indazol-2-yl)-N-hydroxy-3-phenylpropanamide,
3-(3-(cyclopropylethynyl)-2-(1-(hydroxyamino)-1-oxo-3-phenylpropan-2-yl)-2H-indazol-7-yl)benzamide, 3-(3-(cyclopropylethynyl)-2-(1-(hydroxyamino)-1-oxo-3-phenylpropan-2-yl)-2H-indazol-7-yl)-N-methylbenzamide, 3-(3-(cyclopropylethynyl)-2-(1-(hydroxyamino)-1-oxo-3-phenylpropan-2-yl)-2H-indazol-7-yl)-N,N-dimethylbenzamide, 2-(7-cyclopropyl-3-(cyclopropylethynyl)-2H-indazol-2-yl)-N-hydroxy-3-phenylpropanamide, 2-(3-(cyclopropylethynyl)-7-methyl-2H-indazol-2-yl)-N-hydroxy-3-phenylpropanamide, N-hydroxy-3-phenyl-2-(8-(pyridin-4-yl)imidazo [1,2-a]pyridin-3-yl)propanamide, N-hydroxy-3-phenyl-2-(8-(pyridin-3-yl)imidazo [1,2-a]pyridin-3-yl)propanamide, N-hydroxy-3-phenyl-2-(8-pyrimidin-5-ylimidazo[1,2-a]pyridin-3-yl)propanamide, 2-(3-(cyclopropylethynyl)-7-(1-(2-methoxyethyl)-3-methyl-1H-pyrazol-4-yl)-2H-indazol-2-yl)-N-hydroxy-3-phenylpropanamide, 2-(3-(cyclopropylethynyl)-7-(3-methyl-1H-pyrazol-4-yl)-2H-indazol-2-yl)-N-hydroxy-3-phenylpropanamide, 4-(3-(1-(hydroxyamino)-1-oxo-3-phenylpropan-2-yl)imidazo[1,2-a]pyridin-8-yl)benzamide, 4-(3-(1-(hydroxyamino)-1-oxo-3-phenylpropan-2-yl)imidazo[1,2-a]pyridin-8-yl)-N,N-dimethylbenzamide, 3-(3-(1-(hydroxyamino)-1-oxo-3-phenylpropan-2-yl)imidazo[1,2-a]pyridin-8-yl)benzamide, 2-(8-cyclopropylimidazo[1,2-a]pyridin-3-yl)-N-hydroxy-3-phenylpropanamide, N-hydroxy-2-(8-methylimidazo[1,2-a]pyridin-3-yl)-3-phenylpropanamide, methyl 2-(7-(4,4-difluoropiperidine-1-carbonyl)-2H-indazol-2-yl)-3-phenylpropanoate, N-hydroxy-2-[7-(morpholin-4-ylcarbonyl)-2H-indazol-2-yl]-3-phenylpropanamide, 2-(7-(2-oxa-7-azaspiro[3.5]nonane-7-carbonyl)-2H-indazol-2-yl)-N-hydroxy-3-phenylpropanamide, 2-(7-(3-oxa-9-azaspiro[5.5]undecane-9-carbonyl)-2H-indazol-2-yl)-N-hydroxy-3-phenylpropanamide, 2-(1-(hydroxyamino)-1-oxo-3-phenylpropan-2-yl)-N-(tetrahydro-2H-pyran-4-yl)-2H-indazole-7-carboxamide, 2-(1-(hydroxyamino)-1-oxo-3-phenylpropan-2-yl)-N-((tetrahydro-2H-pyran-4-yl)methyl)-2H-indazole-7-carboxamide, 2-(1-(hydroxyamino)-1-oxo-3-phenylpropan-2-yl)-N-(2-(tetrahydro-2H-pyran-4-yl)ethyl)-2H-indazole-7-carboxamide, 2-(1-(hydroxyamino)-1-oxo-3-phenylpropan-2-yl)-N-(2-morpholinoethyl)-2H-indazole-7-carboxamide, 2-{7-[(Cyclopropylamino)methyl]-2H-indazol-2-yl}-N-hydroxy-3-phenylpropanamide, 2-(7-((cyclopropylmethylamino)methyl)-2H-indazol-2-yl)-N-hydroxy-3-phenylpropanamide, N-hydroxy-3-phenyl-2-(7-(((tetrahydro-2H-pyran-4-ylamino)methyl)-2H-indazol-2-yl)propanamide, N-hydroxy-2-(7-(morpholinomethyl)-2H-indazol-2-yl)-3-phenylpropanamide, N-hydroxy-2-(7-((4-methoxypiperidin-1-yl)methyl)-2H-indazol-2-yl)-3-phenylpropanamide, N-hydroxy-2-(7-((4-morpholinopiperidin-1-yl)methyl)-2H-indazol-2-yl)-3-phenylpropanamide, 2-(7-(2-oxa-7-azaspiro[3.5]nonan-7-ylmethyl)-2H-indazol-2-yl)-N-hydroxy-3-phenylpropanamide, 2-(7-(3-oxa-9-azaspiro [5.5]undecan-9-ylmethyl)-2H-indazol-2-yl)-N-hydroxy-3-phenylpropanamide, N-hydroxy-2-(7-((4-methylpiperazin-1-yl)methyl)-2H-indazol-2-yl)-3-phenylpropanamide, 2-(7-((4,4-difluoropiperidin-1-yl)methyl)-2H-indazol-2-yl)-N-hydroxy-3-phenylpropanamide, 2-(7-((3,3-difluoropiperidin-1-yl)methyl)-2H-indazol-2-yl)-N-hydroxy-3-phenylpropanamide, N-hydroxy-3-phenyl-2-(7-((4-(trifluoromethyl)piperidin-1-yl)methyl)-2H-indazol-2-yl)propanamide, N-hydroxy-2-(7-((4-methyl-3-oxopiperazin-1-yl)methyl)-2H-indazol-2-yl)-3-phenylpropanamide, 2-[1-Benzyl-2-(hydroxyamino)-2-oxoethyl]-3-(cyclopropylethynyl)-N-[2-(tetrahydro-2H-pyran-4-yl)ethyl]-2H-indazole-7-carboxamide, N-hydroxy-3-phenyl-2-(7-(pyrimidin-5-yl)-2H-pyrazolo[3,4-c]pyridin-2-yl)propanamide, N-hydroxy-2-(7-(1-methyl-1H-pyrazol-5-yl)-2H-pyrazolo[3,4-c]pyridin-2-yl)-3-phenylpropanamide, N-hydroxy-3-phenyl-2-(4,5, 6,7-tetrahydro-2H-indazol-2-yl)propanamide, N-hydroxy-3-phenyl-2-(4, 5,6,7-tetrahydro-1H-indazol-1-yl)propanamide, 2-(6-Chloro-1-methyl-1H-indazol-3-yl)-N-hydroxy-3-phenylpropanamide, N-hydroxy-2-(1-methyl-6-(1-methyl-1H-pyrazol-5-yl)-1H-indazol-3-yl)-3-phenylpropanamide, N-hydroxy-2-(1-methyl-6-pyrimidin-5-yl-1H-indazol-3-yl)-3-phenylpropanamide, N-hydroxy-2-(1-methyl-6-(pyridin-4-yl)-1H-indazol-3-yl)-3-phenylpropanamide, 2-(3-(cyclopropylethynyl)-4, 5,6,7-tetrahydro-2H-indazol-2-yl)-N-hydroxy-3-phenylpropanamide, and 2-(3-(cyclopropylethynyl)-7-(pyrimidin-5-yl)-2H-pyrazolo [3,4-c]pyridin-2-yl)-N-hydroxy-3-phenylpropanamide, or a pharmaceutically acceptable salt, a tautomer or a stereoisomer thereof.

23. A pharmaceutical composition comprising a compound of claim 1, or a pharmaceutically acceptable salt, a tautomer or a stereoisomer thereof and a pharmaceutically acceptable carrier or excipient.

24. A method for modulating a histone deacetylase, said method comprising: contacting the histone deacetylase with a compound of claim 1, or a pharmaceutically acceptable salt, a tautomer or a stereoisomer thereof.

* * * * *

UNITED STATES PATENT AND TRADEMARK OFFICE
CERTIFICATE OF CORRECTION

PATENT NO. : 10,723,705 B2
APPLICATION NO. : 15/752807
DATED : July 28, 2020
INVENTOR(S) : Jun Pan et al.

Page 1 of 2

It is certified that error appears in the above-identified patent and that said Letters Patent is hereby corrected as shown below:

On the Title Page

Column 2, (other publications), Line 9, delete "Chern." and insert -- Chem. --.

In the Claims

Column 190, Line 44, Claim 1, delete "$NR^cC(O)R^{c"}$" and insert -- $NR^cC(O)R^c$, --;

Column 190, Line 46, Claim 1, delete "$S(O)R^{c"}$" and insert -- $S(O)_2R^c$ --;

Column 190, Line 46, Claim 1, delete "$S(O)_2NR^cR^C$;" and insert -- $S(O)_2NR^cR^c$; --;

Column 190, Line 50, Claim 1, delete "cycloalkyl-$C_{14}$" and insert -- cycloalkyl-$C_{1-4}$ --;

Column 190, Line 64, Claim 1, delete "—$NR^aC$" and insert -- $NR^aC$ --;

Column 191, Line 16, Claim 1, delete "$NR^cS(O)R$," and insert -- $NR^cS(O)R^c$, --;

Column 191, Line 23, Claim 1, delete "$C_1$-4 alkyl-" and insert -- $C_{1-4}$ alkyl- --;

Column 191, Line 45, Claim 1, delete "aryl-$C_{14}$" and insert -- aryl-$C_{1-4}$ --;

Column 191, Line 47, Claim 1, delete "$C_{14}$" and insert -- $C_{1-4}$ --;

Column 191, Line 48, Claim 1, delete "$C_6$" and insert -- $C_{1-6}$ --;

Column 191, Line 49, Claim 1, delete "$C_6$-10 aryl," and insert -- $C_{6-10}$ aryl, --;

Column 191, Line 53, Claim 1, delete "R" and insert -- $R^a$ --;

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,723,705 B2

Column 191, Line 57, Claim 1, delete "—$R^e$," and insert -- $NHR^e$, --;

Column 191, Line 59, Claim 1, delete "S(O)R," and insert -- $S(O)R^e$, --;

Column 191, Line 63, Claim 1, delete "R" and insert -- $R^r$ --;

Column 192, Lines 17-18, Claim 1, delete "$NR^gC(O)R$," and insert -- $NR^gC(O)R^g$, --;

Column 192, Line 32, Claim 1, delete "C(=NR)$NR^oR^o$," and insert -- C(=$NR^o$)$NR^oR^o$, --;

Column 192, Line 32, Claim 1, delete "$NR^oC$(=NR)$NR^oR^o$," and insert -- $NR^oC$(=$NR^o$)$NR^oR^o$, --;

Column 192, Line 33, Claim 1, delete "$NR^oS(O)_2R$," and insert -- $NR^oS(O)_2R^o$, --;

Column 192, Line 42, Claim 1, delete "$C_6$-10 aryl," and insert -- $C_{6-10}$ aryl, --;

Column 192, Line 59, Claim 1, delete "NR'$S(O)_2R$," and insert -- $NR^iS(O)_2R^i$, --;

Column 192, Line 59, Claim 1, delete "NR'$S(O)_2NR^iR^i$," and insert -- $NR^iS(O)_2NR^iR^i$, --.

Column 196, Lines 7-8, Claim 16, delete "$C_{1-12}$alkyl," and insert -- $C_{1-2}$alkyl, --;

Column 196, Line 8, Claim 16, delete "-$C_{1-12}$alkyl," and insert -- -$C_{1-2}$alkyl, --.

Column 196, Line 37, Claim 17, delete "$NR^cC(O)OR$," and insert -- $NR^cC(O)OR^c$, --;

Column 196, Line 38, Claim 17, delete "$NR^cS(O)_2R^c$" and insert -- $NR^cS(O)_2R^c$, --;

Column 196, Line 39, Claim 17, delete "$S(O)_2NR^iR^i$;" and insert -- $S(O)_2N^cR^c$; --.

Column 201, Line 11, Claim 22, delete "2-(5-cyclopropyl-6H-" and insert -- 2-(5-cyclopropyl-1H- --;

Column 201, Line 54, Claim 22, delete "N-hydroxy-32-(5-" and insert -- N-hydroxy-3-phenyl-2-(5- --;

Column 201, Line 60, Claim 22, delete "-2H-" and insert -- -1H- --;

Column 201, Line 60, Claim 22, delete "-2-yl-N-" and insert -- -1-yl)-N- --;

Column 204, Line 29, Claim 22, delete "-(4,5, 6,7-" and insert -- -(4,5,6,7- --;

Column 204, Line 31, Claim 22, delete "-(4, 5,6,7-" and insert -- -(4,5,6,7- --;

Column 204, Line 41, Claim 22, delete "-4, 5,6,7-" and insert -- -4,5,6,7- --.